US008273780B2

(12) United States Patent  (10) Patent No.: US 8,273,780 B2
Hutchinson et al.  (45) Date of Patent: *Sep. 25, 2012

(54) POLYCYCLIC ANTAGONISTS OF LYSOPHOSPHATIDIC ACID RECEPTORS

(75) Inventors: John Howard Hutchinson, San Diego, CA (US); Thomas Jon Seiders, San Diego, CA (US); Bowei Wang, Westfield, NJ (US); Jeannie M. Arruda, San Diego, CA (US); Jeffrey Roger Roppe, Temecula, CA (US); Timothy Parr, La Mesa, CA (US)

(73) Assignee: Amira Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/246,746

(22) Filed: Sep. 27, 2011

(65) Prior Publication Data

US 2012/0015991 A1  Jan. 19, 2012

Related U.S. Application Data

(63) Continuation of application No. 12/793,440, filed on Jun. 3, 2010, now Pat. No. 8,058,300.

(60) Provisional application No. 61/183,785, filed on Jun. 3, 2009.

(51) Int. Cl.
 *A61K 31/42* (2006.01)
(52) U.S. Cl. ...................................... 514/380
(58) Field of Classification Search .................. 514/364, 514/380; 548/245, 132
 See application file for complete search history.

(56) References Cited

U.S. PATENT DOCUMENTS

| | | | |
|---|---|---|---|
| 6,964,975 B2 | 11/2005 | Ueno et al. | |
| 7,094,797 B2 | 8/2006 | Horie et al. | |
| 7,135,469 B2 | 11/2006 | Pinto | |
| 7,229,987 B2 | 6/2007 | Ammenn et al. | |
| 7,285,680 B2 | 10/2007 | Habashita et al. | |
| 7,288,558 B2 | 10/2007 | Nakade et al. | |
| 7,300,917 B2 | 11/2007 | Nakade et al. | |
| 8,058,300 B2 * | 11/2011 | Hutchinson et al. | 514/380 |
| 2003/0114505 A1 | 6/2003 | Ueno et al. | |
| 2004/0014662 A1 | 1/2004 | Lindquist et al. | |
| 2004/0067908 A1 | 4/2004 | Nakade et al. | |
| 2004/0167132 A1 | 8/2004 | Shankar et al. | |
| 2004/0171037 A1 | 9/2004 | Li et al. | |
| 2004/0171582 A1 | 9/2004 | Nakade et al. | |
| 2004/0192739 A1 | 9/2004 | Solow-Cordero et al. | |
| 2004/0204383 A1 | 10/2004 | Tigyi et al. | |
| 2004/0236112 A1 | 11/2004 | Singh et al. | |
| 2004/0266840 A1 | 12/2004 | Singh et al. | |
| 2005/0065194 A1 | 3/2005 | Shankar et al. | |
| 2005/0101518 A1 | 5/2005 | Solow-Cordero | |
| 2005/0113283 A1 | 5/2005 | Solow-Cordero et al. | |
| 2005/0261298 A1 | 11/2005 | Solow-Cordero et al. | |
| 2006/0009507 A1 | 1/2006 | Miller et al. | |
| 2006/0135577 A1 | 6/2006 | Nakade et al. | |
| 2006/0148830 A1 | 7/2006 | Terakado et al. | |
| 2006/0194850 A1 | 8/2006 | Yamamoto et al. | |
| 2007/0149595 A1 | 6/2007 | Tanaka et al. | |
| 2008/0051372 A1 | 2/2008 | Chun | |
| 2008/0064731 A1 | 3/2008 | Nakade et al. | |
| 2008/0234230 A1 | 9/2008 | Nakade et al. | |
| 2008/0293764 A1 | 11/2008 | Terakado | |
| 2010/0034814 A1 | 2/2010 | Sabbadini et al. | |
| 2010/0152257 A1 | 6/2010 | Hutchinson et al. | |
| 2011/0082164 A1 | 4/2011 | Clark et al. | |
| 2011/0082181 A1 | 4/2011 | Seiders et al. | |

FOREIGN PATENT DOCUMENTS

| | | |
|---|---|---|
| EP | 0702012 A1 | 3/1996 |
| EP | 1258484 A1 | 11/2002 |
| EP | 1550461 A1 | 7/2005 |
| GB | 2466121 B | 12/2010 |
| GB | 2470833 | 12/2010 |
| JP | 11-240873 A | 9/1999 |
| JP | 2006-096712 A | 4/2006 |
| WO | WO-98-28282 A2 | 7/1998 |
| WO | WO-00-59902 A2 | 10/2000 |
| WO | WO-01-60819 A1 | 8/2001 |
| WO | WO-02-00651 A2 | 1/2002 |
| WO | WO-02-085290 | 10/2002 |
| WO | WO-03-062392 A2 | 7/2003 |
| WO | WO-03-097047 A1 | 11/2003 |
| WO | WO-2004-031118 A1 | 4/2004 |
| WO | WO-2005-012269 A1 | 2/2005 |
| WO | WO-2005-066138 A1 | 7/2005 |
| WO | WO-2006-131336 A1 | 12/2006 |
| WO | WO-2007-007588 A1 | 1/2007 |
| WO | WO-2007-024922 | 3/2007 |
| WO | WO-2007-096647 A2 | 8/2007 |
| WO | WO-2007-139946 A2 | 12/2007 |
| WO | WO 2008-014286 | 1/2008 |

(Continued)

OTHER PUBLICATIONS

Anliker et al., "Cell surface receptors in lysophospholipid signaling," Seminars Cell Develop Biol 15:457-465 (2004).
Castelino et al., "Genetic deletion or pharmacologic antagonism of LPA$_1$ ameliorates dermal fibrosis in a mouse model of systemic sclerosis," 11th International Workshop on Scleroderma Research, Abstracts, Aug. 1-4, 2010, Boston, MA, p. S-57.
Choi et al., "Biological roles of lysophospholipid receptors revealed by genetic null mice: An update," Biochim Biophys Acta 1781:531-539 (2008).
Chun and Rosen, "Lysophospholipid Receptrs as Potential Drug Targets in Tissue Transplantation and Autoimmune Diseases," Curr Pharma Design 12:161-171 (2006).

(Continued)

Primary Examiner — Kristin Bianchi
(74) Attorney, Agent, or Firm — Wilson, Sonsini, Goodrich & Rosati; Maureen S. Gibbons

(57) ABSTRACT

Described herein are compounds that are antagonists of lysophosphatidic receptor(s). Also described are pharmaceutical compositions and medicaments that include the compounds described herein, as well as methods of using such antagonists, alone and in combination with other compounds, for treating LPA-dependent or LPA-mediated conditions or diseases.

16 Claims, 5 Drawing Sheets

FOREIGN PATENT DOCUMENTS

| | | |
|---|---|---|
| WO | WO-2008-024979 A2 | 2/2008 |
| WO | WO-2008-112201 A2 | 9/2008 |
| WO | WO-2009-011850 A2 | 1/2009 |
| WO | WO-2009-135590 A1 | 11/2009 |
| WO | WO-2010-068775 A2 | 6/2010 |
| WO | WO-2010-077882 A2 | 7/2010 |
| WO | WO-2010-077883 A2 | 7/2010 |
| WO | WO-2010-141761 A2 | 12/2010 |
| WO | WO-2010-141768 | 12/2010 |
| WO | WO-2010-141768 A2 | 12/2010 |
| WO | WO-2011-017350 A2 | 2/2011 |
| WO | WO 2011-041461 A2 | 4/2011 |
| WO | WO-2011-041462 A2 | 4/2011 |
| WO | WO-2011-041694 A2 | 4/2011 |
| WO | WO-2011-041729 A2 | 4/2011 |
| WO | WO 2011-159632 | 12/2011 |
| WO | WO 2011-159633 | 12/2011 |
| WO | WO 2011-159635 | 12/2011 |

OTHER PUBLICATIONS

Chun, "Lysophospholipids in the nervous system," Prostaglandins & other Lipid Mediators 77:46-51 (2005).

Fukushima et al., "The LPA Receptors," Prostaglandins & other Lipid Mediators 64:21-32 (2001).

Gardell et al., "Emerging medicinal roles for lysophospholipid signaling," Trends in Mol Med 12(2):65-75 (2006).

Ishii et al., "Lysophospholipid Receptors: Signaling and Biology," Annu Rev Biochem 73:321-354 (2004).

Ley and Zarbock, "From lung injury to fibrosis," Nature Medicine 14(1):20-21 (2008).

Mills and Moolenaar, "The Emerging Role of Lysophosphatidic Acid in Cancer," Nature Reviews/Cancer 3:582-591 (2003).

Murph et al., "Sharpening the edges of understanding the structure/function of the LPA1 receptor: Expression in cancer and mechanisms of recognition," Biochim Biophys Acta 1781:547-557 (2008).

Ohta et al., "Ki16425, a Subtype-Selective Antagonist for EDG-Family Lysophosphatidic Acid Receptors," Mol Pharma 64(4):994-1005 (2003).

Parrill et al., "Sphingosine 1-phosphate and lysophosphatidic acid receptors: agonist and antagonist binding and progress toward development of receptor-specific ligands," Seminars Cell Develop Biol 15:467-476 (2004).

Pradere et al., "Lysophosphatidic acid and renal fibrosis," Biochim Biophys Acta (2008) doi:10.1016/j.bbalip.2008.04.001.

Pradere et al., "$LPA_1$ Receptor Activation Promotes Renal Insterstitial Fibrosis," J Am Soc Nephrol 18:3110-3118 (2007).

Prestwich et al., "New metabolically stabilized analogues of lysophosphatidic acid: agonists, antagonists and enzyme inhibitors," Biochem Society Transactions 33(6):1357-1361 (2005).

Sardar et al., "Molecular basis for lysophoshatidic acid receptor antagonist selectivity," Biochim Biophys Acta 1582:309-317 (2002).

Scott, "Lysophosphatidic acid is an important mediator of fibroblast recruitment in IPF," Thorax 63:654 (2008).

Swaney et al., "Pharmacokinetic and Pharmacodynamic Characterization of an Oral, $LPA_1$-selective Antagonist," Journal of Pharmacology and Experimental Therapeutics , published Dec. 15, 2010 as DOI:10.1124/jpet,110.175901.

Swaney et al., "A novel, orally activa $LPA_1$ receptor antagonist inhibits lung fibrosis in the mouse bleomycin model," British J Pharmacol. 160:1699-1713 (2010).

Tager et al., "The Lysophosphatidic Acid Receptor $LPA_1$ Links Pulmonary Fibrosis to Lung Injury by Mediating Fibroblast Recruitment and Vascular Leak," Nature Medicine 14(I):45-54 (2008).

Toews et al., "Lysophosatidic acid in airway function and disease," Biochim Biophys Acta 1582:240-250 (2002).

Watanabe et al., "Plasma lysophosphatidic acid level and serum autotaxin activity are increased in liver injury in rats in relation to its severity," Life Sciences 81:1009-1015 (2007).

Watanabe et al., "Both Plasma Lysophosphatidic Acid and Serum Autotaxin Levels are Increased in Chronic Hepatitis C," J. Clin. Gastroenterol. 41(6):616-623 (2007).

Watterson et al., "Regulation of fibroblast functions by lysophospholipid mediators: Potential roles in wound healing," Wound Rep Reg 15:607-616 (2007).

Yamamoto et al., "Synthesis and evaluation of isoxazole derivatives as lysophosphatidic acid (LPA) antagonists," Bioorg. Med. Chem. Ltrs. 17(13):3736-3740 (2007).

Yang et al., "G protein-coupled lysophosphatidic acid receptors stimulate proliferation of colon cancer cells through the β-catenin pathway," PNAS 102(17):6027-6032 (2005).

Yang et al., "In vivo roles of lysophospholipid receptors revealed by gene targeting studies in mice," Biochim Biophys Acta 1582:197-203 (2002).

Yokoyama et al., "Stereochemical properties of lysophosphatidic acid receptor activation and metabolism," Biochim Biophys Acta 1582:295-308 (2002).

Zhao and Natarajin, "Lysophosphatidic acid signaling in airway epithelium: Role in airway inflammation and remodeling," Cellular Signaling 21:367-377 (2009).

GB-0921606.0 Search Report dated Dec. 23, 2009.

PCT/US09/068106 Search Report and Written Opinion mailed Jun. 23, 2010.

PCT/US09/068105 Search Report and Written Opinion mailed Aug. 13, 2010.

Castelino et al., "Genetic deletion or pharmacologic antagonism of LPA1 ameliorates dermal fibrosis in a scleroderma mouse model," Arthritis & Rheumatism DOI 10.1002/art.30262, accepted Jan. 18, 2011.

Evans et al., "Seeing the future of bioactive lipid drug targets," Nature Chemical Biology 6:476-479 (2010).

PCT/US10/37309 Search Report and Written Opinion mailed Feb. 28, 2011.

PCT/US10/37316 Search Report and Written Opinion mailed Feb. 9, 2011.

PCT/US10/44284 Search Report and Written Opinion mailed Apr. 26, 2011.

Lala et al., Role of nitric oxide in tumor progression: Lessons from experimental tumors, Cancer and Metastasis Reviews (1998), 17, 91-106.

Golub et al., Molecular Classification of Cancer: Class Discovery and Class Prediction by Gene Expression Monitoring, Science (1999), vol. 286, 531-537.

Bissantz. "Development and Application of new Methods for the Virtual Screening of Chemical Databases." Doctoral Dissertation, Swiss Federal Institute of Technology, 2002.

\* cited by examiner

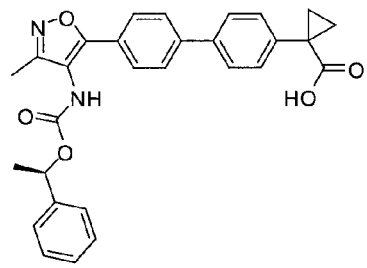
Compound 1
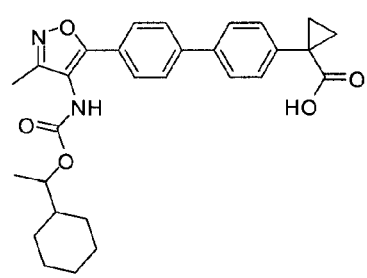
Compound 2
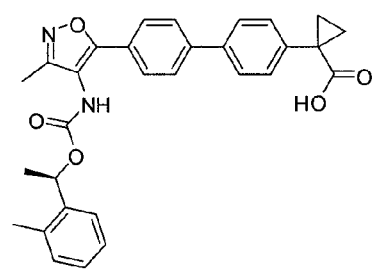
Compound 3
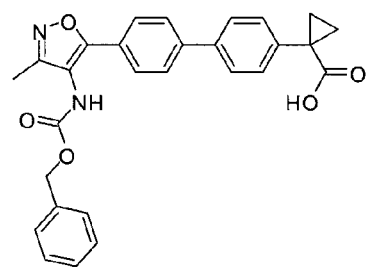
Compound 4
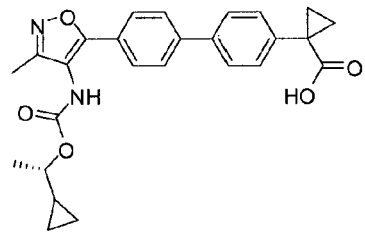
Compound 5
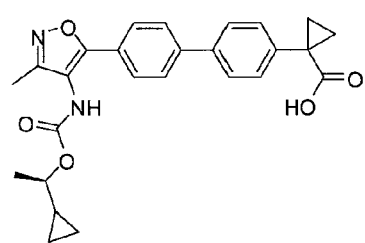
Compound 6
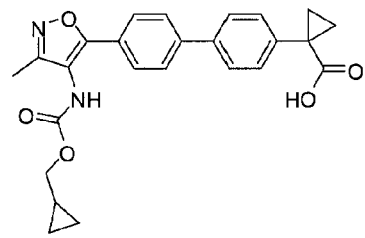
Compound 7
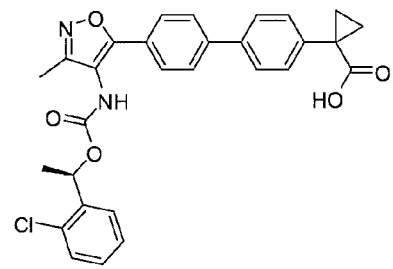
Compound 8
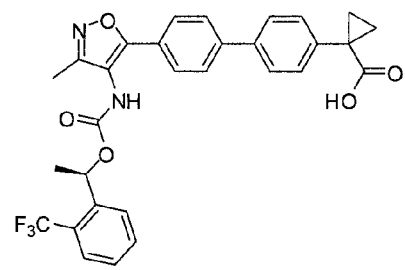
Compound 9
FIGURE No. 1

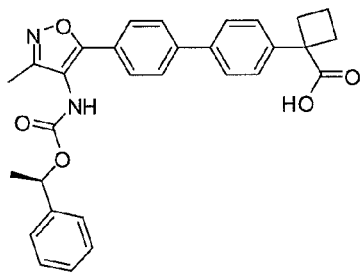
Compound 10
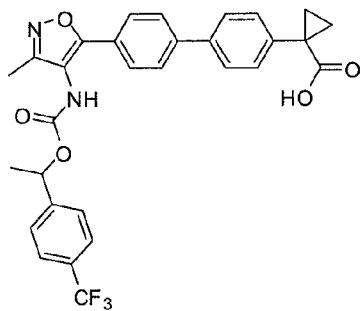
Compound 14
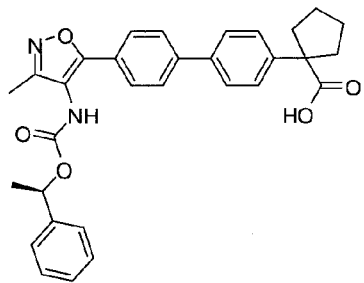
Compound 11
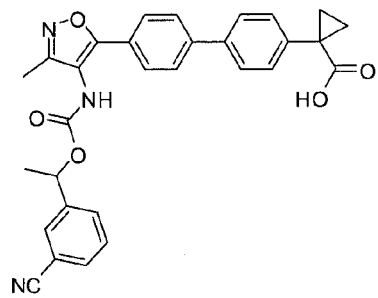
Compound 15
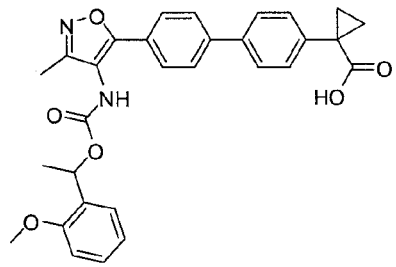
Compound 12
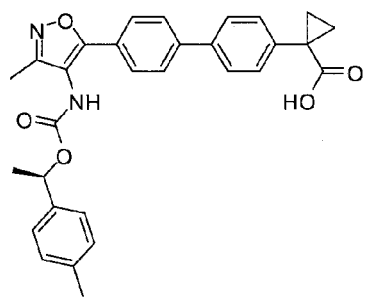
Compound 16
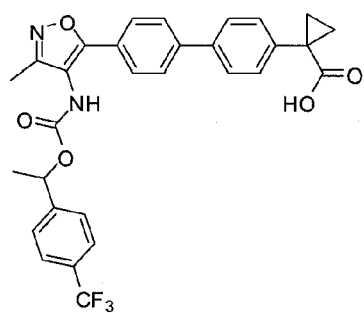
Compound 13
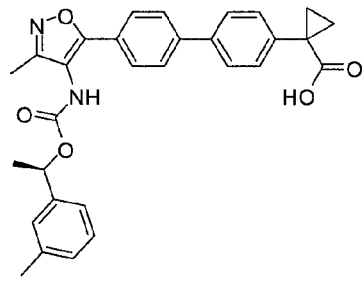
Compound 17
FIGURE No. 2

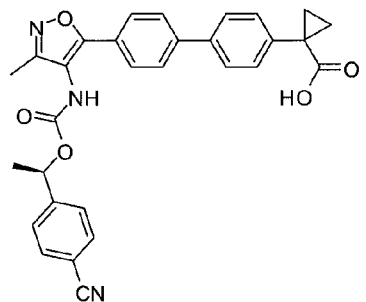
Compound 18
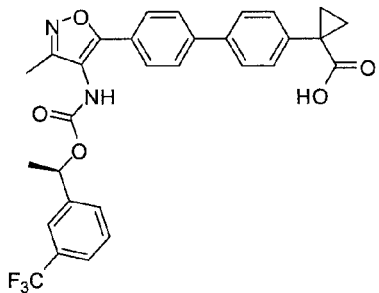
Compound 22
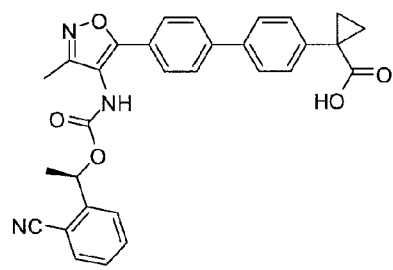
Compound 19
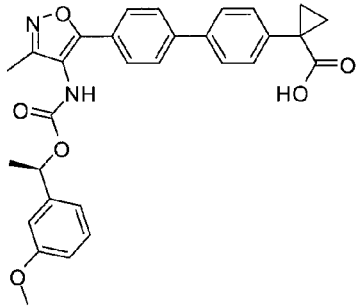
Compound 23
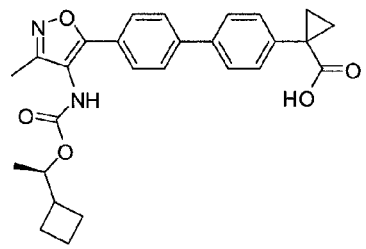
Compound 20
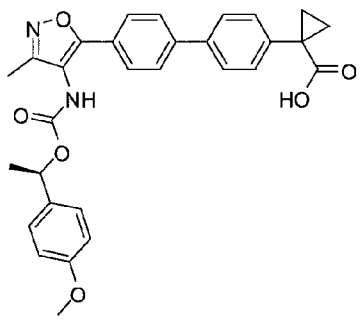
Compound 24
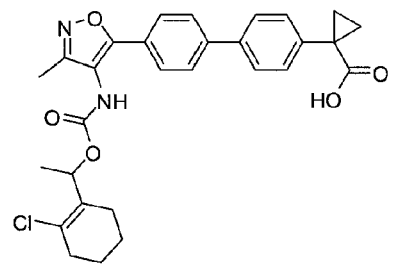
Compound 21
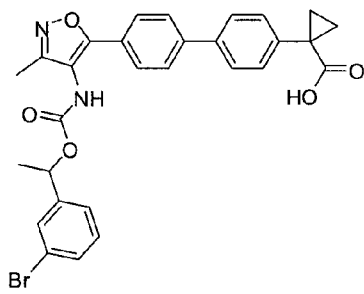
Compound 25
FIGURE No. 3

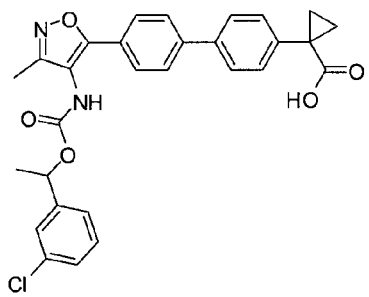
Compound 26
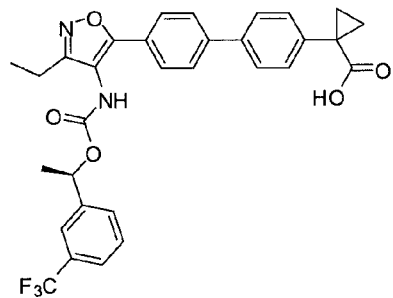
Compound 30
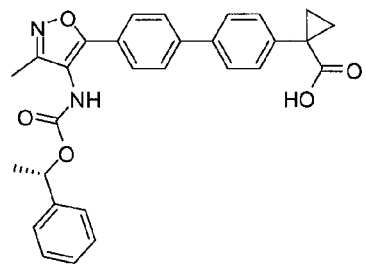
Compound 27
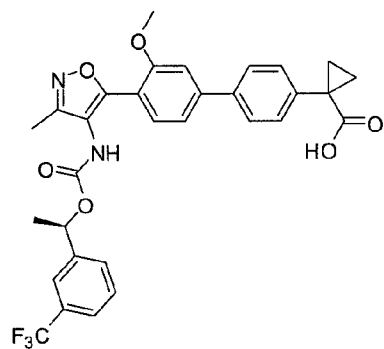
Compound 31
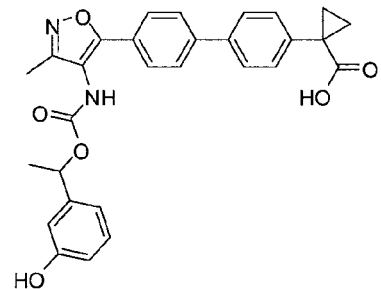
Compound 28
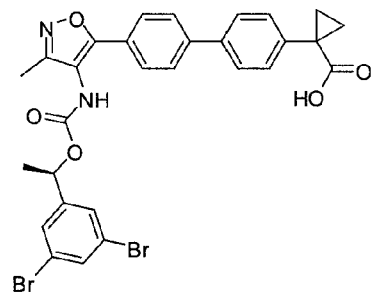
Compound 32
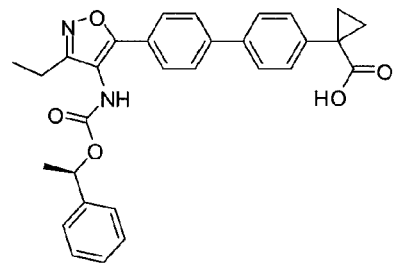
Compound 29
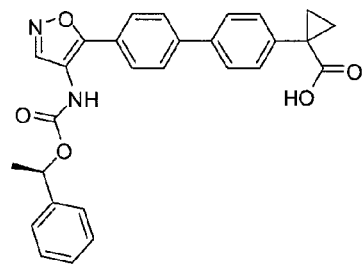
Compound 33
FIGURE No. 4

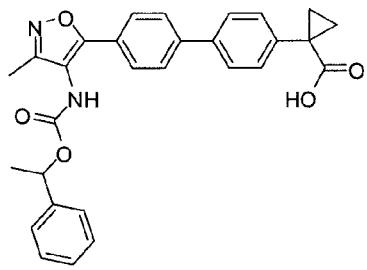
Compound 34
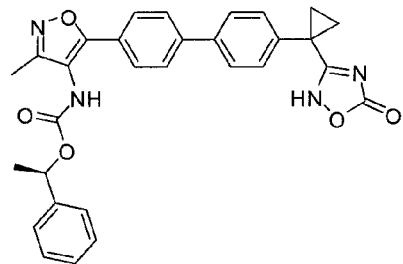
Compound 38
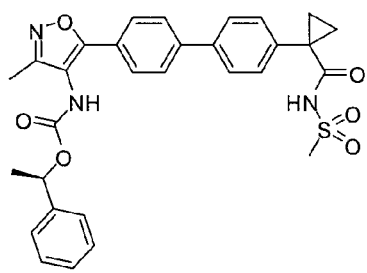
Compound 35
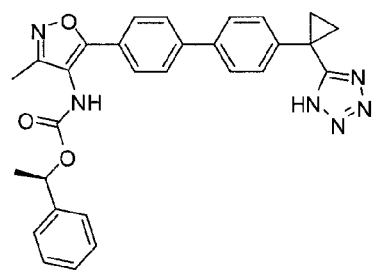
Compound 39
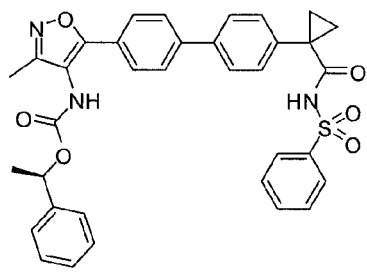
Compound 36
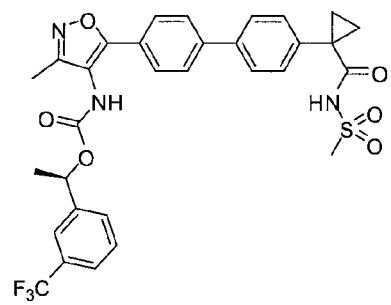
Compound 40
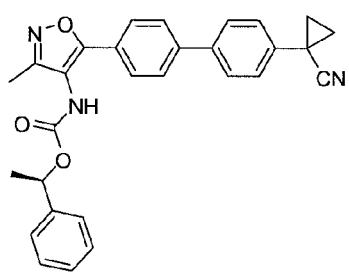
Compound 37
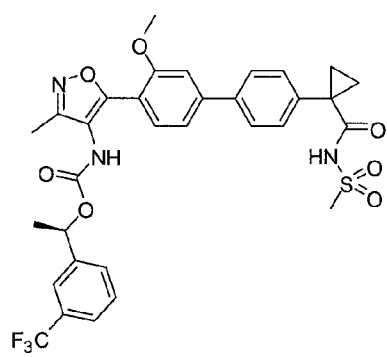
Compound 41
FIGURE No. 5

POLYCYCLIC ANTAGONISTS OF LYSOPHOSPHATIDIC ACID RECEPTORS

RELATED APPLICATIONS

This application is a continuation application of co-pending U.S. application Ser. No. 12/793,440 entitled "POLYCYCLIC ANTAGONISTS OF LYSOPHOSPHATIDIC ACID RECEPTORS" filed on Jun. 3, 2010, which claims the benefit of U.S. Provisional Application No. 61/183,785, entitled "ANTAGONISTS OF LYSOPHOSPHATIDIC ACID RECEPTORS" filed on Jun. 3, 2009, all of which are herein incorporated by reference in their entirety.

FIELD OF THE INVENTION

Described herein are compounds, methods of making such compounds, pharmaceutical compositions and medicaments comprising such compounds, and methods of using such compounds to treat, prevent or diagnose diseases, disorders or conditions associated with one or more of the lysophosphatidic acid (LPA) receptors.

BACKGROUND OF THE INVENTION

Lysophospholipids are membrane-derived bioactive lipid mediators. Lysophospholipids affect fundamental cellular functions that include proliferation, differentiation, survival, migration, adhesion, invasion, and morphogensis. These functions influence many biological processes that include, but are not limited to, neurogensis, angiogenesis, wound healing, fibrosis, immunity, and carcinogenesis.

Lysophosphatidic acid (LPA) is a lysophospholipid that has been shown to act through sets of specific G protein-coupled receptors (GPCRs) in an autocrine and paracrine fashion. LPA binding to its cognate GPCRs ($LPA_1$, $LPA_2$, $LPA_3$, $LPA_4$, $LPA_5$, $LPA_6$) activates intracellular signaling pathways to produce a variety of biological responses. Antagonists of the LPA receptors find use in the treatment of diseases, disorders or conditions in which LPA plays a role.

SUMMARY OF THE INVENTION

In one aspect, presented herein are compounds of Formula (I) that inhibit the physiological activity of lysophosphatidic acid (LPA), and therefore, are useful as agents for the treatment or prevention of diseases in which inhibition of the physiological activity of LPA is useful, such as diseases in which an LPA receptor participates, is involved in the etiology or pathology of the disease, or is otherwise associated with at least one symptom of the disease.

In one aspect, the compounds of Formula (I) are useful for the treatment of fibrosis of organs (liver, kidney, lung, heart and the like), liver diseases (acute hepatatis, chronic hepatitis, liver fibrosis, liver cirrhosis, portal hypertension, regenerative failure, non-alcoholic steatohepatitis (NASH), liver hypofunction, hepatic blood flow disorder, and the like), cell proliferative disease (cancer (solid tumor, solid tumor metastasis, vascular fibroma, myeloma, multiple myeloma, Kaposi's sarcoma, leukemia, chronic lymphocytic leukemia (CLL) and the like) and invasive metastasis of cancer cell, and the like), inflammatory disease (psoriasis, nephropathy, pneumonia and the like), gastrointestinal tract disease (irritable bowel syndrome (IBS), inflammatory bowel disease (IBD), abnormal pancreatic secretion, and the like), renal disease, urinary tract-associated disease (benign prostatic hyperplasia or symptoms associated with neuropathic bladder disease, spinal cord tumor, hernia of intervertebral disk, spinal canal stenosis, symptoms derived from diabetes, lower urinary tract disease (obstruction of lower urinary tract, and the like), inflammatory disease of lower urinary tract, dysuria, frequent urination, and the like), pancreas disease, abnormal angiogenesis-associated disease (arterial obstruction and the like), scleroderma, brain-associated disease (cerebral infarction, cerebral hemorrhage, and the like), neuropathic pain, peripheral neuropathy, and the like, ocular disease (age-related macular degeneration (AMD), diabetic retinopathy, proliferative vitreoretinopathy (PVR), cicatricial pemphigoid, glaucoma filtration surgery scarring, and the like). In one aspect, the compounds of Formula (I) are used in the treatment of fibrotic diseases or conditions.

In one aspect, described herein are compounds of Formula (I), pharmaceutically acceptable salts, solvates, and prodrugs thereof. Compounds of Formula (I) are antagonists of at least one of the LPA receptors selected from $LPA_1$, $LPA_2$, $LPA_3$, $LPA_4$, $LPA_5$ and $LPA_6$. In one embodiment, compounds of Formula (I) are antagonists of $LPA_1$. In one embodiment, compounds of Formula (I) are antagonists of $LPA_1$ and/or $LPA_3$. In some embodiments, compounds of Formula (I) are antagonists of $LPA_1$ and/or $LPA_2$. In some embodiments, compounds of Formula (I) are selective antagonists for one of the LPA receptors relative to the other LPA receptors. In some embodiments, such a selective antagonist is selective for the $LPA_1$ receptor. In some embodiments, such a selective antagonist is selective for the $LPA_2$ receptor. In some embodiments, such a selective antagonist is selective for the $LPA_3$ receptor.

Compounds of Formula (I) are used in the treatment of diseases, disorders, or conditions in which activation of at least one LPA receptor by LPA contributes to the symptomology or progression of the disease, disorder or condition. In one aspect, the methods, compounds, pharmaceutical compositions, and medicaments described herein comprise antagonists of LPA receptor(s). In one aspect, the methods, compounds, pharmaceutical compositions, and medicaments described herein comprise antagonists of $LPA_1$, $LPA_2$, or $LPA_3$, or combinations thereof.

In one aspect, provided herein is a compound of Formula (I), or a pharmaceutically acceptable salt thereof:

Formula (I)

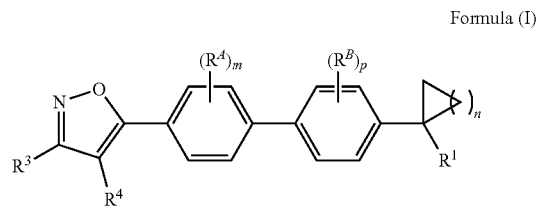

wherein
$R^1$ is —$CO_2H$, —$CO_2R^D$, —CN, —C(=O)N($R^9$)$_2$, —C(=O)NHCH$_2$CH$_2$SO$_3$H, or —C(=O)NHSO$_2$R$^{10}$, tetrazolyl, or 5-oxo-2,5-dihydro-[1,2,4]oxadiazol-3-yl;
$R^D$ is H or $C_1$-$C_4$alkyl;
$R^3$ is H, $C_1$-$C_4$alkyl, $C_3$-$C_6$cycloalkyl, or $C_1$-$C_4$fluoroalkyl;
$R^4$ is —$NR^7C(=O)OCH(R^8)$—CY;
$R^7$ is H or $C_1$-$C_4$alkyl;
$R^8$ is H, $C_1$-$C_4$alkyl, or $C_1$-$C_4$fluoroalkyl;
CY is a substituted or unsubstituted $C_3$-$C_6$cycloalkyl or a substituted or unsubstituted phenyl, wherein if CY is substituted then CY is substituted with 1 or 2 $R^C$;

$R^9$ is H, $C_1$-$C_6$alkyl, $C_1$-$C_6$fluoroalkyl, $C_3$-$C_6$cycloalkyl, or a substituted or unsubstituted phenyl;

$R^{10}$ is a $C_1$-$C_6$alkyl, $C_1$-$C_6$fluoroalkyl, $C_3$-$C_6$cycloalkyl, or a substituted or unsubstituted phenyl;

each of $R^A$, $R^B$, and $R^C$ are independently selected from F, Cl, Br, I, —CN, —OH, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;

m is 0, 1, or 2; n is 1, 2, 3 or 4; p is 0, 1, or 2.

In some embodiments, $R^1$ is —$CO_2H$, —$CO_2R^D$, —C(=O)$NHSO_2R^{10}$ or tetrazolyl; $R^3$ is H or $C_1$-$C_4$alkyl; $R^7$ is H; $R^8$ is H, —$CH_3$ or —$CF_3$; $R^{10}$ is a $C_1$-$C_6$alkyl or a substituted or unsubstituted phenyl; each $R^A$ is independently selected from F, Cl, Br, I, —OH, —$CH_3$, —$CF_3$, —$OCF_3$, and —$OCH_3$; each $R^B$ is independently selected from F, Cl, Br, I, —OH, —$CH_3$, —$CF_3$, —$OCF_3$, and —$OCH_3$; each $R^C$ is independently selected from F, Cl, Br, I, —OH, —$CH_3$, —$CF_3$, —$OCF_3$, and —$OCH_3$; m is 0 or 1; n is 1, 2, or 3; p is 0 or 1.

In some embodiments, $R^1$ is —$CO_2H$ or —$CO_2R^D$; $R^D$ is H, —$CH_3$, or —$CH_2CH_3$; $R^3$ is H, —$CH_3$ or —$CH_2CH_3$; $R^4$ is —NHC(=O)OCH($R^8$)—CY; $R^8$ is H, or —$CH_3$; CY is a substituted or unsubstituted phenyl, wherein if CY is a substituted phenyl then the phenyl is substituted with 1 or 2 $R^C$.

In some embodiments, the compound of Formula (I) has the following structure:

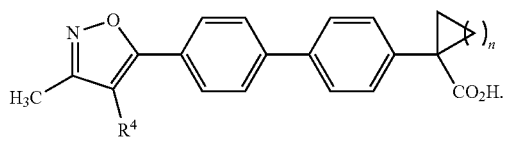

In some embodiments, $R^4$ is

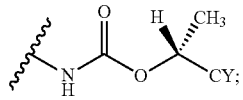

CY is a substituted or unsubstituted phenyl, wherein if CY is a substituted phenyl then the phenyl is substituted with 1 or 2 $R^C$; $R^C$ is F, Cl, —OH, —$CH_3$, —$CF_3$, or —$OCH_3$; n is 1.

In some embodiments, CY is phenyl, 2-fluorophenyl, 3-fluorophenyl, 2-chlorophenyl, 3-chlorophenyl, 2-methylphenyl, 3-methylphenyl, 2-trifluoromethylphenyl, or 3-trifluoromethylphenyl.

In some embodiments, $R^1$ is —C(=O)$NHSO_2R^{10}$; $R^3$ is —$CH_3$ or —$CH_2CH_3$; $R^8$ is H, or —$CH_3$; $R^{10}$ is —$CH_3$, or —$CH_2CH_3$.

In some embodiments, $R^4$ is —NHC(=O)OCH($CH_3$)-(substituted or unsubstituted phenyl); wherein if the phenyl is substituted then the phenyl is substituted with $R^C$; $R^C$ is F, Cl, —$CH_3$, or $CF_3$; n is 1.

In some embodiments, $R^4$ is

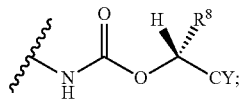

$R^8$ is —$CH_3$; CY is a substituted or unsubstituted phenyl, wherein if CY is a substituted phenyl then the phenyl is substituted with 1 or 2 $R^C$; $R^C$ is F, Cl, —OH, —$CH_3$, —$CF_3$, or —$OCH_3$; n is 1.

In some embodiments, CY is phenyl, 2-fluorophenyl, 3-fluorophenyl, 2-chlorophenyl, 3-chlorophenyl, 2-methylphenyl, 3-methylphenyl, 2-trifluoromethylphenyl, or 3-trifluoromethylphenyl.

In some embodiments, the compound of Formula (I) has the following structure:

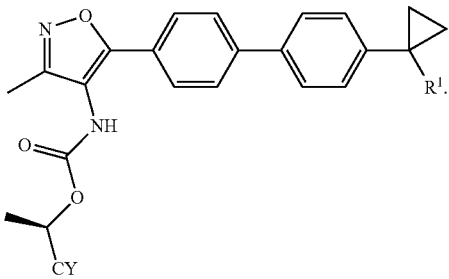

In some embodiments, $R^1$ is —$CO_2H$; CY is phenyl, 2-fluorophenyl, 3-fluorophenyl, 2-chlorophenyl, 3-chlorophenyl, 2-methylphenyl, 3-methylphenyl, 2-trifluoromethylphenyl, or 3-trifluoromethylphenyl.

In some embodiments, $R^1$ is —$CO_2H$, —$CO_2R^D$, —C(=O)$NHSO_2R^{10}$, tetrazolyl, or 5-oxo-2,5-dihydro-[1,2,4]oxadiazol-3-yl. In some embodiments, $R^1$ is —$CO_2H$, —$CO_2R^D$, —C(=O)$NHSO_2R^{10}$, or tetrazolyl. In some embodiments, $R^1$ is —$CO_2H$, —$CO_2R^D$, or —C(=O)$NHSO_2R^{10}$.

In some embodiments, $R^1$ is —$CO_2H$, —$CO_2R^D$, —C(=O)$NHSO_2R^{10}$, tetrazolyl, or 5-oxo-2,5-dihydro-[1,2,4]oxadiazol-3-yl; $R^3$ is H or $C_1$-$C_4$alkyl; $R^7$ is H; $R^8$ is H, or —$CH_3$; $R^{10}$ is a $C_1$-$C_6$alkyl or a substituted or unsubstituted phenyl; CY is cyclopropyl, cyclobutyl, cyclopentyl, cyclopent-1-enyl, 2-chlorocyclopent-1-enyl, cyclohexyl, cyclohex-1-enyl, 2-chlorocyclohex-1-enyl, phenyl, 2-fluorophenyl, 2,3-difluorophenyl, 2,4-difluorophenyl, 2,5-difluorophenyl, 2,6-difluorophenyl, 2-chlorophenyl, 2,6-dichlorophenyl, 2-bromophenyl, 3-bromophenyl, 2,4-dichlorophenyl, 2-hydroxyphenyl, 3-hydroxyphenyl, 4-hydroxyphenyl, 2-methoxyphenyl, 3-methoxyphenyl, 4-methoxyphenyl, 2-trifluoromethylphenyl, 3-trifluoromethylphenyl, 4-trifluoromethylphenyl, 2-fluoro-4-methoxyphenyl, 2-methylphenyl, 3-methylphenyl, 4-methylphenyl, 2-cyanophenyl, 3-cyanophenyl, or 4-cyanophenyl.

In some embodiments, each $R^A$ is independently selected from F, Cl, —$CH_3$, —$CF_3$, —OH, —$OCF_3$, and —$OCH_3$; each $R^B$ is independently selected from F, Cl, —$CH_3$, —$CF_3$, —OH, —$OCF_3$, and —$OCH_3$; m is 0 or 1; p is 0 or 1. In some embodiments, n is 1.

Any combination of the groups described above for the various variables is contemplated herein. Throughout the specification, groups and substituents thereof are chosen by one skilled in the field to provide stable moieties and compounds.

In one aspect, provided are compounds presented in Table 1, Table 2, FIG. 1, FIG. 2, FIG. 3, FIG. 4, and FIG. 5.

Compounds of Formula (I) are antagonists of at least one LPA receptor. In some embodiments, the compound of Formula (I) is an antagonist of $LPA_1$. In some embodiments, the compound of Formula (I) is an antagonist of LPA$_2$. In some embodiments, the compound of Formula (I) is an antagonist of LPA$_3$.

In some embodiments, presented herein are compounds selected from active metabolites, tautomers, solvates, pharmaceutically acceptable salts or prodrugs of a compound of Formula (I).

In some embodiments, provided is a pharmaceutical composition comprising a therapeutically effective amount of a compound of Formula (I). In some embodiments, the pharmaceutical composition also contains at least one pharmaceutically acceptable inactive ingredient.

In some embodiments, provided is a pharmaceutical composition comprising a therapeutically effective amount of a compound of Formula (I), or a pharmaceutically acceptable salt thereof, and at least one pharmaceutically acceptable inactive ingredient. In one aspect, the pharmaceutical composition is formulated for intravenous injection, subcutaneous injection, oral administration, inhalation, nasal administration, topical administration, ophthalmic administration or otic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In some embodiments, the pharmaceutical composition further comprises one or more additional therapeutically active agents other than a compound of Formula (I).

In some embodiments, provided is a method comprising administering a compound of Formula (I) to a human with a LPA-dependent or LPA-mediated disease or condition. In some embodiments, the human is already being administered one or more additional therapeutically active agents other than a compound of Formula (I). In some embodiments, the method further comprises administering one or more additional therapeutically active agents other than a compound of Formula (I).

In some embodiments, the one or more additional therapeutically active agents other than a compound of Formula (I) are selected from: corticosteroids, immunosuppresants, analgesics, anti-cancer agent, anti-inflammatories, chemokine receptor antagonists, bronchodilators, leukotriene receptor antagonists, leukotriene formation inhibitors, monoacylglycerol kinase inhibitors, phospholipase A$_1$ inhibitors, phospholipase A$_2$ inhibitors, and lysophospholipase D (lysoPLD) inhibitors, autotaxin inhibitors, decongestants, antihistamines, mucolytics, anticholinergics, antitussives, expectorants, and β-2 agonists.

In another aspect is the use of a compound of Formula (I) in the treatment of a disease, disorder or condition in which the activity of at least one LPA receptor contributes to the pathology and/or symptoms of the disease or condition. In one embodiment of this aspect, the LPA receptor is selected from LPA$_1$, LPA$_2$, LPA$_3$, LPA$_4$, LPA$_5$ and LPA$_6$. In some embodiments, the LPA receptor is LPA$_1$ or LPA$_2$ or LPA$_3$. In some embodiments, the disease or condition is any of the diseases or conditions specified herein.

Also provided is a method of inhibiting the physiological activity of LPA in a mammal comprising administering a therapeutically effective amount of a compound of Formula (I) or a pharmaceutically acceptable salt thereof to the mammal in need thereof.

In one aspect, is a method for treating or preventing a LPA-dependent or LPA-mediated disease or condition in a mammal comprising administering a therapeutically effective amount of a compound of Formula (I).

In one aspect, LPA-dependent or LPA-mediated diseases or conditions include, but are not limited to, fibrosis of organs or tissues, scarring, liver diseases, dermatological conditions, cancer, cardiovascular disease, respiratory diseases or conditions, inflammatory disease, gastrointestinal tract disease, renal disease, urinary tract-associated disease, inflammatory disease of lower urinary tract, dysuria, frequent urination, pancreas disease, arterial obstruction, cerebral infarction, cerebral hemorrhage, pain, peripheral neuropathy, and fibromyalgia.

In some embodiments, the LPA-dependent or LPA-mediated disease or condition is selected from idiopathic pulmonary fibrosis; other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease); radiation induced fibrosis; chronic obstructive pulmonary disease (COPD); scleroderma; bleomycin induced pulmonary fibrosis; chronic asthma; silicosis; asbestos induced pulmonary fibrosis; acute respiratory distress syndrome (ARDS); kidney fibrosis; tubulointerstitium fibrosis; glomerular nephritis; focal segmental glomerular sclerosis; IgA nephropathy; hypertension; Alport; gut fibrosis; liver fibrosis; cirrhosis; alcohol induced liver fibrosis; toxic/drug induced liver fibrosis; hemochromatosis; nonalcoholic steatohepatitis (NASH); biliary duct injury; primary biliary cirrhosis; infection induced liver fibrosis; viral induced liver fibrosis; and autoimmune hepatitis; corneal scarring; hypertrophic scarring; Duputren disease, keloids, cutaneous fibrosis; cutaneous scleroderma; spinal cord injury/fibrosis; myelofibrosis; vascular restenosis; atherosclerosis; arteriosclerosis; Wegener's granulomatosis; Peyronie's disease, chronic lymphocytic leukemia, tumor metastasis, transplant organ rejection, endometreosis, neonatal respiratory distress syndrome and neuropathic pain.

In one aspect, is a method for treating or preventing cancer in a mammal comprising administering a therapeutically effective amount of a compound of Formula (I) or a pharmaceutically acceptable salt thereof to the mammal in need thereof.

In one aspect, is a method for treating or preventing fibrosis in a mammal comprising administering a therapeutically effective amount of a compound of Formula (I) or a pharmaceutically acceptable salt thereof to the mammal in need thereof.

In one aspect, is a method for treating or preventing lung fibrosis, asthma, chronic obstructive pulmonary disease (COPD), renal fibrosis, acute kidney injury, chronic kidney disease, liver fibrosis, skin fibrosis, fibrosis of the gut, breast cancer, pancreatic cancer, ovarian cancer, prostate cancer, glioblastoma, bone cancer, colon cancer, bowel cancer, head and neck cancer, melanoma, multiple myeloma, chronic lymphocytic leukemia, cancer pain, tumor metastasis, transplant organ rejection, scleroderma, ocular fibrosis, age related macular degeneration (AMD), diabetic retinopathy, collagen vascular disease, atherosclerosis, Raynaud's phenomenom, or neuropathic pain in a mammal comprising administering a therapeutically effective amount of a compound of Formula (I) or a pharmaceutically acceptable salt thereof to the mammal in need thereof.

In one aspect, provided is a method for the treatment or prevention of organ fibrosis in a mammal comprising administering a therapeutically effective amount of a compound of Formula (I) or a pharmaceutically acceptable salt thereof to a mammal in need thereof. In some embodiments, the organ fibrosis comprises lung fibrosis, renal fibrosis, or hepatic fibrosis.

In one aspect, provided is a method of improving lung function in a mammal comprising administering a therapeutically effective amount of a compound of Formula (I) or a pharmaceutically acceptable salt thereof to the mammal in need thereof. In one aspect, the mammal has been diagnosed as having lung fibrosis.

In one aspect, compounds disclosed herein are used to treat idiopathic pulmonary fibrosis (usual interstitial pneumonia) in a mammal.

In one aspect, compounds disclosed herein are used to treat Raynaud's phenomenon. Raynaud's phenomenon comprises both Raynaud's disease (where the phenomenon is idiopathic) and Raynaud's syndrome, where it is caused by some other instigating factor.

In some embodiments, compounds disclosed herein are used to treat diffuse parenchymal interstitial lung diseases in mammal: iatrogenic drug induced, occupational/environmental (Farmer lung), granulomatous diseases (sarcoidosis, hypersensitivity pneumonia), collagen vascular disease (scleroderma and others), alveolar proteinosis, langerhans cell granulonmatosis, lymphangioleiomyomatosis, Hermansky-Pudlak Syndrome, Tuberous sclerosis, neurofibromatosis, metabolic storage disorders, familial interstitial lung disease.

In some embodiments, compounds disclosed herein are used to treat post-transplant fibrosis associated with chronic rejection in a mammal: Bronchiolitis obliterans for lung transplant.

In some embodiments, compounds disclosed herein are used to treat cutaneous fibrosis in a mammal: cutaneous scleroderma, Dupuytren disease, keloids.

In one aspect, compounds disclosed herein are used to treat hepatic fibrosis with or without cirrhosis in a mammal: toxic/drug induced (hemochromatosis), alcoholic liver disease, viral hepatitis (hepatitis B virus, hepatitis C virus, HCV), nonalcoholic liver disease (NASH), metabolic and auto-immune.

In one aspect, compounds disclosed herein are used to treat renal fibrosis in a mammal: tubulointerstitium fibrosis, glomerular sclerosis.

In any of the aforementioned aspects involving the treatment of LPA dependent diseases or conditions are further embodiments comprising administering at least one additional agent in addition to the administration of a compound having the structure of Formula (I). In various embodiments, each agent is administered in any order, including simultaneously.

In any of the embodiments disclosed herein, the mammal is a human.

In some embodiments, compounds provided herein are administered to a human. In some embodiments, compounds provided herein are orally administered to a human.

In some embodiments, compounds provided herein are used as antagonists of at least one LPA receptor. In some embodiments, compounds provided herein are used for inhibiting the activity of at least one LPA receptor or for the treatment of a disease or condition that would benefit from inhibition of the activity of at least one LPA receptor. In one aspect, the LPA receptor is $LPA_1$.

In other embodiments, compounds provided herein are used for the formulation of a medicament for the inhibition of $LPA_1$ activity.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description

BRIEF DESCRIPTION OF THE FIGURES

FIG. 1. Illustrative examples of compounds described herein.

FIG. 2. Illustrative examples of compounds described herein.

FIG. 3. Illustrative examples of compounds described herein.

FIG. 4. Illustrative examples of compounds described herein.

FIG. 5. Illustrative examples of compounds described herein.

DETAILED DESCRIPTION OF THE INVENTION

Lysophospholipids (such as lysophosphatidic acid (LPA)) affect fundamental cellular functions that include cellular proliferation, differentiation, survival, migration, adhesion, invasion, and morphogensis. These functions influence many biological processes that include neurogensis, angiogenesis, wound healing, immunity, and carcinogenesis.

LPA acts through sets of specific G protein-coupled receptors (GPCRs) in an autocrine and paracrine fashion. LPA binding to its cognate GPCRs ($LPA_1$, $LPA_2$, $LPA_3$, $LPA_4$, $LPA_5$, $LPA_6$) activates intracellular signaling pathways to produce a variety of biological responses.

LPA has a role as a biological effector molecule, and has a diverse range of physiological actions such as, but not limited to, effects on blood pressure, platelet activation, and smooth muscle contraction, and a variety of cellular effects, which include cell growth, cell rounding, neurite retraction, and actin stress fiber formation and cell migration. The effects of LPA are predominantly receptor mediated.

Activation of the LPA receptors with LPA mediates a range of downstream signaling cascades. The actual pathway and realized end point are dependent on a range of variables that include receptor usage, cell type, expression level of a receptor or signaling protein, and LPA concentration. Nearly all mammalian cells, tissues and organs co-express several LPA-receptor subtypes, which indicates that LPA receptors signal in a cooperative manner $LPA_1$, $LPA_2$, and $LPA_3$ share high amino acid sequence similarity.

LPA regulates many important functions of fibroblasts in wound healing, including proliferation, migration, differentiation and contraction. Fibroblast proliferation is required in wound healing in order to fill an open wound. In contrast, fibrosis is characterized by intense proliferation and accumulation of myofibroblasts that actively synthesize ECM and proinflammatory cytokines. LPA can either increase or suppress the proliferation of cell types important in wound healing.

Tissue injury initiates a complex series of host wound-healing responses; if successful, these responses restore normal tissue structure and function. If not, these responses can lead to tissue fibrosis and loss of function.

A number of muscular dystrophies are characterized by a progressive weakness and wasting of musculature, and by extensive fibrosis. It has been shown that LPA treatment of cultured myoblasts induced significant expression of connective tissue growth factor (CTGF). CTGF subsequently induces collagen, fibronectin and integrin expression and induces dedifferentiation of these myoblasts. Treatment of a variety of cell types with LPA induces reproducible and high level induction of CTGF. CTGF is a profibrotic cytokine, signaling down-stream and in parallel with TGFβ.

LPA and $LPA_1$ play key pathogenic roles in pulmonary fibrosis. Fibroblast chemoattractant activity plays an important role in the lungs in patients with pulmonary fibrosis. Profibrotic effects of $LPA_1$-receptor stimulation is explained by $LPA_1$-receptor-mediated vascular leakage and increased fibroblast recruitment, both profibrotic events. The LPA-$LPA_1$ pathway has a role in mediating fibroblast migration and vascular leakage in IPF. The end result is the aberrant healing process that characterises this fibrotic condition.

The LPA-LPA2 pathway contributes to the activation of the TGF-β pathway in pulmonary fibrosis. In some embodiments, compounds that inhibit LPA2 show efficacy in the treatment of lung fibrosis. In some embodiments, compounds that inhibit both LPA1 and LPA2 show improved efficacy in the treatment of lung fibrosis compared to compounds which inhibit only LPA1 or LPA2.

LPA and $LPA_1$ are involved in the etiology of kidney fibrosis. In mice invalidated for the $LPA_1$ receptor ($LPA_1$ (−/−), the development of renal fibrosis was significantly attenuated. Unilateral ureteral obstruction (UUO; animal model of renal fibrosis) mice treated with the LPA receptor antagonist Ki16425 closely resembled the $LPA_1$ (−/−) mice.

LPA is implicated in liver disease and fibrosis. Plasma LPA levels and serum autotoxin are elevated in hepatitis patients and animal models of liver injury in correlation with increased fibrosis. LPA also regulates liver cell function. $LPA_1$ and $LPA_2$ receptors are expressed by mouse hepatic stellate cells and LPA stimulates migration of hepatic myofibroblasts.

LPA is in involved in wound healing in the eye. $LPA_1$ and $LPA_3$ receptors are detectable in the normal rabbit corneal epithelial cells, keratocytes and endothelial cells and $LPA_1$ and $LPA_3$ expression are increased in corneal epithelial cells following injury.

LPA is present in the aqueous humor and the lacrimal gland fluid of the rabbit eye and these levels are increased in a rabbit corneal injury model.

LPA induces actin stress fiber formation in rabbit corneal endothelial and epithelial cells and promotes contraction corneal fibroblasts. LPA also stimulates proliferation of human retinal pigmented epithelial cells.

LPA is implicated in myocardial infarction and cardiac fibrosis. Serum LPA levels are increased in patients following mycocardial infarction (MI) and LPA stimulates proliferation and collagen production (fibrosis) by rat cardiac fibroblasts. Both LPA1 and LPA3 receptors are highly expressed in human heart tissue.

In one aspect, compounds of Formula (I) are used to treat or prevent fibrosis in a mammal. In one aspect, compounds of Formula (I) are used to treat or prevent fibrosis of an organ or tissue in a mammal.

The terms "fibrosis" or "fibrosing disorder," as used herein, refers to conditions that are associated with the abnormal accumulation of cells and/or fibronectin and/or collagen and/ or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract.

Exemplary diseases, disorders, or conditions that involve fibrosis include, but are not limited to: Lung diseases associated with fibrosis, e.g., idiopathic pulmonary fibrosis, pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), scleroderma, chronic asthma, silicosis, asbestos induced pulmonary or pleural fibrosis, acute lung injury and acute respiratory distress (including bacterial pneumonia induced, trauma induced, viral pneumonia induced, ventilator induced, non-pulmonary sepsis induced, and aspiration induced); Chronic nephropathies associated with injury/fibrosis (kidney fibrosis), e.g., glomerulonephritis secondary to systemic inflammatory diseases such as lupus and scleroderma, diabetes, glomerular nephritis, focal segmental glomerular sclerosis, IgA nephropathy, hypertension, allograft and Alport; Gut fibrosis, e.g., scleroderma, and radiation induced gut fibrosis; Liver fibrosis, e.g., cirrhosis, alcohol induced liver fibrosis, nonalcoholic steatohepatitis (NASH), biliary duct injury, primary biliary cirrhosis, infection or viral induced liver fibrosis (e.g., chronic HCV infection), and autoimmune hepatitis; Head and neck fibrosis, e.g., radiation induced; Corneal scarring, e.g., LASIK (laser-assisted in situ keratomileusis), corneal transplant, and trabeculectomy; Hypertrophic scarring and keloids, e.g., burn induced or surgical; and other fibrotic diseases, e.g., sarcoidosis, scleroderma, spinal cord injury/ fibrosis, myelofibrosis, vascular restenosis, atherosclerosis, arteriosclerosis, Wegener's granulomatosis, mixed connective tissue disease, and Peyronie's disease.

In one aspect, a mammal suffering from one of the following non-limiting exemplary diseases, disorders, or conditions will benefit from therapy with a compound of Formula (I): atherosclerosis, thrombosis, heart disease, vasculitis, formation of scar tissue, restenosis, phlobitis, COPD (chronic obstructive pulmonary disease), pulmonary hypertension, pulmonary fibrosis, pulmonary inflammation, bowel adhesions, bladder fibrosis and cystitis, fibrosis of the nasal passages, sinusitis, inflammation mediated by neutrophils, and fibrosis mediated by fibroblasts.

In one aspect, compounds of Formula (I) are used to treat a dermatological disorders in a mammal. Dermatological disorders include, but are not limited to, proliferative or inflammatory disorders of the skin such as, atopic dermatitis, bullous disorders, collagenoses, psoriasis, psoriatic lesions, dermatitis, contact dermatitis, eczema, urticaria, rosacea, wound healing, scarring, hypertrophic scarring, keloids, Kawasaki Disease, rosacea, Sjogren-Larsso Syndrome, urticaria.

LPA is released following tissue injury. $LPA_1$ plays a role in the initiation of neuropathic pain. In one aspect, compounds of Formula (I) are used in the treatment of pain in a mammal. In one aspect, the pain is acute pain or chronic pain. In another aspect, the pain is neuropathic pain. In another aspect, the pain is cancer pain. In one aspect, compounds of Formula (I) are used in the treatment of fibromylagia.

Lysophospholipid receptor signaling plays a role in the etiology of cancer. Lysophosphatidic acid (LPA) and its G protein-coupled receptors (GPCRs) $LPA_1$, $LPA_2$, and/or $LPA_3$ play a role in the development of several types of cancers.

LPA contributes to tumorigenesis by increasing motility and invasiveness of cells. LPA has been implicated in the initiation or progression of ovarian cancer. LPA is present at significant concentrations (2-80 μM) in the ascitic fluid of ovarian cancer patients. LPA receptors (LPA2 and LPA3) are also overexpressed in ovarian cancer cells as compared to normal ovarian surface epithelial cells. LPA has also been implicated in the initiation or progression of prostate cancer, breast cancer, melanoma, head and neck cancer, bowel cancer (colorectal cancer), thyroid cancer, glioblastoma, and other cancers.

LPA receptors mediate both migration of and invasion by pancreatic cancer cell lines: Ki16425 and $LPA_1$-specific siRNA effectively blocked in vitro migration in response to LPA and peritoneal fluid (ascites) from pancreatic cancer patients; in addition, Ki16425 blocked the LPA-induced and ascites-induced invasion activity of a highly peritoneal metastatic pancreatic cancer cell line (Yamada et al, *J. Biol. Chem.*, 279, 6595-6605, 2004).

Colorectal carcinoma cell lines show significant expression of $LPA_1$ mRNA and respond to LPA by cell migration and production of angiogenic factors. Overexpression of LPA receptors has a role in the pathogenesis of thyroid cancer. $LPA_3$ was originally cloned from prostate cancer cells, concordant with the ability of LPA to induce autocrine proliferation of prostate cancer cells.

LPA has stimulatory roles in cancer progression in many types of cancer. LPA is produced from and induces proliferation of prostate cancer cell lines. LPA induces human colon carcinoma DLD1 cell proliferation, migration, adhesion, and secretion of angiogenic factors through $LPA_1$ signalling. In other human colon carcinoma cells lines (HT29 and WiDR), LPA enhances cell proliferation and secretion of angiogenic factors. In other colon cancer cell lines, $LPA_2$ and $LPA_3$ receptor activation results in proliferation of the cells. $LPA_1$ is implicated in bone metastasis (Boucharaba et al., *Proc. Natl. Acad. Sci. USA*, 103, 9643-9648, 2006).

In one aspect, a compound of Formula (I) is used in the treatment of cancer. In one aspect, compounds of Formula (I) are used in the treatment of malignant and benign proliferative disease. In one aspect, compounds of Formula (I) are used to prevent or reduce proliferation of tumor cells, invasion and metastasis of carcinomas, pleural mesothelioma or peritoneal mesothelioma, cancer pain, bone metastases. In one aspect is a method of treating cancer in a mammal, the method comprising administering to the mammal a compound of Formula (I) and a second therapeutic agent, wherein the second therapeutic agent is an anti-cancer agent. In some embodiments, radiation therapy is also used.

The types of cancer include, but are not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma or basal cell cancer) or hematological tumors (such as the leukemias) at any stage of the disease with or without metastases.

In one aspect, LPA is a contributor to the pathogenesis of respiratory diseases. Proinflammatory effects of LPA include degranulation of mast cells, contraction of smooth-muscle cells and release of cytokines from dendritic cells. LPA induces the secretion of IL-8 from human bronchial epithelial cells. IL-8 is found in increased concentrations in BAL fluids from patients with asthma, chronic obstructive lung disease, pulmonary sarcoidosis and acute respiratory distress syndrome and Il-8 has been shown to exacerbate airway inflammation and airway remodeling of asthmatics. LPA1, LPA2 and LPA3 receptors have all been shown to contribute to the LPA-induced IL-8 production.

Administration of LPA in vivo induces airway hyper-responsiveness, itch-scratch responses, infiltration and activation of eosinophils and neutrophils, vascular remodeling, and nociceptive flexor responses. LPA also induces histamine release from mouse and rat mast cells. In one aspect, the effects of LPA are mediated through $LPA_1$ and/or $LPA_3$. In one aspect, compounds of Formula (I) are used in the treatment of various allergic disorders in a mammal. In one aspect, compounds of Formula (I) are used in the treatment of respiratory diseases, disorders or conditions in a mammal. In one aspect, compounds of Formula (I) are used in the treatment of asthma in a mammal. In one aspect, compounds of Formula (I) are used in the treatment of chronic asthma in a mammal.

The term "respiratory disease," as used herein, refers to diseases affecting the organs that are involved in breathing, such as the nose, throat, larynx, eustachian tubes, trachea, bronchi, lungs, related muscles (e.g., diaphram and intercostals), and nerves. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

In one aspect, presented herein is the use of compounds of Formula (I) in the treatment or prevention of chronic obstructive pulmonary disease in a mammal comprising administering to the mammal at least once an effective amount of at least one compound of Formula (I). In addition, chronic obstructive pulmonary disease includes, but is not limited to, chronic bronchitis or emphysema, pulmonary hypertension, interstitial lung fibrosis and/or airway inflammation, and cystic fibrosis.

The nervous system is a major locus for $LPA_1$ expression. In one aspect, provided is a compound of Formula (I) for use in the treatment or prevention of a nervous system disorder in a mammal. The term "nervous system disorder," as used herein includes, but is not limited to, Alzheimer's Disease, cerebral edema, cerebral ischemia, stroke, multiple sclerosis, neuropathies, Parkinson's Disease, multiple sclerosis, retinal ischemia, post-surgical cognitive dysfunction, migraine, peripheral neuropathy/neuropathic pain, spinal cord injury, cerebral edema and head injury.

Angiogenesis, the formation of new capillary networks from pre-existing vasculature, is normally invoked in wound healing, tissue growth and myocardial angiogenesis after ischemic injury. Peptide growth factors and lysophospholipids control coordinated proliferation, migration, adhesion, differentiation and assembly of vascular endothelial cells (VECs) and surrounding vascular smooth-muscle cells (VSMCs). In one aspect, dysregulation of the processes mediating angiogenesis leads to atherosclerosis, hypertension, tumor growth, rheumatoid arthritis and diabetic retinopathy.

In one aspect, compounds of Formula (I) are used to treat or prevent cardiovascular disease in mammal, including but not limited to: arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

In one aspect, provided herein are methods for preventing or treating vasoconstriction, atherosclerosis and its sequelae myocardial ischemia, myocardial infarction, aortic aneurysm, vasculitis and stroke comprising administering at least once to the mammal an effective amount of at least one compound of Formula (I) or pharmaceutical composition or medicament which includes a compound of Formula (I). In some embodiments, provided herein are methods for preventing or treating Raynaud's phenomenon.

In one aspect, provided herein are methods for reducing cardiac reperfusion injury following myocardial ischemia and/or endotoxic shock comprising administering at least once to the mammal an effective amount of at least one compound of Formula (I).

In one aspect, provided herein are methods for reducing the constriction of blood vessels in a mammal comprising administering at least once to the mammal an effective amount of at least one compound of Formula (I).

In one aspect, provided herein are methods for lowering or preventing an increase in blood pressure of a mammal comprising administering at least once to the mammal an effective amount of at least one compound of Formula (I).

LPA is associated with various inflammatory/immune diseases. In one aspect, compounds of Formula (I) are used to treat or prevent inflammation in a mammal. In one aspect, antagonists of LPA$_1$ and/or LPA$_3$ find use in the treatment or prevention of inflammatory/immune disorders in a mammal.

Examples of inflammatory/immune disorders include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

In accordance with one aspect, are methods for treating, preventing, reversing, halting or slowing the progression of LPA-dependent or LPA-mediated diseases or conditions once it becomes clinically evident, or treating the symptoms associated with or related to LPA-dependent or LPA-mediated diseases or conditions, by administering to the mammal a compound of Formula (I). In certain embodiments, the subject already has a LPA-dependent or LPA-mediated disease or condition at the time of administration, or is at risk of developing a LPA-dependent or LPA-mediated disease or condition.

In certain aspects, are methods for preventing or treating eosinophil and/or basophil and/or dendritic cell and/or neutrophil and/or monocyte and/or T-cell recruitment comprising administering at least once to the mammal an effective amount of at least one compound of Formula (I).

In certain aspects, are methods for the treatment of cystitis, including, e.g., interstitial cystitis, comprising administering at least once to the mammal a therapeutically effective amount of at least one compound of Formula (I).

In accordance with one aspect, methods described herein include the diagnosis or determination of whether or not a patient is suffering from a LPA-dependent or LPA-mediated disease or condition by administering to the subject a therapeutically effective amount of a compound of Formula (I) and determining whether or not the patient responds to the treatment.

In one aspect provided herein are compounds of Formula (I), pharmaceutically acceptable salts, pharmaceutically acceptable prodrugs, and pharmaceutically acceptable solvates thereof, which are antagonists of at least one LPA receptor (e.g. LPA$_1$, LPA$_2$, LPA$_3$) and are used to treat patients suffering from one or more LPA-dependent or LPA-mediated conditions or diseases, including, but not limited to, lung fibrosis, kidney fibrosis, liver fibrosis, scarring, asthma, rhinitis, chronic obstructive pulmonary disease, pulmonary hypertension, interstitial lung fibrosis, arthritis, allergy, psoriasis, inflammatory bowel disease, adult respiratory distress syndrome, myocardial infarction, aneurysm, stroke, cancer, pain, proliferative disorders and inflammatory conditions. In some embodiments, LPA-dependent conditions or diseases include those wherein an absolute or relative excess of LPA is present and/or observed.

In any of the aforementioned aspects the LPA-dependent or LPA-mediated diseases or conditions include, but are not limited to, organ fibrosis, asthma, allergic disorders, chronic obstructive pulmonary disease, pulmonary hypertension, lung or pleural fibrosis, peritoneal fibrosis, arthritis, allergy, cancer, cardiovascular disease, adult respiratory distress syndrome, myocardial infarction, aneurysm, stroke, and cancer.

In one aspect, compounds of Formula (I) are used to improve the corneal sensitivity decrease caused by corneal operations such as laser-assisted in situ keratomileusis (LASIK) or cataract operation, corneal sensitivity decrease caused by corneal degeneration, and dry eye symptom caused thereby.

In one aspect, presented herein is the use of compounds of Formula (I) in the treatment or prevention of ocular inflammation and allergic conjunctivitis, vernal keratoconjunctivitis, and papillary conjunctivitis in a mammal comprising administering at least once to the mammal an effective amount of at least one compound of Formula (I).

In one aspect, presented herein is the use of compounds of Formula (I) in the treatment or prevention of Sjogren disease or inflammatory disease with dry eyes in a mammal comprising administering at least once to the mammal an effective amount of at least one compound of Formula (I).

In one aspect, LPA and LPA receptors (e.g. LPA$_1$) are involved in the pathogenesis of osteoarthritis. In one aspect, presented herein is the use of compounds of Formula (I) in the treatment or prevention of osteoarthritis in a mammal comprising administering at least once to the mammal an effective amount of at least one compound of Formula (I).

In one aspect, LPA receptors (e.g. LPA$_1$, LPA$_3$) contribute to the pathogenesis of rheumatoid arthritis. In one aspect, presented herein is the use of compounds of Formula (I) in the treatment or prevention of rheumatoid arthritis in a mammal comprising administering at least once to the mammal an effective amount of at least one compound of Formula (I).

In one aspect, LPA receptors (e.g. LPA$_1$) contribute to adipogenesis. In one aspect, presented herein is the use of compounds of Formula (I) in the promotion of adipose tissue formation in a mammal comprising administering at least once to the mammal an effective amount of at least one compound of Formula (I).

Compounds

In one aspect, provided herein is a compound having the structure of Formula (I) or a pharmaceutically acceptable salt thereof:

Formula (I)

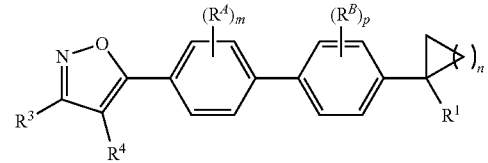

wherein
R¹ is —CO₂H, —CO₂R^D, —CN, —C(=O)N(R⁹)₂, —C(=O)NHCH₂CH₂SO₃H, —C(=O)NHSO₂R¹⁰, tetrazolyl, or 5-oxo-2,5-dihydro-[1,2,4]oxadiazol-3-yl;
R^D is H or C₁-C₄alkyl;
R³ is H, C₁-C₄alkyl, C₃-C₆cycloalkyl, or C₁-C₄fluoroalkyl;
R⁴ is —NR⁷C(=O)OCH(R⁸)—CY;
R⁷ is H or C₁-C₄alkyl;
R⁸ is H, C₁-C₄alkyl, or C₁-C₄fluoroalkyl;
CY is a substituted or unsubstituted C₃-C₆cycloalkyl or a substituted or unsubstituted phenyl, wherein if CY is substituted then CY is substituted with 1 or 2 R^C;
R⁹ is H, C₁-C₆alkyl, C₁-C₆fluoroalkyl, C₃-C₆cycloalkyl, or a substituted or unsubstituted phenyl;
R¹⁰ is a C₁-C₆alkyl, C₁-C₆fluoroalkyl, C₃-C₆cycloalkyl, or a substituted or unsubstituted phenyl;
each of R^A, R^B, and R^C are independently selected from F, Cl, Br, I, —CN, —OH, C₁-C₄alkyl, C₁-C₄fluoroalkyl, C₁-C₄fluoroalkoxy, C₁-C₄alkoxy, and C₁-C₄heteroalkyl;
m is 0, 1, or 2; n is 1, 2, 3 or 4; p is 0, 1, or 2.

For any and all of the embodiments, substituents are selected from among from a subset of the listed alternatives. For example, in some embodiments, R¹ is —CO₂H or —CO₂(R^D). In some embodiments, R^D is H, —CH₃, or —CH₂CH₃. In some embodiments, R¹ is —CO₂H. In some embodiments, R¹ is —C(=O)NHSO₂R¹⁰. In some embodiments, R¹ is a carboxylic acid bioisostere.

In some embodiments, R³ is H or C₁-C₄alkyl. In some embodiments, R³ is C₁-C₄alkyl. In some embodiments, R³ is H, —CH₃, or —CH₂CH₃. In some embodiments, R³ is —CH₃, or —CH₂CH₃. In some embodiments, R³ is —CH₃. In some embodiments, R³ is H.

In some embodiments, R⁷ is H.

In some embodiments, R⁸ is H, C₁-C₄alkyl, or C₁-C₄fluoroalkyl. In some embodiments, R⁸ is H. In some embodiments, R⁸ is H or C₁-C₄alkyl. In some embodiments, R⁸ is H, —CH₃, or —CF₃. In some embodiments, R⁸ is —CH₃. In some embodiments, R⁸ is —CH₂CH₃.

In some embodiments, R¹ is —CO₂H, —CO₂R^D, —C(=O)NHSO₂R¹⁰, tetrazolyl, or 5-oxo-2,5-dihydro-[1,2,4]oxadiazol-3-yl. In some embodiments, R¹ is —CO₂H, —CO₂R^D, —C(=O)NHSO₂R¹⁰ or tetrazolyl. In some embodiments, R¹ is —CO₂H, —CO₂R^D, —C(=O)NHSO₂R¹⁰ or tetrazolyl; R³ is C₁-C₄alkyl; R⁷ is H; R⁸ is H, —CH₃ or —CF₃; R¹⁰ is a C₁-C₆alkyl or a substituted or unsubstituted phenyl; each R^A is independently selected from F, Cl, Br, I, —OH, —CH₃, —CF₃, —OCF₃, and —OCH₃; each R^B is independently selected from F, Cl, Br, I, —OH, —CH₃, —CF₃, —OCF₃, and —OCH₃; each R^C is independently selected from F, Cl, Br, I, —OH, —CH₃, —CF₃, —OCF₃, and —OCH₃; m is 0 or 1; n is 1, 2, or 3; p is 0 or 1.

In some embodiments, R¹ is —CO₂H or —CO₂R^D; R^D is H, —CH₃, or —CH₂CH₃; R³ is —CH₃ or —CH₂CH₃; R⁴ is —NHC(=O)OCH(R⁸)—CY; R⁸ is H, or —CH₃; CY is a substituted or unsubstituted phenyl, wherein if CY is a substituted phenyl then the phenyl is substituted with 1 or 2 R^C.

In some embodiments, the compound of Formula (I) has the following structure:

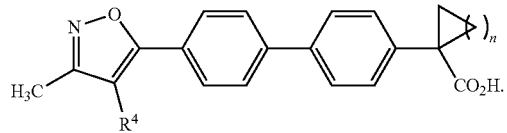

In some embodiments, the compound of Formula (I) has the following structure:

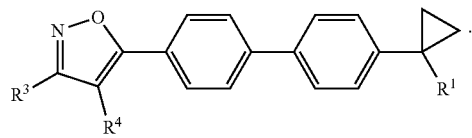

In some embodiments, R¹ is —C(=O)NHSO₂R¹⁰; R³ is —CH₃ or —CH₂CH₃; R⁸ is H, or —CH₃; R¹⁰ is —CH₃, or —CH₂CH₃.

In some embodiments, R⁴ is —NHC(=O)OCH(CH₃)-(substituted or unsubstituted phenyl); wherein if the phenyl is substituted then the phenyl is substituted with R^C; R^C is F, Cl, —CH₃, or CF₃; n is 1.

In some embodiments, R⁴ is

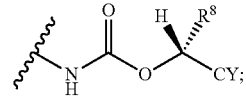

R⁸ is —CH₃; CY is a substituted or unsubstituted phenyl, wherein if CY is substituted phenyl then the phenyl is substituted with 1 or 2 R^C, R^C is F, Cl, —OH, —CH₃, —CF₃, or —OCH₃; n is 1. In some embodiments, CY is an unsubstituted phenyl.

In some embodiments, CY is cyclopropyl, cyclobutyl, cyclohexyl, 2-chlorocyclohex-1-enyl, phenyl, 2-fluorophenyl, 2,3-difluorophenyl, 2,4-difluorophenyl, 2,5-difluorophenyl, 2,6-difluorophenyl, 2-chlorophenyl, 2,6-dichlorophenyl, 2-bromophenyl, 3-bromophenyl, 2,4-dichlorophenyl, 2-methoxyphenyl, 3-methoxyphenyl, 4-methoxyphenyl, 2-trifluoromethylphenyl, 3-trifluoromethylphenyl, 4-trifluoromethylphenyl, 2-fluoro-4-methoxyphenyl, 2-methylphenyl, 3-methylphenyl, 4-methylphenyl, 2-cyanophenyl, 3-cyanophenyl, or 4-cyanophenyl.

In some embodiments, CY is cyclopropyl, cyclobutyl, cyclopentyl, cyclopent-1-enyl, 2-chlorocyclopent-1-enyl, cyclohexyl, cyclohex-1-enyl, 2-chlorocyclohex-1-enyl, phenyl, 2-fluorophenyl, 2,3-difluorophenyl, 2,4-difluorophenyl, 2,5-difluorophenyl, 2,6-difluorophenyl, 2-chlorophenyl, 2,6-dichlorophenyl, 2-bromophenyl, 3-bromophenyl, 2,4-dichlorophenyl, 2-hydroxyphenyl, 3-hydroxyphenyl, 4-hydroxyphenyl, 2-methoxyphenyl, 3-methoxyphenyl, 4-methoxyphenyl, 2-trifluoromethylphenyl, 3-trifluoromethylphenyl, 4-trifluoromethylphenyl, 2-fluoro-4-methoxyphenyl, 2-methylphenyl, 3-methylphenyl, 4-methylphenyl, 2-cyanophenyl, 3-cyanophenyl, or 4-cyanophenyl.

In some embodiments, CY is phenyl, 2-fluorophenyl, 2,3-difluorophenyl, 2,4-difluorophenyl, 2,5-difluorophenyl, 2,6-difluorophenyl, 2-chlorophenyl, 2,6-dichlorophenyl, 2,4-dichlorophenyl, 2-hydroxyphenyl, 3-hydroxyphenyl, 4-hydroxyphenyl, 2-methoxyphenyl, 3-methoxyphenyl, 4-methoxyphenyl, 2-trifluoromethylphenyl, 3-trifluoromethylphenyl, 4-trifluoromethylphenyl, 2-fluoro-4-methoxyphenyl, 2-methylphenyl, 3-methylphenyl, or 4-methylphenyl.

In some embodiments, CY is phenyl, 2-fluorophenyl, 3-fluorophenyl, 2-chlorophenyl, 3-chlorophenyl, 2-methylphenyl, 3-methylphenyl, 2-trifluoromethylphenyl, or 3-trifluoromethylphenyl. In some embodiments, CY is phenyl. In some embodiments, CY is phenyl, 2-hydroxyphenyl, 3-hydroxyphenyl, or 4-hydroxyphenyl.

In some embodiments, the compound of Formula (I) has the following structure:

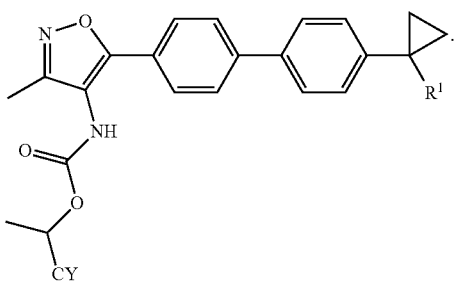

In some embodiments, the compound of Formula (I) has one of the following structure:

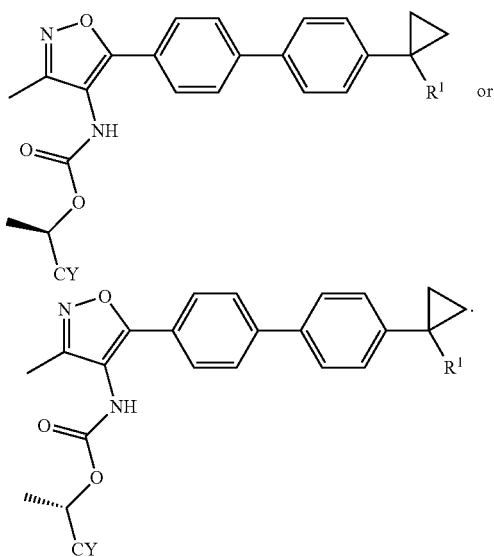

In some embodiments, $R^1$ is —CO$_2$H; CY is phenyl, 2-fluorophenyl, 3-fluorophenyl, 2-chlorophenyl, 3-chlorophenyl, 2-methylphenyl, 3-methylphenyl, 2-trifluoromethylphenyl, or 3-trifluoromethylphenyl.

In some embodiments, CY is $C_3$-$C_6$cycloalkyl, substituted or unsubstituted phenyl; wherein if CY is substituted then CY is substituted with $R^C$; $R^C$ is F, Cl, —CH$_3$, or CF$_3$. In some embodiments, CY is $C_3$-$C_6$cycloalkyl.

In some embodiments, $R^4$ is —NHC(=O)OCH($R^8$)—CY. In some embodiments, $R^4$ is —NHC(=O)OCH$_2$-(cyclopropyl), —NHC(=O)OCH(CH$_3$)-(cyclopropyl), —NHC(=O)OCH$_2$-(substituted or unsubstituted phenyl) or —NHC(=O)OCH(CH$_3$)-(substituted or unsubstituted phenyl); wherein if CY is substituted then CY is substituted with $R^C$; $R^C$ is F, Cl, —CH$_3$, or CF$_3$. In some embodiments, $R^4$ is —NHC(=O)OCH(CH$_3$)-(cyclopropyl). In some embodiments, $R^4$ is —NHC(=O)OCH(CH$_3$)-(phenyl).

In some embodiments, CY is cyclopropyl, cyclobutyl, cyclopentyl, cyclohexyl, a substituted or unsubstituted pentenyl, a substituted or unsubstituted cyclohexenyl, or a substituted or unsubstituted phenyl; wherein if CY is substituted then CY is substituted with $R^C$; $R^C$ is F, Cl, —CH$_3$, or CF$_3$. In some embodiments, CY is a substituted or unsubstituted phenyl; wherein if CY is a substituted phenyl then the substituted phenyl is substituted with $R^C$; $R^C$ is F, Cl, —CH$_3$, or CF$_3$. In some embodiments, CY is cyclopropyl. In some embodiments, CY is phenyl.

In some embodiments, CY is a substituted or unsubstituted phenyl, wherein if CY is substituted then each substituent on CY is H or $R^C$; each $R^C$ is independently selected from H, halogen, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl. In some embodiments, each $R^C$ is independently selected from H, F, Cl, —CH$_3$, —CF$_3$, —OCF$_3$, —OCH$_3$. In some embodiments, CY is phenyl, 2-fluorophenyl or 2-chloro-phenyl. In some embodiments, CY is phenyl. In some embodiments, $R^C$ is H, F, Cl, —CH$_3$, or CF$_3$.

In some embodiments, CY is unsubstituted or monosubstituted with $R^C$.

In some embodiments, $R^4$ is

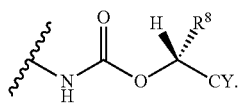

In some embodiments, $R^4$ is

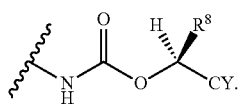

In some embodiments, $R^8$ is —CH$_3$ or —CF$_3$. In some embodiments, $R^8$ is —CH$_3$.

In some embodiments, $R^4$ is

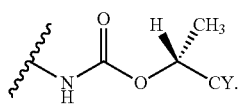

In some embodiments, $R^4$ is

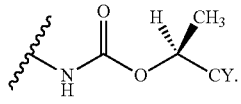

In some embodiments, $R^4$ is

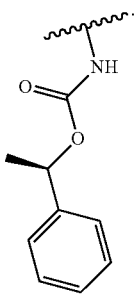

In some embodiments, $R^4$ is

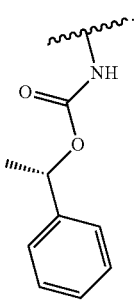

In some embodiments, $R^{10}$ is a $C_1$-$C_6$alkyl or a substituted or unsubstituted phenyl. In some embodiments, $R^{10}$ is a $C_1$-$C_6$alkyl. In some embodiments, $R^{10}$ is —$CH_3$ or —$CH_2CH_3$. In some embodiments, $R^{10}$ is a substituted or unsubstituted phenyl. In some embodiments, $R^{10}$ is a phenyl. In some embodiments, $R^{10}$ is a $C_1$-$C_4$alkyl or a phenyl.

In some embodiments, each $R^A$ is independently selected from F, Cl, Br, I, —$CH_3$, —$CF_3$, —OH, —$OCF_3$, and —$OCH_3$. In some embodiments, each $R^A$ is independently selected from F, Cl, —$CH_3$, —$CF_3$, —OH, —$OCF_3$, and —$OCH_3$. In some embodiments, each $R^A$ is independently selected from F, Cl, —$CH_3$, —$CF_3$, and —OH. In some embodiments, each $R^A$ is independently selected from F, Cl, —$CH_3$, and —OH.

In some embodiments, each $R^B$ is independently selected from F, Cl, Br, I, —$CH_3$, —$CF_3$, —OH, —$OCF_3$, and —$OCH_3$. In some embodiments, each $R^B$ is independently selected from F, Cl, —$CH_3$, —$CF_3$, and —OH. In some embodiments, each $R^B$ is independently selected from F, Cl, —$CH_3$, and —OH.

In some embodiments, each $R^C$ is independently selected from F, Cl, Br, I, —$CH_3$, —$CF_3$, —OH, —$OCF_3$, and —$OCH_3$. In some embodiments, each $R^C$ is independently selected from F, Cl, —$CH_3$, —$CF_3$, —OH, —$OCF_3$, and —$OCH_3$. In some embodiments, each $R^C$ is independently selected from F, Cl, —$CH_3$, —$CF_3$, and —OH. In some embodiments, each $R^C$ is independently selected from F, Cl, —$CH_3$, and —$CF_3$. In some embodiments, each $R^C$ is independently selected from F, Cl, and —OH. In some embodiments, each $R^C$ is independently selected from F, and Cl.

In some embodiments, m is 0 or 1. In some embodiments, m is 0. In some embodiments, m is 1. In some embodiments, p is 0 or 1. In some embodiments, p is 0. In some embodiments, p is 1.

In some embodiments, n is 1, 2, 3 or 4. In some embodiments, n is 1, 2 or 3. In some embodiments, n is 1. In some embodiments, n is 2. In some embodiments, n is 3. In some embodiments, n is 4.

In some embodiments, the compound of Formula (I) has one of the following structures:

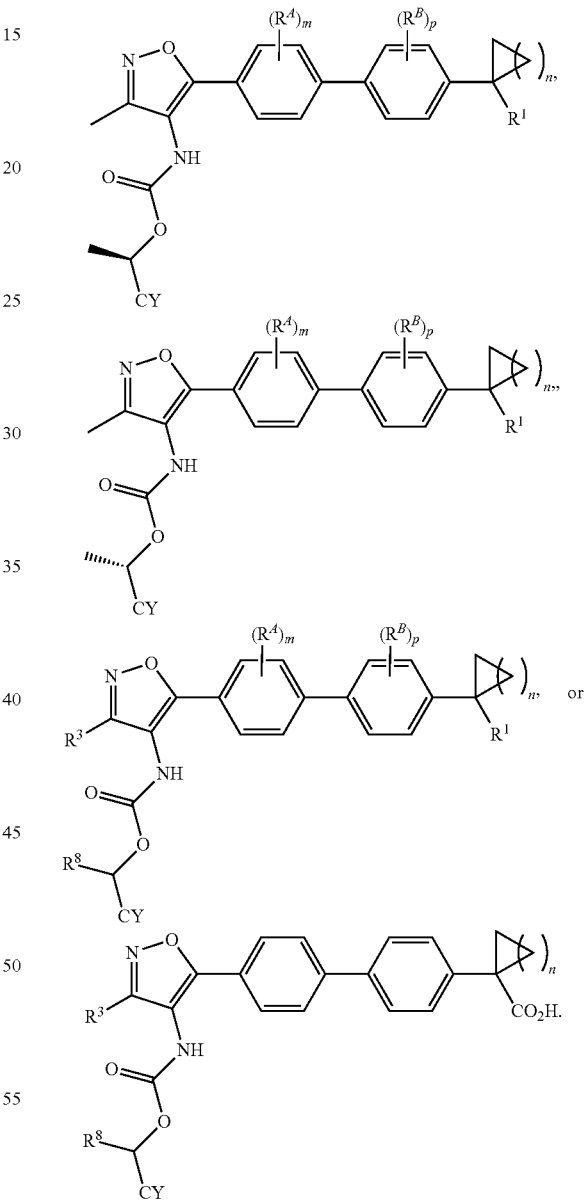

In some embodiments, $R^1$ is —$CO_2H$; m is 0; p is 0, n is 1; CY is phenyl. In some embodiments, $R^8$ is —$CH_3$; n is 1; CY is phenyl.

In some embodiments, CY is as described in Table 1 and/or Table 2.

Any combination of the groups described above for the various variables is contemplated herein. Throughout the specification, groups and substituents thereof are chosen by one skilled in the field to provide stable moieties and compounds.

In some embodiments, compounds of Formula (I) include, but are not limited to, those described in Table 1, Table 2 and FIGS. 1 to 5.

TABLE 1

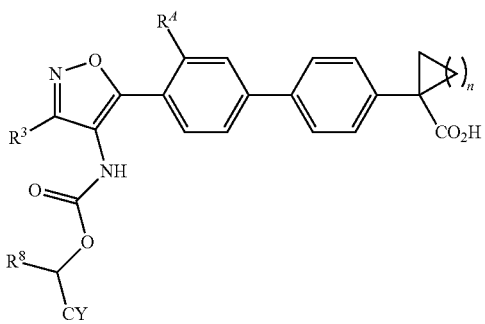

| Cmpd # | $R^3$ | $R^8$ | n | $R^A$ | CY | M + H* |
|---|---|---|---|---|---|---|
| 1 | —CH₃ | (R)-CH₃ | 1 | H | Phenyl | 483 |
| 2 | —CH₃ | —CH₃ | 1 | H | Cyclohexyl | 489 |
| 3 | —CH₃ | (R)-CH₃ | 1 | H | 2-Methyl-phenyl | 497 |
| 4 | —CH₃ | H | 1 | H | Phenyl | 469 |
| 5 | —CH₃ | (S)-CH₃ | 1 | H | Cyclopropyl | 447 |
| 6 | —CH₃ | (R)-CH₃ | 1 | H | Cyclopropyl | 447 |
| 7 | —CH₃ | H | 1 | H | Cyclopropyl | 433 |
| 8 | —CH₃ | (R)-CH₃ | 1 | H | 2-Chloro-phenyl | 517 |
| 9 | —CH₃ | (R)-CH₃ | 1 | H | 2-Trifluoromethyl-phenyl | 551 |
| 10 | —CH₃ | (R)-CH₃ | 2 | H | Phenyl | 497 |
| 11 | —CH₃ | (R)-CH₃ | 3 | H | Phenyl | 511 |
| 12 | —CH₃ | —CH₃ | 1 | H | 2-Methoxy-phenyl | 513 |
| 13# | —CH₃ | —CH₃ | 1 | H | 4-Trifluoromethyl-phenyl | 551 |
| 14# | —CH₃ | —CH₃ | 1 | H | 4-Trifluoromethyl-phenyl | 551 |
| 15 | —CH₃ | —CH₃ | 1 | H | 3-Cyano-phenyl | 508 |
| 16 | —CH₃ | (R)-CH₃ | 1 | H | 4-Methyl-phenyl | 497 |
| 17 | —CH₃ | (R)-CH₃ | 1 | H | 3-Methyl-phenyl | 497 |
| 18 | —CH₃ | (R)-CH₃ | 1 | H | 4-Cyano-phenyl | 508 |
| 19 | —CH₃ | (R)-CH₃ | 1 | H | 2-Cyano-phenyl | 508 |
| 20 | —CH₃ | (R)-CH₃ | 1 | H | Cyclobutyl | 461 |
| 21 | —CH₃ | —CH₃ | 1 | H | 2-Chloro-cyclohexenyl | 496 |
| 22 | —CH₃ | (R)-CH₃ | 1 | H | 3-Trifluoromethyl-phenyl | 551 |
| 23 | —CH₃ | (R)-CH₃ | 1 | H | 3-Methoxy-phenyl | 513 |
| 24 | —CH₃ | (R)-CH₃ | 1 | H | 4-Methoxy-phenyl | 513 |
| 25 | —CH₃ | —CH₃ | 1 | H | 3-Bromo-phenyl | 561 |
| 26 | —CH₃ | —CH₃ | 1 | H | 3-Chloro-phenyl | 517 |
| 27 | —CH₃ | (S)-CH₃ | 1 | H | Phenyl | 483 |
| 28 | CH₃ | —CH₃ | 1 | H | 3-Hydroxy-phenyl | 499 |
| 29 | —CH₂CH₃ | (R)-CH₃ | 1 | H | Phenyl | 497 |
| 30 | —CH₂CH₃ | (R)-CH₃ | 1 | H | 3-Trifluoromethyl-phenyl | 565 |
| 31 | —CH₃ | (R)-CH₃ | 1 | —OCH₃ | 3-Trifluoromethyl-phenyl | 581 |
| 32 | —CH₃ | (R)-CH₃ | 1 | H | 3,5-Dibromo-phenyl | 614 |
| 33 | H | (R)-CH₃ | 1 | H | Phenyl | 469 |
| 34 | —CH₃ | —CH₃ | 1 | H | Phenyl | 483 | represent individual stereoisomers; absolute configuration not determined
*mass spectrometric data

TABLE 2

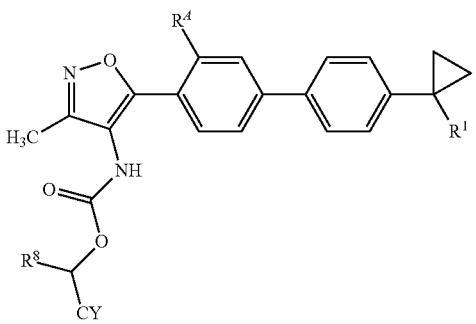

| Cmpd # | $R^A$ | $R^1$ | CY | $R^8$ | M + H* |
|---|---|---|---|---|---|
| 35 | H | —C(=O)NH—S(=O)₂—CH₃ | Phenyl | (R)-CH₃ | 560 |
| 36 | H | —C(=O)NH—S(=O)₂-Phenyl | Phenyl | (R)-CH₃ | 622 |
| 37 | H | CN | Phenyl | (R)-CH₃ | 464 |
| 38 | H | 5-Oxo-2,5-dihydro-[1,2,4]oxadiazol-3-yl | Phenyl | (R)-CH₃ | 523 |
| 39 | H | 1H-Tetrazol-5-yl | Phenyl | (R)-CH₃ | 507 |
| 40 | H | —C(=O)NH—S(=O)₂—CH₃ | 3-Trifluoromethyl-phenyl | (R)-CH₃ | 628 |
| 41 | —OCH₃ | —C(=O)NH—S(=O)₂—CH₃ | 3-Trifluoromethyl-phenyl | (R)-CH₃ | 658 |

*mass spectrometric data

Synthesis of Compounds

Compounds of Formula (I) described herein are synthesized using standard synthetic techniques or using methods known in the art in combination with methods described herein. In additions, solvents, temperatures and other reaction conditions presented herein may vary.

The starting material used for the synthesis of the compounds of Formula (I) are either synthesized or obtained from commercial sources, such as, but not limited to, Sigma-Aldrich, Fluka, Acros Organics, Alfa Aesar, and the like. General methods for the preparation of compounds can be modified by the use of appropriate reagents and conditions for the introduction of the various moieties found in the formulae as provided herein.

In some embodiments, the compounds of Formula (I) are prepared as described below.

Scheme 1.

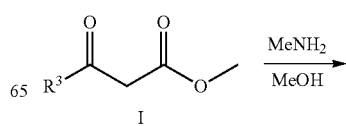

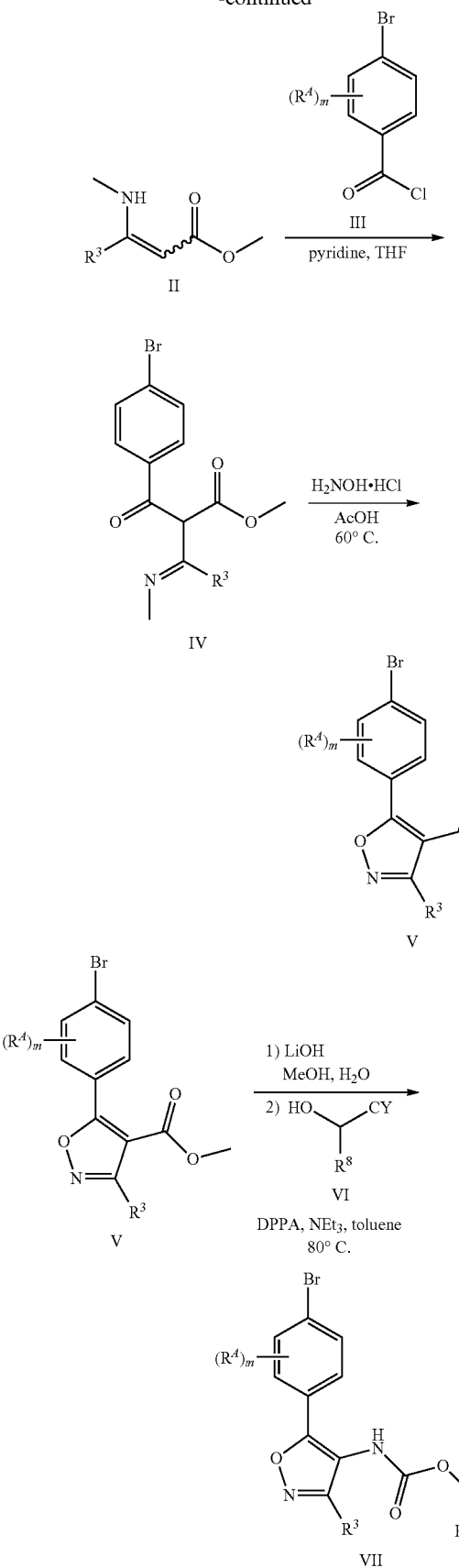

In one aspect, the synthesis of compounds of Formula (I) begins with the reaction of an alkyl acetoacetate with methylamine to provide a compound of structure II. Compounds of structure II are reacted with a substituted or unsubstituted 4-halo-benzoyl chloride (structure III) to provide compounds of structure IV. Treatment of compounds of structure IV with hydroxylamine and acetic acid provides isoxazoles of structure V. Hydrolysis of the ester group of isoxazoles of structure V provides carboxylic acids of structure VI. A Curtius rearrangement of carboxylic acids of structure VI in the presence of hydroxy compounds of structure VI provides carbamate compounds of structure VII.

Scheme 2.

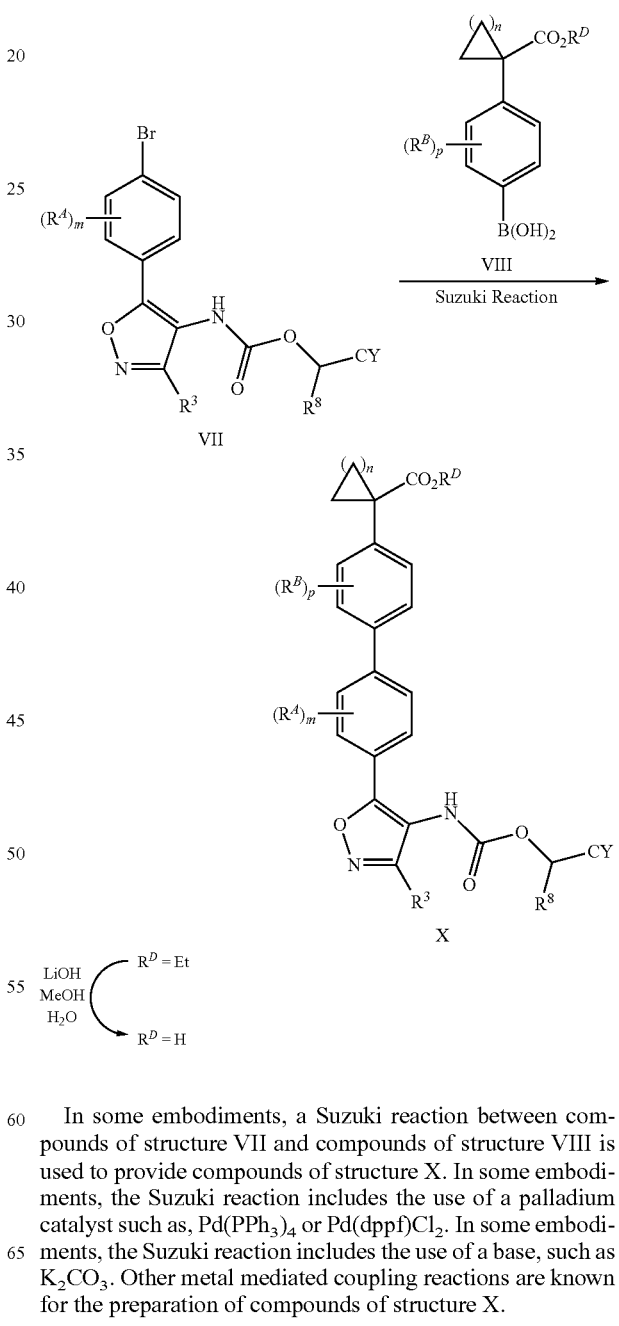

In some embodiments, a Suzuki reaction between compounds of structure VII and compounds of structure VIII is used to provide compounds of structure X. In some embodiments, the Suzuki reaction includes the use of a palladium catalyst such as, $Pd(PPh_3)_4$ or $Pd(dppf)Cl_2$. In some embodiments, the Suzuki reaction includes the use of a base, such as $K_2CO_3$. Other metal mediated coupling reactions are known for the preparation of compounds of structure X.

Scheme 3.

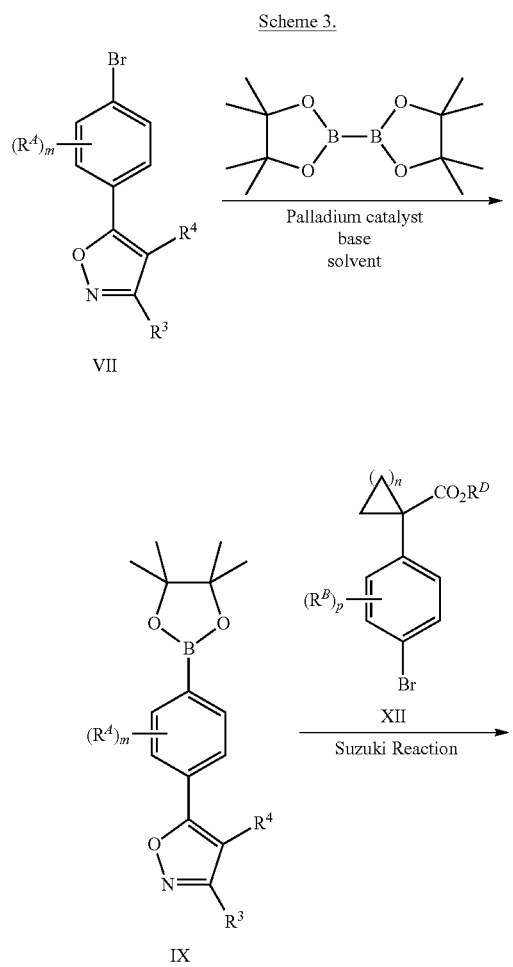

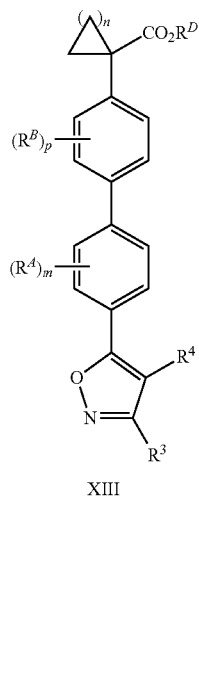

In some embodiments, compounds of structure VII are reacted with a borylating agent using transition metal mediated reaction conditions to form boronate compounds of structure IX. In some embodiments, the borylating reaction to form IX includes the use of a palladium catalyst, such as Pd(PPh$_3$)$_4$ or Pd(dppf)Cl$_2$, in the presence of a suitable base, such as potassium acetate. Boronate compounds of structure IX are reacted with compounds of structure XII under palladium mediated coupling conditions (Suzuki reaction conditions) to form compounds of structure XIII.

In some embodiments, the compounds of Formula (I) are prepared as described in Scheme 4.

Scheme 4.

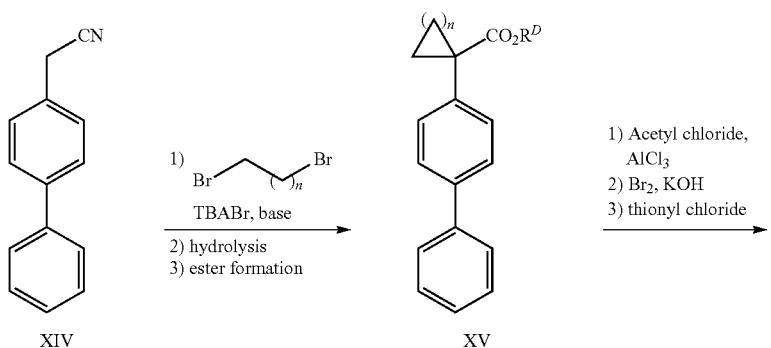

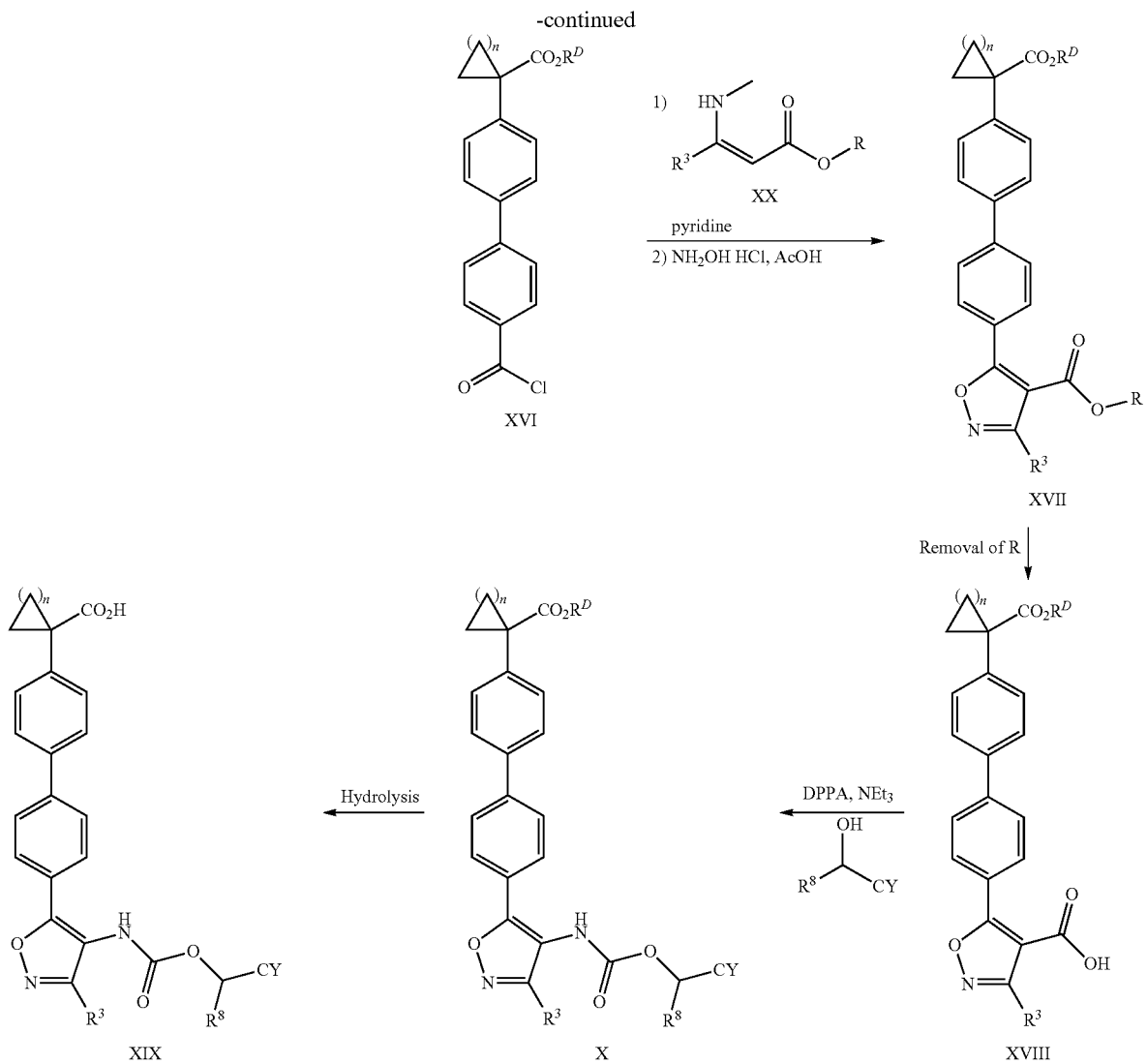

In some embodiments, biphenyl compounds of structure XIV are elaborated into the polycyclic compounds as shown in scheme 4. Biphenyl compounds of structure XIV are treated with a dihaloalkyl compound, such as 1,2-dibromoethane, to form a cycloalkyl group. The cyano group is hydrolysed to the acid and an ester is formed from the acid to provide tricyclic compounds of structure XV. In some embodiments, $R^D$ is ethyl. In some embodiments, $R^D$ is isopropyl. Tricyclic compounds of structure XV are then treated with acetyl chloride in the presence of a suitable Lewis acid, follow by conversion of the acetyl group to the carboxylic acid and treatment of the carboxylic acid with thionyl chloride to provide acid chlorides of structure XVI. Acid chlorides of structure XVI are then used to prepare isoxazoles of structure XVII as described in Scheme 1. In some embodiments, R is an alkyl group. In some embodiments, R is methyl and R is removed from isoxazoles of structure XVII under hydrolysis conditions. In some embodiments, R is benzyl and R is removed from isoxazoles of structure XVII under hydrogenation conditions (e.g. $H_2$, Pd/C). A Curtius rearrangement of carboxylic acids of structure XVIII in the presence of hydroxy compounds CY—CH($R^8$)—OH provides carbamate compounds of structure X.

In one aspect, the compounds of Formula (I) are prepared as outlined in the Examples.

Further Forms of Compounds

In one aspect, compounds of Formula (I) possess one or more stereocenters and each stereocenter exists independently in either the R or S configuration. The compounds presented herein include all diastereomeric, and enantiomeric forms. Stereoisomers are obtained, if desired, by methods such as, stereoselective synthesis and/or the separation of stereoisomers by chiral chromatographic columns.

The methods and formulations described herein include the use of N-oxides (if appropriate), crystalline forms (also known as polymorphs), amorphous phases, and/or pharmaceutically acceptable salts of compounds having the structure of Formula (I), as well as metabolites and active metabolites of these compounds having the same type of activity. In some situations, compounds may exist as tautomers. All tautomers are included within the scope of the compounds presented herein. In specific embodiments, the compounds described herein exist in solvated forms with pharmaceutically acceptable solvents such as water, ethanol, and the like. In other embodiments, the compounds described herein exist in unsolvated form.

In some embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

In some embodiments, sites on the aromatic ring portion of compounds of Formula (I) are susceptible to various metabolic reactions. Incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a deuterium, a halogen, or an alkyl group.

In another embodiment, the compounds described herein are labeled isotopically or by another other means, including, but not limited to, the use of chromophores or fluorescent moieties, bioluminescent labels, or chemiluminescent labels.

In one aspect, substitution with isotopes such as deuterium affords certain therapeutic advantages resulting from greater metabolic stability, such as, for example, increased in vivo half-life or reduced dosage requirements.

"Pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

In some embodiments, pharmaceutically acceptable salts are obtained by reacting a compound of Formula (I) with acids. Pharmaceutically acceptable salts are also obtained by reacting a compound of Formula (I) with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable inorganic acid (e.g. hydrochloric acid, hydrobromic acid, sulfuric acid, phosphoric acid, and the like); or with an organic acid (e.g. acetic acid, propionic acid, glycolic acid, pyruvic acid, lactic acid, malonic acid, succinic acid, malic acid, maleic acid, fumaric acid, trifluoroacetic acid, tartaric acid, citric acid, benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, salicylic acid, stearic acid, muconic acid, butyric acid, phenylacetic acid, phenylbutyric acid, valproic acid, and the like); (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like. In some embodiments, a sodium salt of the compound of Formula (I) is prepared.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Compounds described herein, such as compounds of Formula (I), may be in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound.

Certain Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" refers to an aliphatic hydrocarbon. The alkyl may be saturated or unsaturated. The alkyl, whether saturated or unsaturated, is a branched alkyl or straight chain alkyl. Typical alkyl groups include, but are in no way limited to, methyl, ethyl, propyl, isopropyl, butyl, isobutyl, sec-butyl, tertiary butyl, pentyl, neopentyl, hexyl, allyl, but-2-enyl, but-3-enyl, and the like.

An "alkoxy" group refers to a (alkyl)O-group, where alkyl is as defined herein.

"Cycloalkyl" refers to cyclopropyl, cyclopropenyl, cyclobutyl, cyclobutenyl, cyclopentyl, cyclopentenyl, cyclohexyl, or cyclohexenyl.

The term "halo" or, alternatively; "halogen" or "halide" means fluoro, chloro, bromo or iodo.

The term "fluoroalkyl" refers to an alkyl in which one or more hydrogen atoms are replaced by a fluorine atom.

The term "heteroalkyl" refers to an alkyl group in which one or more skeletal atoms of the alkyl are selected from an atom other than carbon, e.g., oxygen, nitrogen (e.g. NH or Nalkyl), sulfur, or combinations thereof. In some embodiments, one aspect, heteroalkyl refers to an alkyl group in which one of the skeletal atoms of the alkyl is oxygen.

The term "optionally substituted" or "substituted" means that the referenced group may be substituted with one or more additional group(s) individually and independently selected from halogen, —CN, —NH$_2$, —OH, —NH(CH$_3$), —N(CH$_3$)$_2$, alkyl, cycloalkyl, fluoroalkyl, heteroalkyl, alkoxy, fluoroalkoxy, —S-alkyl, or —S(=O)$_2$alkyl. In some embodiments, an optional substituent is selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, substituted groups are substituted with one of the preceding groups.

The term "acceptable" with respect to a formulation, composition or ingredient, as used herein, means having no persistent detrimental effect on the general health of the subject being treated.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist, partial agonist, an inverse agonist and antagonist. In one embodiment, a modulator is an antagonist.

The term "agonist," as used herein, refers to a molecule such as a compound, a drug, an enzyme activator or a hormone modulator that binds to a specific receptor and triggers a response in the cell. An agonist mimics the action of an endogenous ligand (such as LPA, prostaglandin, hormone or neurotransmitter) that binds to the same receptor.

The term "antagonist," as used herein, refers to a molecule such as a compound, which diminishes, inhibits, or prevents the action of another molecule or the activity of a receptor site. Antagonists include, but are not limited to, competitive antagonists, non-competitive antagonists, uncompetitive antagonists, partial agonists and inverse agonists.

The term "LPA-dependent", as used herein, refers to conditions or disorders that would not occur, or would not occur to the same extent, in the absence of LPA.

The term "LPA-mediated", as used herein, refers to refers to conditions or disorders that might occur in the absence of LPA but can occur in the presence of LPA.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I) and a co-agent, are both administered to a patient simultaneously in the form of a single entity or dosage. The term "non-fixed combination" means that the active ingredients, e.g. a compound of Formula (I) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "subject" or "patient" encompasses mammals. Examples of mammals include, but are not limited to, humans, chimpanzees, apes, monkey, cattle, horses, sheep, goats, swine, rabbits, dogs, cats, rodents, rats, mice guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions/Formulations and Routes of Administration

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound of Formula (I) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, antifoaming agents, antioxidants, preservatives, or one or more combination thereof. The pharmaceutical composition facilitates administration of the compound to an organism.

Pharmaceutical formulations described herein are administrable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compounds of Formula (I) are administered orally.

In some embodiments, the compounds of Formula (I) are administered topically. In such embodiments, the compound of Formula (I) is formulated into a variety of topically administrable compositions, such as solutions, suspensions, lotions, gels, pastes, shampoos, scrubs, rubs, smears, medicated sticks, medicated bandages, balms, creams or ointments. In one aspect, the compounds of Formula (I) are administered topically to the skin.

In another aspect, the compounds of Formula (I) are administered by inhalation.

In another aspect, the compounds of Formula (I) are formulated for intranasal administration. Such formulations include nasal sprays, nasal mists, and the like.

In another aspect, the compounds of Formula (I) are formulated as eye drops.

In any of the aforementioned aspects are further embodiments in which the effective amount of the compound of Formula (I) is: (a) systemically administered to the mammal; and/or (b) administered orally to the mammal; and/or (c) intravenously administered to the mammal; and/or (d) administered by inhalation to the mammal; and/or (e) administered by nasal administration to the mammal; or and/or (f) administered by injection to the mammal; and/or (g) administered topically to the mammal; and/or (h) administered by ophthalmic administration; and/or (i) administered rectally to the mammal; and/or (j) adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain embodiments, a compound as described herein is administered in a local rather than systemic manner.

In some embodiments, the compound described herein is administered topically. In some embodiments, the compound described herein is administered systemically.

In some embodiments, the pharmaceutical formulation is in the form of a tablet. In other embodiments, pharmaceutical formulations of the compounds of Formula (I) are in the form of a capsule.

In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, a compound of Formula (I) is formulated for use as an aerosol, a mist or a powder.

For buccal or sublingual administration, the compositions may take the form of tablets, lozenges, or gels formulated in a conventional manner.

In some embodiments, compounds of Formula (I) are prepared as transdermal dosage forms.

In one aspect, a compound of Formula (I) is formulated into a pharmaceutical composition suitable for intramuscular, subcutaneous, or intravenous injection.

In some embodiments, the compounds described herein may be administered topically and can be formulated into a variety of topically administrable compositions, such as solutions, suspensions, lotions, gels, pastes, medicated sticks, balms, creams or ointments.

In some embodiments, the compounds of Formula (I) are formulated in rectal compositions such as enemas, rectal gels, rectal foams, rectal aerosols, suppositories, jelly suppositories, or retention enemas.

Methods of Dosing and Treatment Regimens

In one embodiment, the compounds of Formula (I) are used in the preparation of medicaments for the treatment of LPA-dependent or LPA-mediated diseases or conditions. In addition, a method for treating any of the diseases or conditions described herein in a subject in need of such treatment, involves administration of pharmaceutical compositions that include at least one compound of Formula (I) or a pharmaceutically acceptable salt, active metabolite, prodrug, or solvate thereof, in therapeutically effective amounts to said subject.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition.

In certain embodiments, the dose of drug being administered may be temporarily reduced or temporarily suspended for a certain length of time (i.e., a "drug holiday").

Doses employed for adult human treatment are typically in the range of 0.01 mg-5000 mg per day or from about 1 mg to about 1000 mg per day. In one embodiment, the desired dose is conveniently presented in a single dose or in divided doses.

Patient Selection

In any of the aforementioned aspects involving the prevention or treatment of LPA-mediated diseases or conditions are further embodiments comprising identifying patients by screening for LPA receptor gene SNPs. Patients can be further selected based on increased LPA receptor expression in the tissue of interest. LPA receptor expression are determined by methods including, but not limited to, northern blotting, western blotting, quantitative PCR (qPCR), flow cytometry, autoradiography (using a small molecule radioligand or PET ligand). In some embodiments, patients are selected based on the concentration of serum or tissue LPA measured by mass spectrometry. In some embodiments, patients are selected based on a combination of the above markers (increased LPA concentrations and increased LPA receptor expression).

Combination Treatments

In certain instances, it is appropriate to administer at least one compound of Formula (I) in combination with another therapeutic agent.

In one specific embodiment, a compound of Formula (I) is co-administered with a second therapeutic agent, wherein the compound of Formula (I) and the second therapeutic agent modulate different aspects of the disease, disorder or condition being treated, thereby providing a greater overall benefit than administration of either therapeutic agent alone.

For combination therapies described herein, dosages of the co-administered compounds vary depending on the type of co-drug(s) employed, on the specific drug(s) employed, on the disease or condition being treated and so forth. In additional embodiments, when co-administered with one or more other therapeutic agents, the compound provided herein is administered either simultaneously with the one or more other therapeutic agents, or sequentially.

If administration is simultaneous, the multiple therapeutic agents are, by way of example only, provided in a single, unified form, or in multiple forms.

In another embodiment described herein, methods for treatment of proliferative disorders, including cancer, comprises administration to a mammal a compound of Formula (I) in combination with one or more anti-cancer agents and/or radiation therapy.

In one aspect, compounds of Formula (I) are to treat or reduce fibrosis in a mammal. In one aspect, compounds of Formula (I) are administered in combination with one or more immunosuppresants. In some embodiments, a compound of Formula (I) is administered with corticosteroids.

In yet another embodiment described herein, methods for treating LPA-dependent or LPA-mediated conditions or diseases, such as the therapy of respiratory disorders (e.g., pulmonary fibrosis, asthma, COPD, rhinitis), comprises administration to a patient compounds, pharmaceutical compositions, or medicaments described herein in combination with at least one agent used in the treatment of respiratory conditions.

In some embodiments, compounds of Formula (I) are administered to a patient in combination with anti-inflammatory agents.

In one embodiment, compounds of Formula (I) are administered to a patient in combination with inhaled corticosteroids.

EXAMPLES

These examples are provided for illustrative purposes only and not to limit the scope of the claims provided herein.

Synthesis of Compounds (R)-2'-chloro-alpha-methylbenzyl alcohol

Using the procedure of Meier et al (Tetrahedron, 1996, 52, 589; Method 3), 2'-chloroacetophenone (Aldrich) was reduced to give (R)-2'-chloro-alpha-methylbenzylalcohol. (% e.e. determined by HPLC analysis of the acetate derivative (made by reacting the benzyl alcohol with acetyl chloride and triethylamine in methylene chloride) using Chiralcel OD eluted with 99:1 Hexane:Ethanol. R isomer retention time 4.3 minutes)

(S)-2'-chloro-alpha-methylbenzyl alcohol

Using the procedure of Meier et al (Tetrahedron, 1996, 52, 589; Method 3), 2'-chloroacetophenone (Aldrich) was reduced to give (S)-2'-chloro-alpha-methylbenzylalcohol. (% e.e. determined by HPLC analysis of the acetate derivative (made by reacting the benzyl alcohol with acetyl chloride and triethylamine in methylene chloride) using Chiralcel OD eluted with 99:1 Hexane:Ethanol. S isomer retention time 5.3 minutes).

(R)-2'-fluoro-alpha-methylbenzyl alcohol

Using the procedure of Meier et al (Tetrahedron, 1996, 52, 589; Method 3), 2'-fluoroacetophenone (Aldrich) was reduced to give (R)-2'-fluoro-alpha-methylbenzylalcohol. (% e.e. determined by HPLC analysis of the acetate derivative (made by reacting the benzyl alcohol with acetyl chloride and triethylamine in methylene chloride) using Chiralcel OD eluted with 99.8:0.2 Hexane:Ethanol. R isomer retention time 5.9 minutes).

(S)-2'-fluoro-alpha-methylbenzyl alcohol

Using the procedure of Meier et al (Tetrahedron, 1996, 52, 589; Method 3), 2'-fluoroacetophenone (Aldrich) was reduced to give (S)-2'-fluoro-alpha-methylbenzylalcohol. (% e.e. determined by HPLC analysis of the acetate derivative (made by reacting the benzyl alcohol with acetyl chloride and triethylamine in methylene chloride) using Chiralcel OD eluted with 99.8:0.2 Hexane:Ethanol. S isomer retention time 6.7 minutes).

Example 1

Synthesis of 1-{4'-[3-Methyl-4-((R)-1-phenyl-ethoxycarbonylamino)-isoxazol-5-yl]-biphenyl-4-yl}-cyclopropanecarboxylic acid (Compound 1)

Step 1: 3-Methylamino-but-2-enoic acid methyl ester: To a solution of methyl acetoacetate (29.4 g, 253 mmol) in MeOH (30 mL) was added methylamine (33 wt % in EtOH; 48 mL, 385 mmol) dropwise at room temperature. The reaction was stirred for 1 hour, and then concentrated and dried to give the title compound as a white crystalline solid.

Step 2: 2-(4-Bromo-benzoyl)-3-oxo-butyric acid methyl ester: To 3-methylamino-but-2-enoic acid methyl ester (5.0 g, 39.1 mmol) in THF (70 mL) was added pyridine (3.7 mL). The mixture was cooled to 0° C., and 4-bromobenzoyl chloride (8.55 g, 39.1 mmol) in THF (30 mL) was added dropwise over 2 minutes. The reaction was warmed to room temperature over 1 hour and then stirred at room temperature overnight. Aqueous work-up gave the title compound.

Step 3: 5-(4-Bromo-phenyl)-3-methyl-isoxazole-4-carboxylic acid methyl ester: 2-(4-Bromo-benzoyl)-3-oxo-butyric acid methyl ester (11 g, 39 mmol) and hydroxylamine hydrochloride (2.66 g, 39 mmol) were combined in acetic acid (50 mL), and the reaction was stirred at 115° C. for 1 hour. After cooling, aqueous work-up gave the title compound.

Step 4: 5-(4-Bromo-phenyl)-3-methyl-isoxazole-4-carboxylic acid: Lithium hydroxide (2 g, 47.7 mmol) was added to a solution of 5-(4-bromo-phenyl)-3-methyl-isoxazole-4-carboxylic acid methyl ester (7 g, 23.6 mmol) in MeOH (50 mL) and H$_2$O (10 mL), and the reaction was stirred at 60° C. for 1 hour. Acidic work-up the title compound.

Step 5: [5-(4-Bromo-phenyl)-3-methyl-isoxazol-4-yl]-carbamic acid (R)-1-phenyl-ethyl ester: 5-(4-Bromo-phenyl)-3-methyl-isoxazole-4-carboxylic acid (2.0 g, 7.09 mmol) and triethylamine (0.99 mL, 7.09 mmol) were dissolved in toluene (50 mL). Diphenylphosphoryl azide (1.5 mL, 7.09 mmol) was added, followed by (R)-(+)-1-phenylethyl alcohol (0.865 g, 7.09 mmol; commercially available or prepared using procedures described herein or in the literature: e.g. E. J. Corey et al. *J. Am. Chem.* 1987, 109, 5551-5553), and the reaction was stirred at 80° C. for 4 hours. The mixture was concentrated, and the residue was purified by silica gel chromatography to give the title compound.

Step 6: 1-{4'-[3-Methyl-4-((R)-1-phenyl-ethoxycarbonylamino)-isoxazol-5-yl]-biphenyl-4-yl}-cyclopropanecarboxylic acid: [5-(4-Bromo-phenyl)-3-methyl-isoxazol-4-yl]-carbamic acid (R)-1-phenyl-ethyl ester (0.248 g, 0.62 mmol), 4-(1'-carboxyl-cyclopropyl)phenylboronic acid (0.160 g, 0.62 mmol), and sodium carbonate (0.155 g, 1.85 mmol) were combined in 2:1 DME:H$_2$O. The solution was purged with N$_2$ for 10 minutes, and then bis(triphenylphosphine)palladium (II) dichloride (0.047 g, 0.06 mmol) was added. The reaction was purged with N$_2$ for an additional 10 minutes, and then stirred in a sealed tube at 80° C. for 2 hours. The mixture was partitioned between EtOAc and H$_2$O, and the aqueous layer was extracted with EtOAc. The combined organic layers were dried over MgSO$_4$, filtered, and concentrated, and the residue was purified by silica gel chromatography to give the title compound.

Example 1a

Alternate synthesis of 1-{4'-[3-Methyl-4-((R)-1-phenyl-ethoxycarbonylamino)-isoxazol-5-yl]-biphenyl-4-yl}-cyclopropanecarboxylic acid (Compound 1)

Step 1: 1-(biphenyl-4-yl)cyclopropanecarbonitrile: 4-phenyl-phenylacetonitrile (VWR scientific, 55.7 g, 289 mmol) was added to a solution of KOH (161.6 g, 2890 mmol) in water (170 mL) and toluene (550 mL) at room temperature. Tetrabutyl ammonium bromide (9.2 g, 29 mmol) followed by 1,2 dibromoethane (64.9 g, 347 mmol) were added and the solution was heated to 65° C. overnight. Reaction complete by TLC (10% EtOAc/hex). The organic layer was extracted 2 times with dilute hydrochloric acid, dried and evaporated to yield 63 g of 1-(biphenyl-4-yl)cyclopropanecarbonitrile.

Step 2: 1-(Biphenyl-4-yl)cyclopropanecarboxylic acid: 1-(Biphenyl-4-yl)cyclopropanecarbonitrile (63 g, 288 mmol), KOH (1130 mmol) and ethylene glycol (350 mL) were heated to 160° C. for 6 hours (reaction complete by LCMS). The solution was cooled to room temperature, water (1.5 L) was added and the solution acidified to precipitate the product. The product was filtered overnight on a large Buchner (product formed a gel like suspension). The resulting wet solid was extracted with CH$_2$Cl$_2$ (~2 L) and water, dried and evaporated to yield ~60 g of 1-(biphenyl-4-yl)cyclopropanecarboxylic acid that was used as such in the next step.

Step 3: 1-(Biphenyl-4-yl)cyclopropanecarboxylic acid ethyl ester: 1-(Biphenyl-4-yl)cyclopropanecarboxylic acid (10 g, 42 mmol), ethanol (100 mL) and sulfuric acid (40 mL) were heated to 65° C. for 4 hours. The product was extracted with CH$_2$Cl$_2$ and water (2×), dried and evaporated to yield 9.5 g of 1-(biphenyl-4-yl)cyclopropanecarboxylic acid ethyl ester.

Step 4: 1-(4'-Acetylbiphenyl-4-yl)cyclopropanecarboxylic acid ethyl ester: To 1-(biphenyl-4-yl)cyclopropanecarboxylic acid ethyl ester (9 g, 33.8 mmol) in CH$_2$Cl$_2$ (100 mL) was added aluminum chloride (9.4 g, 71 mmol) followed by acetyl chloride (5.5 g, 71 mmol). The solution was stirred at room temperature for 1.5 hours then slowly poured into water. The organic layer was separated and extracted 2 times with water. The organic layer was dried and evaporated to yield 11.3 g of the title compound.

Step 5: 4'-(1-(Ethoxycarbonyl)cyclopropyl)biphenyl-4-carboxylic acid: To 1-(4'-acetylbiphenyl-4-yl)cyclopropanecarboxylic acid ethyl ester (10.1 g, 33 mmol) in dioxane (200 mL) at ~10° C. was added a solution of bromine (26.4 g, 165 mmol), sodium hydroxide (22.4 g, 561 mmol) in water (150 mL). The solution was stirred at room temperature for 30 minutes, poured into water (500 mL) and acidified with dilute hydrochloric acid. Sodium metabisulfite was added until the brown bromine color dissipated. The product was filtered and dried in a vacuum over overnight at 40° C. to yield 10 g of 4'-(1-(ethoxycarbonyl)cyclopropyl)biphenyl-4-carboxylic acid.

Step 6: 3-Methylamino-but-2-enoic acid benzyl ester: To benzyl acetoacetate (29 g, 151 mmol) in ethanol (30 mL) was added methyl amine (33% in ethanol, 7.02 g, 226 mmol). The solution was stirred for 2 hours at room temperature followed by evaporation to yield a yellow oil (~30 g).

Step 7: Ethyl 1-(4'-(2-(benzyloxycarbonyl)-3-(methylamino)but-2-enoyl)biphenyl-4-yl)cyclopropanecarboxylate: 4'-(1-(Ethoxycarbonyl)cyclopropyl)biphenyl-4-carboxylic acid (4.47 g, 14.4 mmol), dichloroethane (50 mL), DMF (0.1 mL), thionyl chloride (2.3 mL, 32 mmol) were heated to 80° C. for 1 hours. (acid chloride formation was monitored by adding small aliquot (100 µL) to a solution of benzyl amine in acetonitrile and analyzing for the benzyl amide by LCMS; no starting material was observed by LCMS). The solution was evaporated on a rotavap and THF (10 mL) was added. The solution of the acid chloride in THF was added via syringe to a solution of 3-methylamino-but-2-enoic acid benzyl ester (3.23 g, 15.8 mmol) and pyridine (2.4 mL, 30.2 mmol) in THF (50 mL). The solution was stirred at 50° C. for 2 hours then the volatiles were evaporated using a rotavap to yield the crude product.

Step 8: Benzyl 5-(4'-(1-(ethoxycarbonyl)cyclopropyl)biphenyl-4-yl)-3-methylisoxazole-4-carboxylate: To the crude material from the previous reaction was added hydroxylamine hydrochloride (1.5 g, 21.6 mmol) and acetic acid (50 mL). The solution was heated to 95° C. for 30 minutes cooled to room temperature, extracted with CH$_2$Cl$_2$ and water (4 times, second and third time made basic with sodium bicarbonate). Dried, evaporated and purified on column 0 to 20% EtOAc/hexanes to yield 3.3 g of product.

Step 9: 5-(4'-(1-(ethoxycarbonyl)cyclopropyl)biphenyl-4-yl)-3-methylisoxazole-4-carboxylic acid: The benzyl ester from Step 8 (1 g, 2.1 mmol) in ethyl acetate (10 mL) was degassed with nitrogen for 10 minutes. 10% Palladium on activated carbon (0.2 g, 0.2 mmol) was added and the solution was sparged with hydrogen via balloon. The balloon of hydrogen was maintained on the head space and the solution stirred for 1.5 hours. The reaction was diluted with ethanol and actone (to solubilize the product), filtered through celite and evaporated to yield 700 mg product.

Step 10: 1-{4'-[3-Methyl-4-((R)-1-phenyl-ethoxycarbonylamino)-isoxazol-5-yl]-biphenyl-4-yl}-cyclopropanecarboxylic acid ethyl ester: To the acid from Step 9 (0.5 g, 1.28 mmol) in toluene (5 mL) was added (R)-1-phenyl ethanol (0.16 g, 1.34 mmol), triethyl amine (0.26 g, 2.56 mmol) and diphenyl phosphoryl azide (0.39 g, 1.4 mmol). The solution was heated to 80° C. for 1 hour, cooled to room temperature and extracted with water 3 times. The organic layer wad dried and evaporated to yield 0.61 g. The product was further purified by column 0 to 40% EtOAc/hex to yield 0.42 g of pure product (65%) as an oil that foams on drying under vacuum.

Step 11: 1-{4'-[3-Methyl-4-((R)-1-phenyl-ethoxycarbonylamino)-isoxazol-5-yl]-biphenyl-4-yl}-cyclopropanecarboxylic acid: To ethyl ester (22.7 g, 44 mmol) in methanol (300 mL) was added lithium hydroxide (9.1 g, 222 mmol). The solution was heated to 65° C. for 2 hours, extracted into methylene choride and washed with diluted hydrochloric acid. The organic layer was dried and evaporated to yield 20.8 grams product.

Example 1b

Alternate synthesis of 1-{4'-[3-Methyl-4-((R)-1-phenyl-ethoxycarbonylamino)-isoxazol-5-yl]-biphenyl-4-yl}-cyclopropanecarboxylic acid (Compound 1)

Step 1: 1-(Biphenyl-4-yl)cyclopropanecarboxylic acid isopropyl ester: 1-(Biphenyl-4-yl)cyclopropanecarboxylic acid (10 g, 42 mmol), isopropanol (100 mL), thionyl chloride (6.8 mL, 92 mmol) were heated to 65° C. for 4 hours. Sulfuric acid (20 mL) was added and heated at 65° C. overnight. The product is extracted with $CH_2Cl_2$ and water (2×) dried and evaporated to yield 10.8 g of the title compound.

Step 2: 1-(4'-Acetylbiphenyl-4-yl)cyclopropanecarboxylic acid isopropyl ester: To 1-(biphenyl-4-yl)cyclopropanecarboxylic acid isopropyl ester (10.2 g, 36 mmol) in $CH_2Cl_2$ (100 mL) was added aluminum chloride (10.2 g, 76.5 mmol) followed by acetyl chloride (5.97 g, 76.5 mmol). The solution was stirred at room temperature for 1.5 hours then slowly poured into water. The organic layer was separated and extracted 1 time with sodium potassium tartrate solution (20 g in 250 mL water). The organic layer was dried and evaporated to yield 12.6 g of the title compound.

Step 3: 4'-(1-(isopropoxycarbonyl)cyclopropyl)biphenyl-4-carboxylic acid: To 1-(4'-acetylbiphenyl-4-yl)cyclopropanecarboxylic acid isopropyl ester (11.6 g, 36 mmol) in dioxane (200 mL) at ~10° C. was added a solution of bromine (28.8 g, 180 mmol), sodium hydroxide (24.5 g, 612 mmol) in water (150 mL). The solution was stirred at room temperature for 30 minutes poured into water (500 mL) and acidified with dilute hydrochloric acid. Sodium metabisulfite was added until the brown bromine color dissipated. The product was filtered and dried in a vacuum over overnight at 40° C. to yield 10 g of the title compound.

Step 4: Isopropyl 1-(4'-(2-(benzyloxycarbonyl)-3-(methylamino)but-2-enoyl)biphenyl-4-yl)cyclopropanecarboxylate: 4'-(1-(Isopropoxycarbonyl)cyclopropyl)biphenyl-4-carboxylic acid (9.2 g, 28 mmol), dichloroethane (50 mL), DMF (0.1 mL), thionyl chloride (5.5 mL, 62 mmol) were heated to 75° C. for 1.5 hours. (acid chloride formation was monitored by adding small aliquot (100 μL) to a solution of benzyl amine in acetonitrile and analyzing for the benzyl amide by LCMS; no starting material was observed by LCMS). The solution was evaporated on a rotavap and THF (10 mL) was added. The solution of the acid chloride in THF was added via syringe to a solution of 3-methylamino-but-2-enoic acid methyl ester (4.0 g, 31.2 mmol) and pyridine (5.5 mL, 70 mmol) in THF (50 mL). The solution was stirred at room temperature overnight. The volatiles were evaporated on a rotavap to yield the crude product.

Step 5: Methyl 5-(4'-(1-(isopropoxycarbonyl)cyclopropyl)biphenyl-4-yl)-3-methylisoxazole-4-carboxylate: To the crude material from the previous reaction was added hydroxyl amine hydrochloride (2.9 g, 42 mmol) and acetic acid (50 mL). The solution was heated to 100° C. for 30 minutes cooled to room temperature, extracted with $CH_2Cl_2$ and water (4 times, second and third time made basic with sodium bicarbonate). The organic phase was dried, evaporated and purified on column (220 g silica; 0 to 20% EtOAc/hexanes) to yield 6 g of product.

Step 6: 5-(4'-(1-(propoxycarbonyl)cyclopropyl)biphenyl-4-yl)-3-methylisoxazole-4-carboxylic acid: To the methyl ester from Step 5 (5.2 g, 12.4 mmol) in THF (100 mL) and ethanol (20 mL) was added a solution of sodium hydroxide (1.5 g, 37.2 mmol) in water (40 mL). The solution was stirred at room temperature 3 hours. ~50 mL solvent evaporated and 200 mL water added. The product was precipitated out of solution with dilute hydrochloric acid to pH 2. The product was isolated by filtration to yield 4.6 grams of the title compound.

Step 7: 1-{4'-[3-Methyl-4-((R)-1-phenyl-ethoxycarbonylamino)-isoxazol-5-yl]-biphenyl-4-yl}-cyclopropanecarboxylic acid isopropyl ester: To the acid from Step 6 (4.0 g, 10 mmol) in toluene (50 mL) was added R-1-phenyl ethanol (1.33 g, 11 mmol), triethyl amine (2.02 g, 20 mmol) and diphenyl phosphoryl azide (3.16 g, 11.5 mmol). The solution was heated to 80° C. for 1 hour cooled to room temperature and extracted with water 3 times. The organic layer wad dried and evaporated to yield 5.7 g of the title compound.

Step 8: 1-{4'-[3-Methyl-4-((R)-1-phenyl-ethoxycarbonylamino)-isoxazol-5-yl]-biphenyl-4-yl}-cyclopropanecarboxylic acid: To the isopropyl ester from Step 7 (5.2 g, 10 mmol) in THF (30 mL), MeOH (10 mL) was added NaOH (2 g, 50 mmol) in water (10 mL). The solution is heated to 65° C. for 5 hours. The solution was cooled to room temperature, extracted with methylene chloride and dilute hydrochloric acid. The organic was dried and evaporated and the product was purified by column chromatography (0 to 60% EtOAc/hexanes) to yield ~3.5 grams of product.

Example 2

Synthesis of 1-{4'-[3-Methyl-4-((R)-1-o-tolyl-ethoxycarbonylamino)-isoxazol-5-yl]-biphenyl-4-yl}-cyclopropanecarboxylic acid (Compound 3)

Step 1: 1-(4-Bromo-phenyl)-cyclopropanecarbonitrile: Potassium hydroxide (14.3 g, 255 mmol) was dissolved in $H_2O$ (5 mL) and toluene (40 mL). 4-Bromophenylacetonitrile (5.0 g, 25.5 mmol) and tetrabutylammonium bromide (0.41 g, 1.3 mmol) was added, followed by 1,2-dibromoethane (3.25 mL, 38 mmol) dropwise over 10 minutes. The reaction was stirred at room temperature for 2 hours and then worked-up to give the title compound.

Step 2: 1-(4-Bromo-phenyl)-cyclopropanecarboxylic acid: 1-(4-Bromo-phenyl)-cyclopropanecarbonitrile (5 g, 22.5 mmol) and potassium hydroxide (5 g, 89.3 mmol) were combined in ethylene glycol (70 mL), and the reaction was stirred at 180° C. for 4 hours. The mixture was poured into $H_2O$, acidified, and filtered to give the title compound.

Step 3: 1-(4-Bromo-phenyl)-cyclopropanecarboxylic acid ethyl ester: 1-(4-Bromo-phenyl)-cyclopropanecarboxylic acid (5 g, 20.7 mmol) in EtOH (50 mL) was treated with sulfuric acid (2 mL), and the reaction was stirred at 75° C. for 1 hour. The mixture was worked up to give the title compound.

Step 4: 1-[4-(4,4,5,5-Tetramethyl-[1,3,2]dioxaborolan-2-yl)-phenyl]-cyclopropanecarboxylic acid ethyl ester: 1-(4-Bromo-phenyl)-cyclopropanecarboxylic acid ethyl ester (3.6 g, 13.4 mmol), bis(pinacolato)diboron (3.37 g, 16.1 mmol), and potassium acetate (2.8 g, 29 mmol) were combined in 1,4-dioxane (30 mL). The solution was purged with $N_2$ for 10 minutes, and then (1,1'-bis(diphenylphosphino)ferrocene)-dichloropalladium(II) (0.50 g, 0.65 mmol) was added and the reaction was heated to 80° C. for 2 hours. Aqueous work-up, followed by silica gel chromatography (0-30% EtOAc in hexanes), gave the title compound.

Step 5: (R)-1-o-Tolyl-ethanol: (S)-(−)-2-Methyl-CBS-oxazaborolidine (3.72 g, 13.4 mmol) was dissolved in THF (60 mL). Borane methyl sulfide complex (2M in THF; 36.6 mL, 73.3 mmol) was added, and the mixture was cooled to 0° C. 2'-Methylacetophenone (15 g, 111 mmol) in THF (30 mL) was added over 1 hour, and the mixture was then worked-up to yield a liquid with a white precipitate. Hexanes was added, the suspension was filtered to remove the precipitate, and the resulting filtrate was concentrated to give the title compound in 93% e.e.

Step 6: [5-(4-Bromo-phenyl)-3-methyl-isoxazol-4-yl]-carbamic acid (R)-1-o-tolyl-ethyl ester: Prepared according to the procedure described in Example 1, Step 5 using 5-(4-bromo-phenyl)-3-methyl-isoxazole-4-carboxylic acid and (R)-1-o-tolyl-ethanol.

Step 7: 1-{4'-[3-Methyl-4-((R)-1-o-tolyl-ethoxycarbonylamino)-isoxazol-5-yl]-biphenyl-4-yl}-cyclopropanecarboxylic acid ethyl ester: Prepared according to the procedure described in Example 1, Step 6 using [5-(4-bromo-phenyl)-3-methyl-isoxazol-4-yl]-carbamic acid (R)-1-o-tolyl-ethyl ester, 1-[4-(4,4,5,5-tetramethyl-[1,3,2]dioxaborolan-2-yl)-phenyl]-cyclopropanecarboxylic acid ethyl ester, and tetrakis(triphenylphosphine)palladium(0).

Step 8: 1-{4'-[3-Methyl-4-((R)-1-o-tolyl-ethoxycarbonylamino)-isoxazol-5-yl]-biphenyl-4-yl}-cyclopropanecarboxylic acid: To 1-{4'-[3-methyl-4-((R)-1-o-tolyl-ethoxycarbonylamino)-isoxazol-5-yl]-biphenyl-4-yl}-cyclopropanecarboxylic acid ethyl ester (0.36 mmol) in 2:1 MeOH:H$_2$O was added lithium hydroxide (1.1 mmol), and the reaction was stirred at room temperature until no starting material was seen by analytical LCMS. The mixture was acidified with 1N aqueous HCl and extracted with EtOAc. The combined organic layers were dried, filtered, and concentrated to give the title compound.

Example 3a

Synthesis of (R)-1-{4'-[4-(1-Cyclopropyl-ethoxycarbonylamino)-3-methyl-isoxazol-5-yl]-biphenyl-4-yl}-cyclopropanecarboxylic acid (Compound 6)

Step 1: [5-(4-Bromo-phenyl)-3-methyl-isoxazol-4-yl]-carbamic acid 1-cyclopropyl-ethyl ester: Prepared according to the procedure described in Example 1, Step 5 using 5-(4-bromo-phenyl)-3-methyl-isoxazole-4-carboxylic acid and alpha-methylcyclopropanemethanol.

Step 2: 1-{4'-[4-(1-Cyclopropyl-ethoxycarbonylamino)-3-methyl-isoxazol-5-yl]-biphenyl-4-yl}-cyclopropanecarboxylic acid ethyl ester: Prepared according to the procedure described in Example 1, Step 6 using [5-(4-bromo-phenyl)-3-methyl-isoxazol-4-yl]-carbamic acid 1-cyclopropyl-ethyl ester and 1-[4-(4,4,5,5-tetramethyl-[1,3,2]dioxaborolan-2-yl)-phenyl]-cyclopropanecarboxylic acid ethyl ester; the isolated material was then purified by preparative HPLC, using a Chiracel OD column (97:3 hexanes:EtOH) to provide enantiomer A and enantiomer B. Enantiomer A had a retention time of 27 minutes, enantiomer B had a retention time of 33 minutes.

Step 3: (R)-1-{4'-[4-(1-Cyclopropyl-ethoxycarbonylamino)-3-methyl-isoxazol-5-yl]-biphenyl-4-yl}-cyclopropanecarboxylic acid: Prepared according to the procedure described in Example 2, Step 8 using enantiomer B from Example 3a, Step 2 (1-{4'-[4-(1-cyclopropyl-ethoxycarbonylamino)-3-methyl-isoxazol-5-yl]-biphenyl-4-yl}-cyclopropanecarboxylic acid ethyl ester).

Example 3b

Alternative Synthesis of (R)-1-{4'-[4-(1-Cyclopropyl-ethoxycarbonylamino)-3-methyl-isoxazol-5-yl]-biphenyl-4-yl}-cyclopropanecarboxylic acid (Compound 6)

Step 1: (R)-alpha-methylcyclopropanemethanol: Using an analogous procedure of Meier et al (Tetrahedron, 1996, 52, 589; Method 3), cyclopropyl methyl ketone (Aldrich) was reduced to give (R)-alpha-methylcyclopropanemethanol.

Step 2: 1-(R)-[5-(4-Bromo-phenyl)-3-methyl-isoxazol-4-yl]-carbamic acid 1-cyclopropyl-ethyl ester: Prepared according to the procedure described in Example 1, Step 5 using 5-(4-bromo-phenyl)-3-methyl-isoxazole-4-carboxylic acid and (R)-alpha-methylcyclopropanemethanol.

Step 3: (R)-1-{4'-[4-(1-Cyclopropyl-ethoxycarbonylamino)-3-methyl-isoxazol-5-yl]-biphenyl-4-yl}-cyclopropanecarboxylic acid ethyl ester: Prepared according to the procedure described in Example 1, Step 6 using 1-(R)-[5-(4-bromo-phenyl)-3-methyl-isoxazol-4-yl]-carbamic acid 1-cyclopropyl-ethyl ester and 1-[4-(4,4,5,5-tetramethyl-[1,3,2]dioxaborolan-2-yl)-phenyl]-cyclopropanecarboxylic acid ethyl ester; the enantiomeric excess of the isolated material was determined by chiral HPLC to be 92% (Chiracel OD column (97:3 hexanes:EtOH, 1 ml/min, minor isomer retention time 27 min, major isomer retention time 32 minutes).

Step 4: (R)-1-{4'-[4-(1-Cyclopropyl-ethoxycarbonylamino)-3-methyl-isoxazol-5-yl]-biphenyl-4-yl}-cyclopropanecarboxylic acid: Prepared according to the procedure described in Example 2, Step 8 using (R)-(1-{4'-[4-(1-cyclopropyl-ethoxycarbonylamino)-3-methyl-isoxazol-5-yl]-biphenyl-4-yl}-cyclopropanecarboxylic acid ethyl ester).

Example 4

Synthesis of 1-(4'-{4-[(R)-1-(2-Chloro-phenyl)-ethoxycarbonylamino]-3-methyl-isoxazol-5-yl}-biphenyl-4-yl)-cyclopropanecarboxylic acid (Compound 8)

Step 1: [5-(4-Bromo-phenyl)-3-methyl-isoxazol-4-yl]-carbamic acid (R)-1-(2-chloro-phenyl)-ethyl ester: Prepared according to the procedure described in Example 1, Step 5 using 5-(4-bromo-phenyl)-3-methyl-isoxazole-4-carboxylic acid and (R)-1-(2-chloro-phenyl)-ethanol.

Step 2: 1-(4'-{4-[(R)-1-(2-Chloro-phenyl)-ethoxycarbonylamino]-3-methyl-isoxazol-5-yl}-biphenyl-4-yl)-cyclopropanecarboxylic acid: Prepared according to the procedure described in Example 1, Step 6 using [5-(4-bromo-phenyl)-3-methyl-isoxazol-4-yl]-carbamic acid (R)-1-(2-chloro-phenyl)-ethyl ester and 4-(1'-carboxyl-cyclopropyl)phenylboronic acid.

Example 5

Synthesis of 1-(4'-{3-Methyl-4-[(R)-1-(2-trifluoromethyl-phenyl)-ethoxycarbonylamino]-isoxazol-5-yl}-biphenyl-4-yl)-cyclopropanecarboxylic acid (Compound 9)

Step 1: (R)-1-(2-Trifluoromethyl-phenyl)-ethanol: Prepared according to the procedure described in Example 2, Step 5 using 2'-(trifluoromethyl)acetophenone.

Step 2: [5-(4-Bromo-phenyl)-3-methyl-isoxazol-4-yl]-carbamic acid (R)-1-(2-trifluoromethyl-phenyl)-ethyl ester: Prepared according to the procedure described in Example 1, Step 5 using (R)-1-(2-trifluoromethyl-phenyl)-ethanol and 5-(4-bromo-phenyl)-3-methyl-isoxazole-4-carboxylic acid; the isolated material was purified by preparative HPLC, using a Chiracel OD column (98.6:1.4 hexanes:EtOH) to give the title compound.

Step 3: 1-(4'-{3-Methyl-4-[(R)-1-(2-trifluoromethyl-phenyl)-ethoxycarbonylamino]-isoxazol-5-yl}-biphenyl-4-yl)-cyclopropanecarboxylic acid ethyl ester: Prepared according to the procedure described in Example 1, Step 6 using [5-(4-bromo-phenyl)-3-methyl-isoxazol-4-yl]-carbamic acid (R)-1-(2-trifluoromethyl-phenyl)-ethyl ester and 1-[4-(4,4,5,5-tetramethyl-[1,3,2]dioxaborolan-2-yl)-phenyl]-cyclopropanecarboxylic acid ethyl ester.

Step 4: 1-(4'-{3-Methyl-4-[(R)-1-(2-trifluoromethyl-phenyl)-ethoxycarbonylamino]-isoxazol-5-yl}-biphenyl-4-yl)-cyclopropanecarboxylic acid: Prepared according to the procedure described in Example 2, Step 8 using 1-(4'-{3-methyl-4-[(R)-1-(2-trifluoromethyl-phenyl)-ethoxycarbonylamino]-isoxazol-5-yl}-biphenyl-4-yl)-cyclopropanecarboxylic acid ethyl ester.

Example 6

Synthesis of 1-{4'-[3-Methyl-4-((R)-1-phenyl-ethoxycarbonylamino)-isoxazol-5-yl]-biphenyl-4-yl}-cyclopentanecarboxylic acid (Compound 11)

Step 1: 1-(4-Bromo-phenyl)-cyclopentanecarboxylic acid ethyl ester: To a solution of ethyl 4-bromophenylacetate (2 g, 8.2 mmol) in DMF (20 mL) at 0° C. was added sodium hydride (60% in mineral oil; 0.72 g, 18.1 mmol), and the mixture was stirred for 10 minutes. 1,4-Dibromobutane (1.07 mL, 9.0 mmol) was added, and the reaction was stirred at room temperature for 30 minutes. Once no starting material was seen by analytical tlc, the mixture was worked up with EtOAc and aqueous 10% HCl, and the crude material was purified by silica gel chromatography to give the title compound.

Step 2: 1-[4-(4,4,5,5-Tetramethyl-[1,3,2]dioxaborolan-2-yl)-phenyl]-cyclopentanecarboxylic acid ethyl ester: Prepared according to the procedure described in Example 2, Step 4 using 1-(4-bromo-phenyl)-cyclopentanecarboxylic acid ethyl ester and bis(pinacolato)diboron.

Step 3: 1-{4'-[3-Methyl-4-((R)-1-phenyl-ethoxycarbonylamino)-isoxazol-5-yl]-biphenyl-4-yl}-cyclopentanecarboxylic acid ethyl ester: [5-(4-bromo-phenyl)-3-methyl-isoxazol-4-yl]-carbamic acid (R)-1-phenyl-ethyl ester (0.077 g, 0.19 mmol), 1-[4-(4,4,5,5-tetramethyl-[1,3,2]dioxaborolan-2-yl)-phenyl]-cyclopentanecarboxylic acid ethyl ester (0.079 g, 0.23 mmol), and potassium carbonate (0.066 g, 0.48 mmol) were combined in 2:1 DME:$H_2O$ (3 mL). The solution was purged with $N_2$ for 5 minutes, and then tetrakis(triphenylphosphine)palladium(0) (0.022 g, 0.02 mmol) was added. The mixture was purged with $N_2$ for an additional 5 minutes, and then the reaction was stirred at 90° C. in a sealed tube for 1.5 hours. Aqueous work-up, followed by silica gel chromatography, provided the title compound.

Step 4: 1-{4'-[3-Methyl-4-((R)-1-phenyl-ethoxycarbonylamino)-isoxazol-5-yl]-biphenyl-4-yl}-cyclopentanecarboxylic acid: 1-{4'-[3-methyl-4-((R)-1-phenyl-ethoxycarbonylamino)-isoxazol-5-yl]-biphenyl-4-yl}-cyclopentanecarboxylic acid ethyl ester (0.060 g, 0.11 mmol) in 1,4-dioxane (2 mL) was treated with 1N aqueous LiOH (1 mL), and the reaction was stirred at 60° C. overnight. Acidic work-up, followed by silica gel chromatography (0-50% EtOAc in hexanes) gave the title compound.

Example 7

Synthesis of 1-{4'-[3-Methyl-4-((R)-1-phenyl-ethoxycarbonylamino)-isoxazol-5-yl]-biphenyl-4-yl}-cyclobutanecarboxylic acid (Compound 10)

Step 1: 1-(4-Bromo-phenyl)-cyclobutanecarboxylic acid ethyl ester: Prepared according to the procedure described in Example 6, Step 1 using ethyl 4-bromophenylacetate and 1,3-dibromopropane.

Step 2: 1-[4-(4,4,5,5-Tetramethyl-[1,3,2]dioxaborolan-2-yl)-phenyl]-cyclobutanecarboxylic acid ethyl ester: Prepared according to the procedure described in Example 2, Step 4 using 1-(4-bromo-phenyl)-cyclobutanecarboxylic acid ethyl ester and bis(pinacolato)diboron.

Step 3: 1-{4'-[3-Methyl-4-((R)-1-phenyl-ethoxycarbonylamino)-isoxazol-5-yl]-biphenyl-4-yl}-cyclobutanecarboxylic acid ethyl ester: Prepared according to the procedure described in Example 6, Step 3 using [5-(4-bromo-phenyl)-3-methyl-isoxazol-4-yl]-carbamic acid (R)-1-phenyl-ethyl ester and 1-[4-(4,4,5,5-tetramethyl-[1,3,2]dioxaborolan-2-yl)-phenyl]-cyclobutanecarboxylic acid ethyl ester.

Step 4: 1-{4'-[3-Methyl-4-((R)-1-phenyl-ethoxycarbonylamino)-isoxazol-5-yl]-biphenyl-4-yl}-cyclobutanecarboxylic acid: Prepared according to the procedure described in Example 6, Step 4 using 1-{4'-[3-methyl-4-((R)-1-phenyl-ethoxycarbonylamino)-isoxazol-5-yl]-biphenyl-4-yl}-cyclobutanecarboxylic acid ethyl ester.

Example 8

Synthesis of 1-{4'-[4-(1-Cyclohexyl-ethoxycarbonylamino)-3-methyl-isoxazol-5-yl]-biphenyl-4-yl}-cyclopropanecarboxylic acid (Compound 2)

Step 1: [5-(4-Bromo-phenyl)-3-methyl-isoxazol-4-yl]-carbamic acid 1-cyclohexyl-ethyl ester: Prepared according to the procedure described in Example 1, Step 5 using 5-(4-bromo-phenyl)-3-methyl-isoxazole-4-carboxylic acid and 1-cyclohexylethanol.

Step 2: 1-{4'-[4-(1-Cyclohexyl-ethoxycarbonylamino)-3-methyl-isoxazol-5-yl]-biphenyl-4-yl}-cyclopropanecarboxylic acid ethyl ester: Prepared according to the procedure described in Example 1, Step 6 using [5-(4-bromo-phenyl)-3-methyl-isoxazol-4-yl]-carbamic acid 1-cyclohexyl-ethyl ester and 1-[4-(4,4,5,5-tetramethyl-[1,3,2]dioxaborolan-2-yl)-phenyl]-cyclopropanecarboxylic acid ethyl ester.

Step 3: 1-{4'-[4-(1-Cyclohexyl-ethoxycarbonylamino)-3-methyl-isoxazol-5-yl]-biphenyl-4-yl}-cyclopropanecarboxylic acid: Prepared according to the procedure described in Example 2, Step 8 using 1-{4'-[4-(1-cyclohexyl-ethoxycarbonylamino)-3-methyl-isoxazol-5-yl]-biphenyl-4-yl}-cyclopropanecarboxylic acid ethyl ester.

Example 9

Synthesis of 1-[4'-(4-Benzyloxycarbonylamino-3-methyl-isoxazol-5-yl)-biphenyl-4-yl]-cyclopropanecarboxylic acid (Compound 4)

Step 1: [5-(4-Bromo-phenyl)-3-methyl-isoxazol-4-yl]-carbamic acid benzyl ester: Prepared according to the procedure described in Example 1, Step 5 using 5-(4-bromo-phenyl)-3-methyl-isoxazole-4-carboxylic acid and benzyl alcohol.

Step 2: 1-[4'-(4-Benzyloxycarbonylamino-3-methyl-isoxazol-5-yl)-biphenyl-4-yl]-cyclopropanecarboxylic acid ethyl ester: Prepared according to the procedure described in Example 1, Step 6 using [5-(4-bromo-phenyl)-3-methyl-isoxazol-4-yl]-carbamic acid benzyl ester and 1-[4-(4,4,5,5-tetramethyl-[1,3,2]dioxaborolan-2-yl)-phenyl]-cyclopropanecarboxylic acid ethyl ester.

Step 3: 1-[4'-(4-Benzyloxycarbonylamino-3-methyl-isoxazol-5-yl)-biphenyl-4-yl]-cyclopropanecarboxylic acid: Prepared according to the procedure described in Example 2, Step 8 using 1-[4'-(4-benzyloxycarbonylamino-3-methyl-isoxazol-5-yl)-biphenyl-4-yl]-cyclopropanecarboxylic acid ethyl ester.

Example 10

Synthesis of (S)-1-{4'-[4-(1-Cyclopropyl-ethoxycarbonylamino)-3-methyl-isoxazol-5-yl]-biphenyl-4-yl}-cyclopropanecarboxylic acid (Compound 5)

Prepared according to the procedure described in Example 2, Step 8 using enantiomer A from Example 3a, Step 2 (1-{4'-[4-(1-cyclopropyl-ethoxycarbonylamino)-3-methyl-isoxazol-5-yl]-biphenyl-4-yl}-cyclopropanecarboxylic acid ethyl ester).

Example 11

Synthesis of 1-[4'-(4-Cyclopropylmethoxycarbonylamino-3-methyl-isoxazol-5-yl)-biphenyl-4-yl]-cyclopropanecarboxylic acid (Compound 7)

Step 1: [5-(4-Bromo-phenyl)-3-methyl-isoxazol-4-yl]-carbamic acid cyclopropylmethyl ester: Prepared according to the procedure described in Example 1, Step 5 using 5-(4-bromo-phenyl)-3-methyl-isoxazole-4-carboxylic acid and cyclopropyl carbinol.

Step 2: 1-[4'-(4-Cyclopropylmethoxycarbonylamino-3-methyl-isoxazol-5-yl)-biphenyl-4-yl]-cyclopropanecarboxylic acid ethyl ester: Prepared according to the procedure described in Example 1, Step 6 using [5-(4-bromo-phenyl)-3-methyl-isoxazol-4-yl]-carbamic acid cyclopropylmethyl ester and 1-[4-(4,4,5,5-tetramethyl-[1,3,2]dioxaborolan-2-yl)-phenyl]-cyclopropanecarboxylic acid ethyl ester.

Step 3: 1-[4'-(4-Cyclopropylmethoxycarbonylamino-3-methyl-isoxazol-5-yl)-biphenyl-4-yl]-cyclopropanecarboxylic acid: Prepared according to the procedure described in Example 2, Step 8 using 1-[4'-(4-cyclopropylmethoxycarbonylamino-3-methyl-isoxazol-5-yl)-biphenyl-4-yl]-cyclopropanecarboxylic acid ethyl ester.

Example 12

Synthesis of 1-(4'-{4-[1-(2-Methoxy-phenyl)-ethoxycarbonylamino]-3-methyl-isoxazol-5-yl}-biphenyl-4-yl)-cyclopropanecarboxylic acid (Compound 12)

Step 1: [5-(4-Bromo-phenyl)-3-methyl-isoxazol-4-yl]-carbamic acid 1-(2-methoxy-phenyl)-ethyl ester: Prepared according to the procedure described in Example 1, Step 5 using 5-(4-bromo-phenyl)-3-methyl-isoxazole-4-carboxylic acid and 1-(2-methoxyphenyl)ethanol.

Step 2: 1-(4'-{4-[1-(2-Methoxy-phenyl)-ethoxycarbonylamino]-3-methyl-isoxazol-5-yl}-biphenyl-4-yl)-cyclopropanecarboxylic acid ethyl ester: Prepared according to the procedure described in Example 6, Step 3 using [5-(4-bromo-phenyl)-3-methyl-isoxazol-4-yl]-carbamic acid 1-(2-methoxy-phenyl)-ethyl ester and 1-[4-(4,4,5,5-tetramethyl-[1,3,2]dioxaborolan-2-yl)-phenyl]-cyclopropanecarboxylic acid ethyl ester.

Step 3: 1-(4'-{4-[1-(2-Methoxy-phenyl)-ethoxycarbonylamino]-3-methyl-isoxazol-5-yl}-biphenyl-4-yl)-cyclopropanecarboxylic acid: Prepared according to the procedure described in Example 6, Step 4 using 1-(4'-{4-[1-(2-methoxy-phenyl)-ethoxycarbonylamino]-3-methyl-isoxazol-5-yl}-biphenyl-4-yl)-cyclopropanecarboxylic acid ethyl ester Example 13

Synthesis of 1-(4'-{3-Methyl-4-[1-(4-trifluoromethyl-phenyl)-ethoxycarbonylamino]-isoxazol-5-yl}-biphenyl-4-yl)-cyclopropanecarboxylic acid (Compound 13)

Step 1: [5-(4-Bromo-phenyl)-3-methyl-isoxazol-4-yl]-carbamic acid 1-(4-trifluoromethyl-phenyl)-ethyl ester: Prepared according to the procedure described in Example 1, Step 5 using 5-(4-bromo-phenyl)-3-methyl-isoxazole-4-carboxylic acid and 1-[4-(trifluoromethyl)phenyl]ethanol.

Step 2: 1-(4'-{3-Methyl-4-[1-(4-trifluoromethyl-phenyl)-ethoxycarbonylamino]-isoxazol-5-yl}-biphenyl-4-yl)-cyclopropanecarboxylic acid ethyl ester: Prepared according to the procedure described in Example 6, Step 3 using [5-(4-bromo-phenyl)-3-methyl-isoxazol-4-yl]-carbamic acid 1-(4-trifluoromethyl-phenyl)-ethyl ester and 1-[4-(4,4,5,5-tetramethyl-[1,3,2]dioxaborolan-2-yl)-phenyl]-cyclopropanecarboxylic acid ethyl ester; the isolated material was then purified by preparative HPLC, using a chiral column (95:5 hexanes:EtOAc) to provide enantiomer A and enantiomer B. Enantiomer A had a retention time of 30 minutes, enantiomer B had a retention time of 50 minutes.

Step 3: 1-(4'-{3-Methyl-4-[1-(4-trifluoromethyl-phenyl)-ethoxycarbonylamino]-isoxazol-5-yl}-biphenyl-4-yl)-cyclopropanecarboxylic acid: Prepared according to the procedure described in Example 6, Step 4 using enantiomer A from Example 13, Step 2 (1-(4'-{3-methyl-4-[1-(4-trifluoromethyl-phenyl)-ethoxycarbonylamino]-isoxazol-5-yl}-biphenyl-4-yl)-cyclopropanecarboxylic acid ethyl ester).

Example 14

Synthesis of 1-(4'-{3-Methyl-4-[1-(4-trifluoromethyl-phenyl)-ethoxycarbonylamino]-isoxazol-5-yl}-biphenyl-4-yl)-cyclopropanecarboxylic acid (Compound 14)

Prepared according to the procedure described in Example 6, Step 4 using enantiomer B from Example 13, Step 2 (1-(4'-{3-Methyl-4-[1-(4-trifluoromethyl-phenyl)-ethoxycarbonylamino]-isoxazol-5-yl}-biphenyl-4-yl)-cyclopropanecarboxylic acid ethyl ester).

Example 15

Synthesis of 1-(4'-{4-[1-(3-Cyano-phenyl)-ethoxycarbonylamino]-3-methyl-isoxazol-5-yl}-biphenyl-4-yl)-cyclopropanecarboxylic acid (Compound 15)

Step 1: 3-(1-Hydroxy-ethyl)-benzonitrile: To a solution of 3-acetylbenzonitrile (1 equivalent) in methanol at room temperature was added sodium borohydride (approx. 1.67 equivalents), and the reaction was stirred for approximately 20 minutes. Aqueous work-up provided the title compound.

Step 2: [5-(4-Bromo-phenyl)-3-methyl-isoxazol-4-yl]carbamic acid 1-(3-cyano-phenyl)-ethyl ester: Prepared according to the procedure described in Example 1, Step 5 using 5-(4-bromo-phenyl)-3-methyl-isoxazole-4-carboxylic acid and 3-(1-hydroxy-ethyl)-benzonitrile.

Step 3: 1-(4'-{4-[1-(3-Cyano-phenyl)-ethoxycarbonylamino]-3-methyl-isoxazol-5-yl}-biphenyl-4-yl)-cyclopropanecarboxylic acid ethyl ester: Prepared according to the procedure described in Example 6, Step 3 using [5-(4-bromo-phenyl)-3-methyl-isoxazol-4-yl]-carbamic acid 1-(3-cyano-phenyl)-ethyl ester and 1-[4-(4,4,5,5-tetramethyl-[1,3,2]dioxaborolan-2-yl)-phenyl]-cyclopropanecarboxylic acid ethyl ester.

Step 4: 1-(4'-{4-[1-(3-Cyano-phenyl)-ethoxycarbonylamino]-3-methyl-isoxazol-5-yl}-biphenyl-4-yl)-cyclopropanecarboxylic acid: Prepared according to the procedure described in Example 6, Step 4 using 1-(4'-{4-[1-(3-cyano-phenyl)-ethoxycarbonylamino]-3-methyl-isoxazol-5-yl}-biphenyl-4-yl)-cyclopropanecarboxylic acid ethyl ester.

Example 16

Synthesis of 1-{4'-[3-Methyl-4-((R)-1-p-tolyl-ethoxycarbonylamino)-isoxazol-5-yl]-biphenyl-4-yl}-cyclopropanecarboxylic acid (Compound 16)

Step 1: (R)-1-p-Tolyl-ethanol: Prepared according to the procedure described in Example 2, Step 5 using 4'-methylacetophenone.

Step 2: [5-(4-Bromo-phenyl)-3-methyl-isoxazol-4-yl]carbamic acid (R)-1-p-tolyl-ethyl ester: Prepared according to the procedure described in Example 1, Step 5 using 5-(4-bromo-phenyl)-3-methyl-isoxazole-4-carboxylic acid and (R)-1-p-tolyl-ethanol.

Step 3: 1-{4'-[3-Methyl-4-((R)-1-p-tolyl-ethoxycarbonylamino)-isoxazol-5-yl]-biphenyl-4-yl}-cyclopropanecarboxylic acid ethyl ester: Prepared according to the procedure described in Example 6, Step 3 using [5-(4-bromo-phenyl)-3-methyl-isoxazol-4-yl]-carbamic acid (R)-1-p-tolyl-ethyl ester and 1-[4-(4,4,5,5-tetramethyl-[1,3,2]dioxaborolan-2-yl)-phenyl]-cyclopropanecarboxylic acid ethyl ester.

Step 4: 1-{4'-[3-Methyl-4-((R)-1-p-tolyl-ethoxycarbonylamino)-isoxazol-5-yl]-biphenyl-4-yl}-cyclopropanecarboxylic acid: Prepared according to the procedure described in Example 6, Step 4 using 1-{4'-[3-methyl-4-((R)-1-p-tolyl-ethoxycarbonylamino)-isoxazol-5-yl]-biphenyl-4-yl}-cyclopropanecarboxylic acid ethyl ester.

Example 17

Synthesis of 1-{4'-[3-Methyl-4-((R)-1-m-tolyl-ethoxycarbonylamino)-isoxazol-5-yl]-biphenyl-4-yl}-cyclopropanecarboxylic acid (Compound 17)

Step 1: (R)-1-m-Tolyl-ethanol: Prepared according to the procedure described in Example 2, Step 5 using 3'-methylacetophenone.

Step 2: [5-(4-Bromo-phenyl)-3-methyl-isoxazol-4-yl]-carbamic acid (R)-1-m-tolyl-ethyl ester: Prepared according to the procedure described in Example 1, Step 5 using 5-(4-bromo-phenyl)-3-methyl-isoxazole-4-carboxylic acid and (R)-1-m-tolyl-ethanol.

Step 3: 1-{4'-[3-Methyl-4-((R)-1-m-tolyl-ethoxycarbonylamino)-isoxazol-5-yl]-biphenyl-4-yl}-cyclopropanecarboxylic acid ethyl ester: Prepared according to the procedure described in Example 6, Step 3 using [5-(4-bromo-phenyl)-3-methyl-isoxazol-4-yl]-carbamic acid (R)-1-m-tolyl-ethyl ester and 1-[4-(4,4,5,5-tetramethyl-[1,3,2]dioxaborolan-2-yl)-phenyl]-cyclopropanecarboxylic acid ethyl ester.

Step 4: 1-{4'-[3-Methyl-4-((R)-1-m-tolyl-ethoxycarbonylamino)-isoxazol-5-yl]-biphenyl-4-yl}-cyclopropanecarboxylic acid: Prepared according to the procedure described in Example 6, Step 4 using 1-{4'-[3-methyl-4-((R)-1-m-tolyl-ethoxycarbonylamino)-isoxazol-5-yl]-biphenyl-4-yl}-cyclopropanecarboxylic acid ethyl ester.

Example 18

Synthesis of 1-(4'-{4-[(R)-1-(4-Cyano-phenyl)-ethoxycarbonylamino]-3-methyl-isoxazol-5-yl}-biphenyl-4-yl)-cyclopropanecarboxylic acid (Compound 18)

Step 1: 4-((R)-1-Hydroxy-ethyl)-benzonitrile: Prepared according to the procedure described in Example 2, Step 5 using 4-acetylbenzonitrile.

Step 2: [5-(4-Bromo-phenyl)-3-methyl-isoxazol-4-yl]-carbamic acid (R)-1-(4-cyano-phenyl)-ethyl ester: Prepared according to the procedure described in Example 1, Step 5 using 5-(4-bromo-phenyl)-3-methyl-isoxazole-4-carboxylic acid and 4-((R)-1-hydroxy-ethyl)-benzonitrile.

Step 3: 1-(4'-{4-[(R)-1-(4-Cyano-phenyl)-ethoxycarbonylamino]-3-methyl-isoxazol-5-yl}-biphenyl-4-yl)-cyclopropanecarboxylic acid ethyl ester: Prepared according to the procedure described in Example 6, Step 3 using [5-(4-bromo-phenyl)-3-methyl-isoxazol-4-yl]-carbamic acid (R)-1-(4-cyano-phenyl)-ethyl ester and 1-[4-(4,4,5,5-tetramethyl-[1,3,2]dioxaborolan-2-yl)-phenyl]-cyclopropanecarboxylic acid ethyl ester.

Step 4: 1-(4'-{4-[(R)-1-(4-Cyano-phenyl)-ethoxycarbonylamino]-3-methyl-isoxazol-5-yl}-biphenyl-4-yl)-cyclopropanecarboxylic acid: Prepared according to the procedure described in Example 6, Step 4 using 1-(4'-{4-[(R)-1-(4-cyano-phenyl)-ethoxycarbonylamino]-3-methyl-isoxazol-5-yl}-biphenyl-4-yl)-cyclopropanecarboxylic acid ethyl ester.

Example 19

Synthesis of 1-(4'-{4-[(R)-1-(2-Cyano-phenyl)-ethoxycarbonylamino]-3-methyl-isoxazol-5-yl}-biphenyl-4-yl)-cyclopropanecarboxylic acid (Compound 19)

Step 1: 2-((R)-1-Hydroxy-ethyl)-benzonitrile: Prepared according to the procedure described in Example 2, Step 5 using 2-acetylbenzenecarbonitrile.

Step 2: [5-(4-Bromo-phenyl)-3-methyl-isoxazol-4-yl]-carbamic acid (R)-1-(2-cyano-phenyl)-ethyl ester: Prepared according to the procedure described in Example 1, Step 5 using 5-(4-bromo-phenyl)-3-methyl-isoxazole-4-carboxylic acid and 2-((R)-1-hydroxy-ethyl)-benzonitrile.

Step 3: 1-(4'-{4-[(R)-1-(2-Cyano-phenyl)-ethoxycarbonylamino]-3-methyl-isoxazol-5-yl}-biphenyl-4-yl)-cyclopropanecarboxylic acid ethyl ester: Prepared according to the procedure described in Example 6, Step 3 using [5-(4-bromo-phenyl)-3-methyl-isoxazol-4-yl]-carbamic acid (R)-1-(2-cyano-phenyl)-ethyl ester and 1-[4-(4,4,5,5-tetramethyl-[1,3,2]dioxaborolan-2-yl)-phenyl]-cyclopropanecarboxylic acid ethyl ester.

Step 4: 1-(4'-{4-[(R)-1-(2-Cyano-phenyl)-ethoxycarbonylamino]-3-methyl-isoxazol-5-yl}-biphenyl-4-yl)-cyclopropanecarboxylic acid: Prepared according to the procedure described in Example 6, Step 4 using 1-(4'-{4-[(R)-1-(2-cyano-phenyl)-ethoxycarbonylamino]-3-methyl-isoxazol-5-yl}-biphenyl-4-yl)-cyclopropanecarboxylic acid ethyl ester.

Example 20

Synthesis of 1-{4'-[4-((R)-1-Cyclobutyl-ethoxycarbonylamino)-3-methyl-isoxazol-5-yl]-biphenyl-4-yl}-cyclopropanecarboxylic acid (Compound 20)

Step 1: (R)-1-Cyclobutyl-ethanol: Prepared according to the procedure described in Example 2, Step 5 using cyclobutyl methyl ketone.
Step 2: [5-(4-Bromo-phenyl)-3-methyl-isoxazol-4-yl]-carbamic acid (R)-1-cyclobutyl-ethyl ester: Prepared according to the procedure described in Example 1, Step 5 using 5-(4-bromo-phenyl)-3-methyl-isoxazole-4-carboxylic acid and (R)-1-cyclobutyl-ethanol.
Step 3: 1-{4'-[4-((R)-1-Cyclobutyl-ethoxycarbonylamino)-3-methyl-isoxazol-5-yl]-biphenyl-4-yl}-cyclopropanecarboxylic acid ethyl ester: Prepared according to the procedure described in Example 1, Step 6 using [5-(4-bromo-phenyl)-3-methyl-isoxazol-4-yl]-carbamic acid (R)-1-cyclobutyl-ethyl ester and 1-[4-(4,4,5,5-tetramethyl-[1,3,2]dioxaborolan-2-yl)-phenyl]-cyclopropanecarboxylic acid ethyl ester.
Step 4: 1-{4'-[4-((R)-1-Cyclobutyl-ethoxycarbonylamino)-3-methyl-isoxazol-5-yl]-biphenyl-4-yl}-cyclopropanecarboxylic acid: Prepared according to the procedure described in Example 2, Step 8 using 1-{4'-[4-((R)-1-cyclobutyl-ethoxycarbonylamino)-3-methyl-isoxazol-5-yl]-biphenyl-4-yl}-cyclopropanecarboxylic acid ethyl ester.

Example 21

Synthesis of 1-(4'-{4-[1-(2-Chloro-cyclohex-1-enyl)-ethoxycarbonylamino]-3-methyl-isoxazol-5-yl}-biphenyl-4-yl)-cyclopropanecarboxylic acid (Compound 21)

Step 1: 2-Chloro-cyclohex-1-enecarbaldehyde: To a solution of cyclohexanone (1.34 g, 13.6 mmol) in toluene at room temperature was added DMF (1.58 mL, 20.5 mmol) and phosphorus oxychloride (1.88 mL, 20.5 mmol). The reaction was stirred overnight at room temperature, and then diluted with H$_2$O and stirred for 30 minutes. 4N Aqueous NaOH (10 mL) was added, and the mixture was extracted with EtOAc. The combined organic layers were washed with saturated aqueous NH$_4$Cl, dried over MgSO$_4$, filtered, and concentrated to give the title compound.
Step 2: 1-(2-Chloro-cyclohex-1-enyl)-ethanol: To a solution of 2-chloro-cyclohex-1-enecarbaldehyde (13.6 mmol) in THF at 0° C. was added methyl magnesium bromide (3M in THF; 5.4 mL, 16.32 mmol). The reaction was stirred under N$_2$ for 1 hour, and then iPrOH (2 mL) was added. The mixture was concentrated, and the residue was diluted with 1N aqueous HCl and extracted with EtOAc. The combined organic layers were washed with saturated aqueous NH$_4$Cl, dried over MgSO$_4$, filtered, and concentrated, and the crude material was purified by silica gel chromatography to give the title compound.
Step 3: 5-[4'-(1-Ethoxycarbonyl-cyclopropyl)-biphenyl-4-yl]-3-methyl-isoxazole-4-carboxylic acid: Prepared according to the procedure described in Example 1, Step 6 using 5-(4-bromo-phenyl)-3-methyl-isoxazole-4-carboxylic acid and 1-[4-(4,4,5,5-tetramethyl-[1,3,2]dioxaborolan-2-yl)-phenyl]-cyclopropanecarboxylic acid ethyl ester.
Step 4: 1-(4'-{4-[1-(2-Chloro-cyclohex-1-enyl)-ethoxycarbonylamino]-3-methyl-isoxazol-5-yl}-biphenyl-4-yl)-cyclopropanecarboxylic acid ethyl ester: Prepared according to the procedure described in Example 1, Step 5 using 5-[4'-(1-ethoxycarbonyl-cyclopropyl)-biphenyl-4-yl]-3-methyl-isoxazole-4-carboxylic acid and 1-(2-chloro-cyclohex-1-enyl)-ethanol.
Step 5: 1-(4'-{4-[1-(2-Chloro-cyclohex-1-enyl)-ethoxycarbonylamino]-3-methyl-isoxazol-5-yl}-biphenyl-4-yl)-cyclopropanecarboxylic acid: Prepared according to the procedure described in Example 2, Step 8 using 1-(4'-{4-[1-(2-chloro-cyclohex-1-enyl)-ethoxycarbonylamino]-3-methyl-isoxazol-5-yl}-biphenyl-4-yl)-cyclopropanecarboxylic acid ethyl ester.

Example 22

Synthesis of 1-(4'-{3-Methyl-4-[(R)-1-(3-trifluoromethyl-phenyl)-ethoxycarbonylamino]-isoxazol-5-yl}-biphenyl-4-yl)-cyclopropanecarboxylic acid (Compound 22)

Step 1: (R)-1-(3-Trifluoromethyl-phenyl)-ethanol: Prepared according to the procedure described in Example 2, Step 5 using 3'-(trifluoromethyl)acetophenone.
Step 2: [5-(4-Bromo-phenyl)-3-methyl-isoxazol-4-yl]-carbamic acid (R)-1-(3-trifluoromethyl-phenyl)-ethyl ester: Prepared according to the procedure described in Example 1, Step 5 using 5-(4-bromo-phenyl)-3-methyl-isoxazole-4-carboxylic acid and (R)-1-(3-trifluoromethyl-phenyl)-ethanol.
Step 3: 1-(4'-{3-Methyl-4-[(R)-1-(3-trifluoromethyl-phenyl)-ethoxycarbonylamino]-isoxazol-5-yl}-biphenyl-4-yl)-cyclopropanecarboxylic acid ethyl ester: Prepared according to the procedure described in Example 6, Step 3 using [5-(4-bromo-phenyl)-3-methyl-isoxazol-4-yl]-carbamic acid (R)-1-(3-trifluoromethyl-phenyl)-ethyl ester and 1-[4-(4,4,5,5-tetramethyl-[1,3,2]dioxaborolan-2-yl)-phenyl]-cyclopropanecarboxylic acid ethyl ester.
Step 4: 1-(4'-{3-Methyl-4-[(R)-1-(3-trifluoromethyl-phenyl)-ethoxycarbonylamino]-isoxazol-5-yl}-biphenyl-4-yl)-cyclopropanecarboxylic acid: Prepared according to the procedure described in Example 6, Step 4 using 1-(4'-{3-methyl-4-[(R)-1-(3-trifluoromethyl-phenyl)-ethoxycarbonylamino]-isoxazol-5-yl}-biphenyl-4-yl)-cyclopropanecarboxylic acid ethyl ester.

Example 23

Synthesis of 1-(4'-{4-[(R)-1-(3-Methoxy-phenyl)-ethoxycarbonylamino]-3-methyl-isoxazol-5-yl}-biphenyl-4-yl)-cyclopropanecarboxylic acid (Compound 23)

Step 1: (R)-1-(3-Methoxy-phenyl)-ethanol: Prepared according to the procedure described in Example 2, Step 5 using 3'-methoxyacetophenone.
Step 2: [5-(4-Bromo-phenyl)-3-methyl-isoxazol-4-yl]carbamic acid (R)-1-(3-methoxy-phenyl)-ethyl ester: Prepared according to the procedure described in Example 1, Step 5 using 5-(4-bromo-phenyl)-3-methyl-isoxazole-4-carboxylic acid and (R)-1-(3-methoxy-phenyl)-ethanol.
Step 3: 1-(4'-{4-[(R)-1-(3-Methoxy-phenyl)-ethoxycarbonylamino]-3-methyl-isoxazol-5-yl}-biphenyl-4-yl)-cyclopropanecarboxylic acid ethyl ester: Prepared according to the procedure described in Example 6, Step 3 using [5-(4-bromophenyl)-3-methyl-isoxazol-4-yl]-carbamic acid (R)-1-(3-methoxy-phenyl)-ethyl ester and 1-[4-(4,4,5,5-tetramethyl-[1,3,2]dioxaborolan-2-yl)-phenyl]-cyclopropanecarboxylic acid ethyl ester.

Step 4: 1-(4'-{4-[(R)-1-(3-Methoxy-phenyl)-ethoxycarbonylamino]-3-methyl-isoxazol-5-yl}-biphenyl-4-yl)-cyclopropanecarboxylic acid: Prepared according to the procedure described in Example 6, Step 4 using 1-(4'-{4-[(R)-1-(3-methoxy-phenyl)-ethoxycarbonylamino]-3-methyl-isoxazol-5-yl}-biphenyl-4-yl)-cyclopropanecarboxylic acid ethyl ester.

Example 24

Synthesis of 1-(4'-{4-[(R)-1-(4-Methoxy-phenyl)-ethoxycarbonylamino]-3-methyl-isoxazol-5-yl}-biphenyl-4-yl)-cyclopropanecarboxylic acid (Compound 24)

Step 1: (R)-1-(4-Methoxy-phenyl)-ethanol: Prepared according to the procedure described in Example 2, Step 5 using 4'-methoxyacetophenone.

Step 2: [5-(4-Bromo-phenyl)-3-methyl-isoxazol-4-yl]-carbamic acid (R)-1-(4-methoxy-phenyl)-ethyl ester: Prepared according to the procedure described in Example 1, Step 5 using 5-(4-bromo-phenyl)-3-methyl-isoxazole-4-carboxylic acid and (R)-1-(4-methoxy-phenyl)-ethanol.

Step 3: 1-(4'-{4-[(R)-1-(4-Methoxy-phenyl)-ethoxycarbonylamino]-3-methyl-isoxazol-5-yl}-biphenyl-4-yl)-cyclopropanecarboxylic acid ethyl ester: Prepared according to the procedure described in Example 6, Step 3 using [5-(4-bromo-phenyl)-3-methyl-isoxazol-4-yl]-carbamic acid (R)-1-(4-methoxy-phenyl)-ethyl ester and 1-[4-(4,4,5,5-tetramethyl-[1,3,2]dioxaborolan-2-yl)-phenyl]-cyclopropanecarboxylic acid ethyl ester.

Step 4: 1-(4'-{4-[(R)-1-(4-Methoxy-phenyl)-ethoxycarbonylamino]-3-methyl-isoxazol-5-yl}-biphenyl-4-yl)-cyclopropanecarboxylic acid: Prepared according to the procedure described in Example 6, Step 4 using 1-(4'-{4-[(R)-1-(4-methoxy-phenyl)-ethoxycarbonylamino]-3-methyl-isoxazol-5-yl}-biphenyl-4-yl)-cyclopropanecarboxylic acid ethyl ester.

Example 25

Synthesis of 1-(4'-{4-[1-(3-Bromo-phenyl)-ethoxycarbonylamino]-3-methyl-isoxazol-5-yl}-biphenyl-4-yl)-cyclopropanecarboxylic acid (Compound 25)

Step 1: 1-(4'-{4-[1-(3-Bromo-phenyl)-ethoxycarbonylamino]-3-methyl-isoxazol-5-yl}-biphenyl-4-yl)-cyclopropanecarboxylic acid ethyl ester: Prepared according to the procedure described in Example 1, Step 5 using 5-[4'-(1-ethoxycarbonyl-cyclopropyl)-biphenyl-4-yl]-3-methyl-isoxazole-4-carboxylic acid and 3-bromo-alpha-methylbenzyl alcohol.

Step 2: 1-(4'-{4-[1-(3-Bromo-phenyl)-ethoxycarbonylamino]-3-methyl-isoxazol-5-yl}-biphenyl-4-yl)-cyclopropanecarboxylic acid: Prepared according to the procedure described in Example 2, Step 8 using 1-(4'-{4-[1-(3-bromo-phenyl)-ethoxycarbonylamino]-3-methyl-isoxazol-5-yl}-biphenyl-4-yl)-cyclopropanecarboxylic acid ethyl ester.

Example 26

Synthesis of 1-(4'-{4-[1-(3-Chloro-phenyl)-ethoxycarbonylamino]-3-methyl-isoxazol-5-yl}-biphenyl-4-yl)-cyclopropanecarboxylic acid (Compound 26)

Step 1: 1-(4'-{4-[1-(3-Chloro-phenyl)-ethoxycarbonylamino]-3-methyl-isoxazol-5-yl}-biphenyl-4-yl)-cyclopropanecarboxylic acid ethyl ester: Prepared according to the procedure described in Example 1, Step 5 using 5-[4'-(1-ethoxycarbonyl-cyclopropyl)-biphenyl-4-yl]-3-methyl-isoxazole-4-carboxylic acid and 1-(3-chlorophenyl)ethanol.

Step 2: 1-(4'-{4-[1-(3-Chloro-phenyl)-ethoxycarbonylamino]-3-methyl-isoxazol-5-yl}-biphenyl-4-yl)-cyclopropanecarboxylic acid: Prepared according to the procedure described in Example 2, Step 8 using 1-(4'-{4-[1-(3-chloro-phenyl)-ethoxycarbonylamino]-3-methyl-isoxazol-5-yl}-biphenyl-4-yl)-cyclopropanecarboxylic acid ethyl ester.

Example 27

Synthesis of 1-{4'-[3-Methyl-4-((S)-1-phenyl-ethoxycarbonylamino)-isoxazol-5-yl]-biphenyl-4-yl}-cyclopropanecarboxylic acid (Compound 27)

Step 1: (S)-[5-(4-Bromo-phenyl)-3-methyl-isoxazol-4-yl]-carbamic acid 1-phenyl-ethyl ester: Prepared according to the procedure described in Example 1, Step 5 using 5-(4-bromo-phenyl)-3-methyl-isoxazole-4-carboxylic acid and (S)-1-phenylethanol (commercially available or prepared using procedures described herein or in the literature: e.g. E. J. Corey et al. *J. Am. Chem.* 1987, 109, 5551-5553).

Step 2: 1-{4'-[3-Methyl-4-((S)-1-phenyl-ethoxycarbonylamino)-isoxazol-5-yl]-biphenyl-4-yl}-cyclopropanecarboxylic acid ethyl ester: Prepared according to the procedure described in Example 1, Step 6 using (S)-[5-(4-bromo-phenyl)-3-methyl-isoxazol-4-yl]-carbamic acid 1-phenyl-ethyl ester and 1-[4-(4,4,5,5-tetramethyl-[1,3,2]dioxaborolan-2-yl)-phenyl]-cyclopropanecarboxylic acid ethyl ester.

Step 3: 1-{4'-[3-Methyl-4-((S)-1-phenyl-ethoxycarbonylamino)-isoxazol-5-yl]-biphenyl-4-yl}-cyclopropanecarboxylic acid: Prepared according to the procedure described in Example 2, Step 8 using 1-{4'-[3-methyl-4-((S)-1-phenyl-ethoxycarbonylamino)-isoxazol-5-yl]-biphenyl-4-yl}-cyclopropanecarboxylic acid ethyl ester.

Example 28

Synthesis of 1-(4'-{4-[1-(3-Hydroxy-phenyl)-ethoxycarbonylamino]-3-methyl-isoxazol-5-yl}-biphenyl-4-yl)-cyclopropanecarboxylic acid (Compound 28)

Step 1: 1-[3-(tert-Butyl-dimethyl-silanyloxy)-phenyl]-ethanone: To a solution of 3'-hydroxyacetophenone (0.500 g, 3.67 mmol) and imidazole (0.500 g, 7.34 mmol) in $CH_2Cl_2$ (5 mL) was added tert-butyldimethylsilyl chloride (0.609 g, 4.04 mmol), and the reaction was stirred for 1 hour at room temperature. The mixture was partitioned between $CH_2Cl_2$ and $H_2O$, and the aqueous layer was separated and extracted with $CH_2Cl_2$. The combined organic layers were dried over $MgSO_4$, filtered, and concentrated to give the title compound.

Step 2: 1-[3-(tert-Butyl-dimethyl-silanyloxy)-phenyl]ethanol: 1-[3-(tert-Butyl-dimethyl-silanyloxy)-phenyl]-ethanone (3.67 mmol) in MeOH (5 mL) was treated with sodium borohydride (0.139 g, 3.67 mmol). The reaction was stirred for 20 minutes, and then standard work-up provided the title compound.

Step 3: [5-(4-Bromo-phenyl)-3-methyl-isoxazol-4-yl]-carbamic acid 1-[3-(tert-butyl-dimethyl-silanyloxy)-phenyl]-ethyl ester: Prepared according to the procedure described in Example 1, Step 5 using 5-(4-bromo-phenyl)-3-methyl-isoxazole-4-carboxylic acid and 1-[3-(tert-butyl-dimethyl-silanyloxy)-phenyl]-ethanol.

Step 4: 1-[4'-(4-{1-[3-(tert-Butyl-dimethyl-silanyloxy)-phenyl]-ethoxycarbonylamino}-3-methyl-isoxazol-5-yl)-biphenyl-4-yl]-cyclopropanecarboxylic acid ethyl ester: Prepared according to the procedure described in Example 1, Step 6 using [5-(4-bromo-phenyl)-3-methyl-isoxazol-4-yl]-carbamic acid 1-[3-(tert-butyl-dimethyl-silanyloxy)-phenyl]-ethyl ester and 1-[4-(4,4,5,5-tetramethyl-[1,3,2]dioxaborolan-2-yl)-phenyl]-cyclopropanecarboxylic acid ethyl ester.

Step 5: 1-(4'-{4-[1-(3-Hydroxy-phenyl)-ethoxycarbonylamino]-3-methyl-isoxazol-5-yl}-biphenyl-4-yl)-cyclopropanecarboxylic acid: 1-[4'-(4-{1-[3-(tert-Butyl-dimethyl-silanyloxy)-phenyl]-ethoxycarbonylamino}-3-methyl-isoxazol-5-yl)-biphenyl-4-yl]-cyclopropanecarboxylic acid ethyl ester (0.400 g, 0.63 mmol) in 3:1 MeOH:H$_2$O (10 mL) was treated with excess lithium hydroxide. The reaction was stirred overnight at 60° C., and then acidified and extracted with EtOAc. The combined organic layers were dried over MgSO$_4$, filtered, and concentrated, and the residue was purified by preparative HPLC to give the title compound.

Example 29

Synthesis of 1-{4'-[3-Ethyl-4-((R)-1-phenyl-ethoxycarbonylamino)-isoxazol-5-yl]-biphenyl-4-yl}-cyclopropanecarboxylic acid (Compound 29)

Step 1: 2-(4-Bromo-benzoyl)-3-oxo-pentanoic acid methyl ester: Prepared according to the procedure described in Example 1, Step 2 using 4-bromobenzoyl chloride and methyl 3-oxovalerate; sodium tert-butoxide was used in place of pyridine.

Step 2: 5-(4-Bromo-phenyl)-3-ethyl-isoxazole-4-carboxylic acid methyl ester: Prepared according to the procedure described in Example 1, Step 3 using 2-(4-bromo-benzoyl)-3-oxo-pentanoic acid methyl ester and hydroxylamine hydrochloride.

Step 3: 5-(4-Bromo-phenyl)-3-ethyl-isoxazole-4-carboxylic acid: Prepared according to the procedure described in Example 1, Step 4 using 5-(4-bromo-phenyl)-3-ethyl-isoxazole-4-carboxylic acid methyl ester.

Step 4: [5-(4-Bromo-phenyl)-3-ethyl-isoxazol-4-yl]-carbamic acid (R)-1-phenyl-ethyl ester: Prepared according to the procedure described in Example 1, Step 5 using the following starting materials: 5-(4-bromo-phenyl)-3-ethyl-isoxazole-4-carboxylic acid and (R)-1-phenyl-ethanol.

Step 5: 1-{4'-[3-Ethyl-4-((R)-1-phenyl-ethoxycarbonylamino)-isoxazol-5-yl]-biphenyl-4-yl}-cyclopropanecarboxylic acid ethyl ester: Prepared according to the procedure described in Example 1, Step 6 using [5-(4-bromo-phenyl)-3-ethyl-isoxazol-4-yl]-carbamic acid (R)-1-phenyl-ethyl ester and 1-[4-(4,4,5,5-tetramethyl-[1,3,2]dioxaborolan-2-yl)-phenyl]-cyclopropanecarboxylic acid ethyl ester.

Step 6: 1-{4'-[3-Ethyl-4-((R)-1-phenyl-ethoxycarbonylamino)-isoxazol-5-yl]-biphenyl-4-yl}-cyclopropanecarboxylic acid: Prepared according to the procedure described in Example 2, Step 8 using 1-{4'-[3-ethyl-4-((R)-1-phenyl-ethoxycarbonylamino)-isoxazol-5-yl]-biphenyl-4-yl}-cyclopropanecarboxylic acid ethyl ester.

Example 30

Synthesis of 1-(4'-{3-Ethyl-4-[(R)-1-(3-trifluoromethyl-phenyl)-ethoxycarbonylamino]-isoxazol-5-yl}-biphenyl-4-yl)-cyclopropanecarboxylic acid (Compound 30)

Step 1: [5-(4-Bromo-phenyl)-3-ethyl-isoxazol-4-yl]-carbamic acid (R)-1-(3-trifluoromethyl-phenyl)-ethyl ester: Prepared according to the procedure described in Example 1, Step 5 using 5-(4-bromo-phenyl)-3-ethyl-isoxazole-4-carboxylic acid and (R)-1-(3-trifluoromethyl-phenyl)-ethanol.

Step 2: 1-(4'-{3-Ethyl-4-[(R)-1-(3-trifluoromethyl-phenyl)-ethoxycarbonylamino]-isoxazol-5-yl}-biphenyl-4-yl)-cyclopropanecarboxylic acid ethyl ester: Prepared according to the procedure described in Example 1, Step 6 using [5-(4-bromo-phenyl)-3-ethyl-isoxazol-4-yl]-carbamic acid (R)-1-(3-trifluoromethyl-phenyl)-ethyl ester and 1-[4-(4,4,5,5-tetramethyl-[1,3,2]dioxaborolan-2-yl)-phenyl]-cyclopropanecarboxylic acid ethyl ester.

Step 3: 1-(4'-{3-Ethyl-4-[(R)-1-(3-trifluoromethyl-phenyl)-ethoxycarbonylamino]-isoxazol-5-yl}-biphenyl-4-yl)-cyclopropanecarboxylic acid: Prepared according to the procedure described in Example 2, Step 8 using 1-(4'-{3-ethyl-4-[(R)-1-(3-trifluoromethyl-phenyl)-ethoxycarbonylamino]-isoxazol-5-yl}-biphenyl-4-yl)-cyclopropanecarboxylic acid ethyl ester.

Example 31

Synthesis of 1-{4'-[3-Methyl-4-((1-phenyl-ethoxy-d9)-carbonylamino)-isoxazol-5-yl]-biphenyl-4-yl}-cyclopropanecarboxylic acid Step 1: 1-{4'-[3-Methyl-4-((1-phenyl-ethoxy-d9)-carbonylamino)-isoxazol-5-yl]-biphenyl-4-yl}-cyclopropanecarboxylic acid ethyl ester: Prepared according to the procedure described in Example 1, Step 5 using 5-[4'-(1-ethoxycarbonyl-cyclopropyl)-biphenyl-4-yl]-3-methyl-isoxazole-4-carboxylic acid and 1-phenylethanol-d9 (deuterated 1-phenylethanol obtained from Carbocore).

Step 2: Prepared according to the procedure described in Example 2, Step 8 using 1-{4'-[3-methyl-4-((1-phenyl-ethoxy-d9)-carbonylamino)-isoxazol-5-yl]-biphenyl-4-yl}-cyclopropanecarboxylic acid ethyl ester.

Example 32

Synthesis of 1-(3'-Methoxy-4'-{3-methyl-4-[(R)-1-(3-trifluoromethyl-phenyl)-ethoxycarbonylamino]-isoxazol-5-yl}-biphenyl-4-yl)-cyclopropanecarboxylic acid (Compound 31)

Step 1: 4-Bromo-2-methoxy-benzoyl chloride: To a suspension of 4-bromo-2-methoxybenzoic acid (2.5 g, 11.04 mmol) in CHCl$_3$ (20 mL) was added DMF (catalytic) and thionyl chloride (1.6 mL, 22.08 mmol). The reaction was stirred at 55° C. for 1 hour and then concentrated to dryness to give the title compound.

Step 2: 2-(4-Bromo-2-methoxy-benzoyl)-3-oxo-butyric acid methyl ester: Prepared according to the procedure described in Example 1, Step 2 using 4-bromo-2-methoxy-benzoyl chloride and 3-methylamino-but-2-enoic acid methyl ester.

Step 3: 5-(4-Bromo-2-methoxy-phenyl)-3-methyl-isoxazole-4-carboxylic acid methyl ester: Prepared according to the procedure described in Example 1, Step 3 using 2-(4-bromo-2-methoxy-benzoyl)-3-oxo-butyric acid methyl ester and hydroxylamine hydrochloride.

Step 4: 5-(4-Bromo-2-methoxy-phenyl)-3-methyl-isoxazole-4-carboxylic acid: Prepared according to the procedure described in Example 1, Step 4 using 5-(4-bromo-2-methoxy-phenyl)-3-methyl-isoxazole-4-carboxylic acid methyl ester.

Step 5: [5-(4-Bromo-2-methoxy-phenyl)-3-methyl-isoxazol-4-yl]-carbamic acid (R)-1-(3-trifluoromethyl-phenyl)-ethyl ester: Prepared according to the procedure described in Example 1, Step 5 using 5-(4-bromo-2-methoxy-phenyl)-3-methyl-isoxazole-4-carboxylic acid and (R)-1-(3-trifluoromethyl-phenyl)-ethanol.

Step 6: 1-(3'-Methoxy-4'-{3-methyl-4-[(R)-1-(3-trifluoromethyl-phenyl)-ethoxycarbonylamino]-isoxazol-5-yl}-biphenyl-4-yl)-cyclopropanecarboxylic acid ethyl ester: Prepared according to the procedure described in Example 1, Step 6 using [5-(4-bromo-2-methoxy-phenyl)-3-methyl-isoxazol-4-yl]-carbamic acid (R)-1-(3-trifluoromethyl-phenyl)-ethyl ester and 1-[4-(4,4,5,5-tetramethyl-[1,3,2]dioxaborolan-2-yl)-phenyl]-cyclopropanecarboxylic acid ethyl ester.

Step 7: 1-(3'-Methoxy-4'-{3-methyl-4-[(R)-1-(3-trifluoromethyl-phenyl)-ethoxycarbonylamino]-isoxazol-5-yl}-biphenyl-4-yl)-cyclopropanecarboxylic acid: Prepared according to the procedure described in Example 2, Step 8 using 1-(3'-methoxy-4'-{3-methyl-4-[(R)-1-(3-trifluoromethyl-phenyl)-ethoxycarbonylamino]-isoxazol-5-yl}-biphenyl-4-yl)-cyclopropanecarboxylic acid ethyl ester.

Example 33

Synthesis of 1-(4'-{4-[(R)-1-(3,5-Dibromo-phenyl)-ethoxycarbonylamino]-3-methyl-isoxazol-5-yl}-biphenyl-4-yl)-cyclopropanecarboxylic acid (Compound 32)

Step 1: 1-(3,5-Dibromo-phenyl)-ethanone: To a solution of 3,5-dibromobenzoic acid (2.5 g, 8.9 mmol) in $Et_2O$ (30 mL) at 0° C. was added methyllithium (1.6M in $Et_2O$; 12.3 mL, 19.6 mmol) dropwise. The reaction was stirred at 0° C. for 2 hours, and then worked-up with EtOAc and 10% aqueous HCl. The crude material was purified by silica gel chromatography to give the title compound.

Step 2: (R)-1-(3,5-Dibromo-phenyl)-ethanol: Prepared according to the procedure described in Example 2, Step 5 using 1-(3,5-dibromo-phenyl)-ethanone.

Step 3: 1-(4'-{4-[(R)-1-(3,5-Dibromo-phenyl)-ethoxycarbonylamino]-3-methyl-isoxazol-5-yl}-biphenyl-4-yl)-cyclopropanecarboxylic acid ethyl ester: Prepared according to the procedure described in Example 1, Step 5 using 5-[4'-(1-ethoxycarbonyl-cyclopropyl)-biphenyl-4-yl]-3-methyl-isoxazole-4-carboxylic acid and (R)-1-(3,5-cibromo-phenyl)-ethanol.

Step 4: 1-(4'-{4-[(R)-1-(3,5-Dibromo-phenyl)-ethoxycarbonylamino]-3-methyl-isoxazol-5-yl}-biphenyl-4-yl)-cyclopropanecarboxylic acid: Prepared according to the procedure described in Example 2, Step 8 using 1-(4'-{4-[(R)-1-(3,5-dibromo-phenyl)-ethoxycarbonylamino]-3-methyl-isoxazol-5-yl}-biphenyl-4-yl)-cyclopropanecarboxylic acid ethyl ester.

Example 34

Synthesis of {5-[4'-(1-Methanesulfonylaminocarbonyl-cyclopropyl)-biphenyl-4-yl]-3-methyl-isoxazol-4-yl}-carbamic acid (R)-1-phenyl-ethyl ester (Compound 35)

1-{4'-[3-Methyl-4-((R)-1-phenyl-ethoxycarbonylamino)-isoxazol-5-yl]-biphenyl-4-yl}-cyclopropanecarboxylic acid (0.1 g, 0.2 mmol), methanesulfonamide (0.08 g, 0.8 mmol), and N,N'-carbonyldiimidazole (0.15 g, 0.6 mmol) were combined in THF (4 mL). Diisopropylethylamine (0.5 mL) was added, and the reaction was stirred at 65° C. overnight. The mixture was acidified and extracted with $CH_2Cl_2$. The crude material was purified by silica gel chromatography (0-50% EtOAc in hexanes) to give the title compound.

Example 35

Synthesis of {5-[4'-(1-Benzenesulfonylaminocarbonyl-cyclopropyl)-biphenyl-4-yl]-3-methyl-isoxazol-4-yl}-carbamic acid (R)-1-phenyl-ethyl ester (Compound 36)

Prepared according to the procedure described in Example 34, Step 1 using 1-{4'-[3-methyl-4-(((R)-1-phenyl-ethoxycarbonylamino)-isoxazol-5-yl]-biphenyl-4-yl}-cyclopropanecarboxylic acid and benzenesulfonamide.

Example 36

Synthesis of {5-[4'-(1-Cyano-cyclopropyl)-biphenyl-4-yl]-3-methyl-isoxazol-4-yl}-carbamic acid (R)-1-phenyl-ethyl ester (Compound 37)

Step 1: 1-[4-(4,4,5,5-Tetramethyl-[1,3,2]dioxaborolan-2-yl)-phenyl]-cyclopropanecarbonitrile: Prepared according to the procedure described in Example 2, Step 4 using 1-(4-bromo-phenyl)-cyclopropanecarbonitrile and bis(pinacolato)diboron.

Step 2: {5-[4'-(1-Cyano-cyclopropyl)-biphenyl-4-yl]-3-methyl-isoxazol-4-yl}-carbamic acid (R)-1-phenyl-ethyl ester: Prepared according to the procedure described in Example 1, Step 6 using [5-(4-bromo-phenyl)-3-methyl-isoxazol-4-yl]-carbamic acid (R)-1-phenyl-ethyl ester and 1-[4-(4,4,5,5-tetramethyl-[1,3,2]dioxaborolan-2-yl)-phenyl]-cyclopropanecarbonitrile.

Example 37

Synthesis of (3-Methyl-5-{4'-[1-(5-oxo-2,5-dihydro-[1,2,4]oxadiazol-3-yl)-cyclopropyl]-biphenyl-4-yl}-isoxazol-4-yl)-carbamic acid (R)-1-phenyl-ethyl ester (Compound 38)

Step 1: (5-{4'-[1-(N-Hydroxycarbamimidoyl)-cyclopropyl]-biphenyl-4-yl}-3-methyl-isoxazol-4-yl)-carbamic acid (R)-1-phenyl-ethyl ester: {5-[4'-(1-Cyano-cyclopropyl)-biphenyl-4-yl]-3-methyl-isoxazol-4-yl}-carbamic acid (R)-1-phenyl-ethyl ester (0.307 g, 0.66 mmol), hydroxylamine hydrochloride (0.046 g, 0.67 mmol), and triethylamine (0.097 mL, 0.67 mmol) were combined in EtOH (7 mL), and the reaction was stirred at 50° C. overnight. Additional hydroxylamine hydrochloride (0.100 g, 1.45 mmol) and triethylamine (0.30 mL, 2.15 mmol) were added, and the reaction was stirred overnight. The mixture was then concentrated to provide the title compound.

Step 2: (3-Methyl-5-{4'-[1-(5-oxo-2,5-dihydro-[1,2,4]oxadiazol-3-yl)-cyclopropyl]-biphenyl-4-yl}-isoxazol-4-yl)-carbamic acid (R)-1-phenyl-ethyl ester: To (5-{4'-[1-(N-hydroxycarbamimidoyl)-cyclopropyl]-biphenyl-4-yl}-3-methyl-isoxazol-4-yl)-carbamic acid (R)-1-phenyl-ethyl ester (0.66 mmol) in CH$_2$Cl$_2$ (5 mL) was added triethylamine (0.19 mL, 1.32 mmol) and ethyl chloroformate (0.127 mL, 1.32 mmol), and the reaction was stirred overnight at room temperature. Additional triethylamine (0.19 mL, 1.32 mmol) was added, and the reaction was stirred for 6 hours. Additional triethylamine (0.19 mL, 1.32 mmol) was added, and the reaction was stirred until complete. The mixture was diluted with CH$_2$Cl$_2$ (20 mL) and washed with 10% aqueous citric acid, and then dried over MgSO$_4$, filtered, and concentrated. The residue was dissolved in toluene (10 mL), and the solution was refluxed for 3 days. After concentrating, the crude material was purified by silica gel chromatography (0-100% EtOAc in hexanes) to give the title compound.

Example 38

Synthesis of (3-Methyl-5-{4'-[1-(1H-tetrazol-5-yl)-cyclopropyl]-biphenyl-4-yl}-isoxazol-4-yl)-carbamic acid (R)-1-phenyl-ethyl ester (Compound 39)

{5-[4'-(1-Cyano-cyclopropyl)-biphenyl-4-yl]-3-methyl-isoxazol-4-yl}-carbamic acid (R)-1-phenyl-ethyl ester (0.385 g, 0.83 mmol) and N,N-dimethylethanolamine (0.101 mL, 1.0 mmol) were combined in diglyme (diethylene glycol dimethyl ether; 2 mL). Hydrochloric acid (4M in 1,4-dioxane; 4.2 mL) was added, and the reaction was stirred for 15 minutes. Additional N,N-dimethylethanolamine (0.221 mL, 2.2 mmol) was added, followed by sodium azide (0.098 g, 1.5 mmol), and the reaction was stirred at 120° C. for 24 hours. After cooling to room temperature, the mixture was diluted with CH$_2$Cl$_2$ (20 mL) and H$_2$O (10 mL). The organic layer was dried over MgSO$_4$, filtered, and concentrated, and the residue was purified by silica gel chromatography to give the title compound.

Example 39

Synthesis of {5-[4'-(1-Methanesulfonylaminocarbonyl-cyclopropyl)-biphenyl-4-yl]-3-methyl-isoxazol-4-yl}-carbamic acid (R)-1-(3-trifluoromethyl-phenyl)-ethyl ester (Compound 40)

Step 1: N-[1-(4-Bromo-phenyl)-cyclopropanecarbonyl]-methanesulfonamide: To a solution of 1-(4-bromo-phenyl)-cyclopropanecarboxylic acid (5.0 g, 20.7 mmol) in toluene (30 mL) was slowly added thionyl chloride (17.7 mL, 243 mmol), and the reaction was refluxed for 4 hours. The mixture was concentrated, and the crude material was dissolved in toluene (50 mL). Methanesulfonamide (11.41 g, 120 mmol) was added, followed by triethylamine (15 mL), and the reaction was refluxed for 3 hours. After cooling to room temperature, the mixture was poured in CH$_2$Cl$_2$ (200 mL) and washed with H$_2$O (150 mL). The organic layer was dried over MgSO$_4$, filtered, and concentrated, and the crude material was purified by silica gel chromatography to give the title compound.

Step 2: N-{1-[4-(4,4,5,5-Tetramethyl-[1,3,2]dioxaborolan-2-yl)-phenyl]-cyclopropanecarbonyl}-methanesulfonamide: Prepared according to the procedure described in Example 2, Step 4 using N-[1-(4-bromo-phenyl)-cyclopropanecarbonyl]-methanesulfonamide and bis(pinacolato)diboron.

Step 3: {5-[4'-(1-Methanesulfonylaminocarbonyl-cyclopropyl)-biphenyl-4-yl]-3-methyl-isoxazol-4-yl}-carbamic acid (R)-1-(3-trifluoromethyl-phenyl)-ethyl ester: Prepared according to the procedure described in Example 1, Step 6 using [5-(4-bromo-phenyl)-3-methyl-isoxazol-4-yl]-carbamic acid (R)-1-(3-trifluoromethyl-phenyl)-ethyl ester and N-{1-[4-(4,4,5,5-tetramethyl-[1,3,2]dioxaborolan-2-yl)-phenyl]-cyclopropanecarbonyl}-methanesulfonamide.

Example 40

Synthesis of {5-[4'-(1-Methanesulfonylaminocarbonyl-cyclopropyl)-3-methoxy-biphenyl-4-yl]-3-methyl-isoxazol-4-yl}-carbamic acid (R)-1-(3-trifluoromethyl-phenyl)-ethyl ester (Compound 41)

Step 1: [5-(4-Bromo-2-methoxy-phenyl)-3-methyl-isoxazol-4-yl]-carbamic acid (R)-1-(3-trifluoromethyl-phenyl)-ethyl ester: Prepared according to the procedure described in Example 1, Step 5 using 5-(4-bromo-2-methoxy-phenyl)-3-methyl-isoxazole-4-carboxylic acid and (R)-1-(3-trifluoromethyl-phenyl)-ethanol.

Step 2: {5-[4'-(1-Methanesulfonylaminocarbonyl-cyclopropyl)-3-methoxy-biphenyl-4-yl]-3-methyl-isoxazol-4-yl}-carbamic acid (R)-1-(3-trifluoromethyl-phenyl)-ethyl ester: Prepared according to the procedure described in Example 1, Step 6 using [5-(4-bromo-2-methoxy-phenyl)-3-methyl-isoxazol-4-yl]-carbamic acid (R)-1-(3-trifluoromethyl-phenyl)-ethyl ester and N-{1-[4-(4,4,5,5-tetramethyl-[1,3,2]dioxaborolan-2-yl)-phenyl]-cyclopropanecarbonyl}-methanesulfonamide.

Example 41

Synthesis of 1-{4'-[4-((R)-1-Phenyl-ethoxycarbonylamino)-isoxazol-5-yl]-biphenyl-4-yl}-cyclopropanecarboxylic acid (Compound 33)

Step 1: 5-(4-Bromo-phenyl)-isoxazole-4-carboxylic acid ethyl ester: A solution of ethyl (4-bromobenzoyl)acetate (1.19 g, 4.39 mmol) in N,N-dimethylformamide dimethyl acetal (10 mL) was stirred at 100° C. for 1 hour. The mixture was concentrated, and the residue was dissolved in EtOH (10 mL). Hydroxylamine hydrochloride (0.454 g, 6.57 mmol) was added, and the reaction was stirred at 100° C. for 1 hour. After cooling to room temperature, the mixture was partitioned between EtOAc and H$_2$O, and the organic layer was separated, dried over MgSO$_4$, filtered, and concentrated. The crude material was purified by silica gel chromatography to give the title compound.

Step 2: 5-(4-Bromo-phenyl)-isoxazole-4-carboxylic acid: 5-(4-Bromo-phenyl)-isoxazole-4-carboxylic acid ethyl ester (0.500 g, 1.69 mmol) was dissolved in concentrated hydrochloric acid (2 mL), acetic acid (5 mL), and H$_2$O (5 mL), and the reaction was stirred at 100° C. overnight. The mixture was partitioned between EtOAc and H$_2$O, and the organic layer was separated, dried over MgSO$_4$, filtered, and concentrated to give the title compound.

Step 3: [5-(4-Bromo-phenyl)-isoxazol-4-yl]-carbamic acid (R)-1-phenyl-ethyl ester: Prepared according to the procedure described in Example 1, Step 5 using 5-(4-bromo-phenyl)-isoxazole-4-carboxylic acid and (R)-1-phenyl-ethanol.

Step 4: 1-{4'-[4-((R)-1-Phenyl-ethoxycarbonylamino)-isoxazol-5-yl]-biphenyl-4-yl}-cyclopropanecarboxylic acid: Prepared according to the procedure described in Example 1, Step 6 using [5-(4-bromo-phenyl)-isoxazol-4-yl]-carbamic acid (R)-1-phenyl-ethyl ester and 4-(1-carboxycyclopropyl) phenylboronic acid.

Example 42

Synthesis of 1-{4'-[3-Methyl-4-(1-phenyl-ethoxycarbonylamino)-isoxazol-5-yl]-biphenyl-4-yl}-cyclopropanecarboxylic acid (Compound 34)

Prepared according to the procedure described in Example 1 for Compound 1 but using racemic 1-phenylethyl alcohol in place of (R)-(+)-1-phenylethyl alcohol.

In some embodiments, mass spectrometric data (mass spec. data) is obtained with a Shimadzu LCMS 2010A.

Example 43

Establishment of a CHO Cell Line Stably Expressing Human $LPA_1$

A 1.1 kb cDNA encoding the human $LPA_1$ receptor was cloned from human lung. Human lung RNA (Clontech Laboratories, Inc. USA) was reverse transcribed using the RETROscript kit (Ambion, Inc.) and the full-length cDNA for human $LPA_1$ was obtained by PCR of the reverse transcription reaction. The nucleotide sequence of the cloned human $LPA_1$ was determined by sequencing and confirmed to be identical to the published human $LPA_1$ sequence (An et al. Biochem. Biophys. Res. Commun. 231:619 (1997). The cDNA was cloned into the pcDNA5/FRT expression plasmid and transfected in CHO cells using lipofectamine 2000 (Invitrogen Corp., USA). Clones stably expressing human $LPA_1$ were selected using hygromycin and identified as cells that show Ca-influx in response to LPA.

Example 44

Generation of Cells Transiently Expressing Human $LPA_2$

A vector containing the human $LPA_2$ receptor cDNA was obtained from the Missouri S&T cDNA Resource Center (www.cdna.org). The full-length cDNA fragment for human $LPA_2$ was obtained by PCR from the vector. The nucleotide sequence of the cloned human $LPA_2$ was determined by sequencing and confirmed to be identical to the published human $LPA_2$ sequence (NCBI accession number NM_004720). The cDNA was cloned into the pcDNA3.1 expression plasmid and transfected into B103 cells (Invitrogen Corp., USA) by seeding cells in a 96-well poly-D-lysine coated plate at 30,000-35,000 cells per well together with 0.2 µl lipofectamine 2000 and 0.2 µg of the $LPA_2$ expression vector. Cells were cultured overnight in complete media before being assayed for LPA-induced Ca-influx.

Example 45

Establishment of a CHO Cell Line Stably Expressing Human $LPA_3$

A vector containing the human $LPA_3$ receptor cDNA was obtained from the Missouri S&T cDNA Resource Center (www.cdna.org). The full-length cDNA fragment for human $LPA_3$ was obtained by PCR from the vector. The nucleotide sequence of the cloned human $LPA_3$ was determined by sequencing and confirmed to be identical to the published human $LPA_3$ sequence (NCBI accession number NM_012152). The cDNA was cloned into the pcDNA5/FRT expression plasmid and transfected in CHO cells using lipofectamine 2000 (Invitrogen Corp., USA). Clones stably expressing human $LPA_3$ were selected using hygromycin and identified as cells that show Ca-influx in response to LPA.

Example 46

LPA1 and LPA3 Calcium Flux Assays

Human $LPA_1$ or $LPA_3$ expressing CHO cells are seeded at 20,000-45,000 cells per well in a 96-well poly-D-lysine coated plate one or two days before the assay. Prior to the assay, the cells are washed once with PBS and then cultured in serum-free media overnight. On the day of the assay, a calcium indicator dye (Calcium 4, Molecular Devices) in assay buffer (HBSS with $Ca^{2+}$ and $Mg^{2+}$ and containing 20 mM Hepes and 0.3% fatty-acid free human serum albumin) is added to each well and incubation continued for 1 hour at 37° C. 10 µl of test compounds in 2.5% DMSO are added to the cells and incubation continued at room temperature for 30 minutes. Cells are the stimulated by the addition of 10 nM LPA and intracellular $Ca^{2+}$ measured using the Flexstation 3 (Molecular Devices). $IC_{50}$s are determined using Graphpad prism analysis of drug titration curves.

Example 47

LPA2 Calcium Flux Assay

BT-20 human breast cancer cells are seeded at 25,000-35,000 cells per well in 150 µl complete media on Poly-D-Lysine coated black-wall clear-bottom plates. Following an overnight culture, cells are washed once with PBS then serum starved for 4-6 hours prior to the assay. On the day of the assay, a calcium indicator dye (Calcium 5, Molecular Devices) in assay buffer (HBSS with $Ca^{2+}$ and $Mg^{2+}$ and containing 20 mM Hepes and 0.3% fatty-acid free human serum albumin) is added to each well and incubation continued for 15 minutes at 37° C. 25 µl of test compounds in 2.5% DMSO are added to the cells and incubation continued at 37° C. for 15 minutes. Cells are the stimulated by the addition of 100 nM LPA and intracellular $Ca^{2+}$ measured using the Flexstation 3 (Molecular Devices). $IC_{50}$s are determined using Symyx Assay Explorer analysis of drug titration curves.

Example 48

GTPγS Binding Assay

The ability of a compound to inhibit binding of GTP to $LPA_1$ is assessed via a membrane GTPγS assay. CHO cells stably expressing the recombinant human $LPA_1$ receptor are resuspended in 10 mM Hepes, 7.4 containing 1 mM DTT, lysed and centrifuged at 75,000×g to pellet the membranes. The membranes are resuspended in 10 mM Hepes, 7.4 containing 1 mM DTT and 10% glycerol. Membranes (~25 µg per well) are incubated in 96-well plates with 0.1 nM [$^{35}$S]-GTPγS, 900 nM LPA, 5 µM GDP, and test compound in Assay Buffer (50 mM Hepes, pH 7.4, 100 mM NaCl, 10 mM $MgCl_2$, 50 µg/ml saponin and 0.2% fatty-acid free human serum albumin) for 30 minutes at 30° C. The reactions are terminated by rapid filtration through Whatman GF/B glass fibre filter plates. The filter plates are washed 3 times with 1 ml cold Wash Buffer (50 mM Hepes, 7.5, 100 mM NaCl and 10 mM $MgCl_2$) and dried. Scintillant is then added to the plates and the radioactivity retained on the filters is determined on a Packard TopCount (Perkin Elmer). Specific binding is determined as total radioactive binding minus non-specific binding in the absence of the ligand (900 nM LPA). $IC_{50}$s were determined using Graphpad prism analysis of drug titration curves.

Illustrative in vitro biological data for representative compounds of Formula (I) is presented in the Table below.

| Compound No. | HLPA1 Ca Flux $IC_{50}$ | HLPA3 Ca Flux $IC_{50}$ |
|---|---|---|
| 1 | A | C |
| 2 | A | C |
| 3 | A | B |
| 4 | A | D |
| 5 | C | ND |
| 6 | A | D |
| 7 | A | D |
| 8 | A | B |
| 9 | A | C |
| 10 | A | C |
| 11 | A | C |
| 12 | A | ND |
| 13 | C | ND |
| 14 | A | C |
| 15 | A | C |
| 16 | A | C |
| 17 | A | B |
| 18 | A | C |
| 19 | A | C |
| 20 | A | C |
| 21 | A | A |
| 22 | A | A |
| 23 | A | C |
| 24 | A | D |
| 25 | A | B |
| 26 | A | B |
| 27 | A | D |
| 28 | A | D |
| 29 | A | B |
| 30 | A | A |
| 31 | A | A |
| 32 | A | C |
| 33 | A | C |
| 34 | A | C |
| 35 | A | C |
| 36 | A | C |
| 37 | C | D |
| 38 | A | C |
| 39 | A | C |
| 40 | A | B |
| 41 | A | B |

A = less than 0.3 µM; B = greater than 0.3 µM and less than 1 µM; C = greater than 1 µM and less than 10 µM; D = greater than 10 µM. ND = not determined Example 49

LPA1 Chemotaxis Assay

Chemotaxis of the A2058 human melanoma cells was measured using the Neuroprobe ChemoTx® System plates (8 µM pore size, 5.7 mm diameter sites). The filter sites were coated with 0.001% fibronectin (Sigma) in 20 mM Hepes, pH 7.4 and allowed to dry. A2058 cells were serum-starved for 24 hours, then harvested with Cell Stripper and resuspended in DMEM containing 0.1% fatty-acid-free bovine serum albumin (BSA) to a concentration of $1 \times 10^6$/ml. Cells were mixed with an equal volume of test compound (2×) in DMEM containing 0.1% fatty-acid-free BSA and incubated at 37° C. for 15 minutes. LPA (100 nM in DMEM containing 0.1% fatty-acid-free BSA) or vehicle was added to each well of the lower chamber and 50 µl of the cell suspension/test compound mix was applied to the upper portion of the ChemoTx plate. Plates were incubated at 37° C. for three hours and then the cells removed from the upper portion by rinsing with PBS and scraping. The filter was dried then stained with HEMA 3 Staining System (Fisher Scientific). The absorbance of the filter was read at 590 nM and $IC_{50}$s were determined using Symyx Assay Explorer.

In this experiment, compounds 1, 4, 8, 16, 17, 19, 21, 29, 35, 36, 38, 39, inhibited LPA-driven chemotaxis ($IC_{50}$ less than 100 nM) of human A2058 melanoma cells Example 50

Bleomycin-Induced Lung Fibrosis Model in Mice

Female C57B1/6 mice (Harlan, 25-30 g) are housed 4 per cage, given free access to food and water and allowed to acclimate for at least 7 days prior to test initiation. After the habituation phase, mice are lightly anesthetized with isoflurane (5% in 100% $O_2$) and administered with bleomycin sulfate (0.01-5 U/kg, Henry Schein) via intratracheal instillation (Cuzzocrea S et al. *Am J Physiol Lung Cell Mol Physiol*. 2007 May; 292(5):L1095-104. Epub 2007 Jan. 12.). Mice are returned to their cages and monitored daily for the duration of the experiment. Test compound or vehicle is delivered po, ip or sc daily. The route and frequency of dosing is based on previously determined pharmacokinetic properties. All animals are sacrificed using inhaled isoflurane 3, 7, 14, 21 or 28 days after bleomycin instillation. Following sacrifice, mice are intubated with a 20 gauge angiocatheter attached to a 1 ml syringe. Lungs are lavaged with saline to obtain bronchoalveolar lavage fluid (BALF) and then removed and fixed in 10% neutral buffered formalin for subsequent histopathological analysis. BALF is centrifuged for 10 min at 800×g to pellet the cells and the cell supernatant removed and frozen at −80° C. for subsequent protein analysis using the DC protein assay kit (Biorad, Hercules, Calif.) and soluble collagen analysis using Sircol (Biocolor Ltd, UK). BALF is analyzed for concentrations of inflammatory, pro-fibrotic and tissue injury biomarkers including transforming growth factor β1, hyaluronic acid, tissue inhibitor of metalloproteinase-1, matrix matelloproteinase-7, connective tissue growth factor and lactate dehydrogenase activity, using commercially available ELISA. The cell pellet is re-suspended in PBS. Total cell counts are then obtained using a Hemavet hematology system (Drew Scientific, Wayne, Pa.) and differential cells counts are determined using Shandon cytospin (Thermo Scientific, Waltham, Mass.). Lung tissue is stained using hematoxylin and eosin (H&E) and trichrome and lung fibrosis is determined by semiquantitative histopathological scoring (Ashcroft T. et al. *J. Clin. Path*. 1988; 41; 4, 467-470) using light microscopy (10× magnification) and quantitative, computer-assisted densitometry of collagen in lung tissue sections using light microscopy. The data are plotted using Graphpad prism and statistical differences between groups determined.

In the acute setting (3 day), Compound 1 significantly reduced total protein and collagen concentrations in broncheoalveolar lavage fluid (BALF). In a 7-day bleomycin model compound 1 reduced BALF collagen, protein, TGFβ1, MMP-7, hyaluronan, and inflammatory cell influx. In the chronic setting (14 day bleomycin model), Compound 1 decreased total lung collagen when dosed either propylactically (day 0-day 14) or therapeutically (day 3-day 14).

Example 51

Mouse Carbon Tetrachloride ($CCl_4$)-Induced Liver Fibrosis Model

Female C57BL/6 mice (Harlan, 20-25 g) housed 4/cage are given free access to food and water and allowed to acclimate for at least 7 days prior to test initiation. After the habituation phase, mice receive $CCl_4$ (1.0 ml/kg body weight) diluted in corn oil vehicle (100 μL volume) via i.p. injection twice a week for 8 weeks. (Higazi, A. A. et al., *Clin Exp Immunol.* 2008 April; 152(1):163-73. Epub 2008 Feb. 14.). Control mice receive an equivalent volume of corn oil vehicle only. Test compound or vehicle is delivered po, ip or sc daily. At the end of the study (8 weeks after first i.p. injection of $CCl_4$), mice are sacrificed using inhaled isoflurane and blood is drawn via cardiac puncture for subsequent analysis of ALT/AST levels. The liver is harvested, and one half of the liver is frozen at −80° C. and the other half is fixed in 10% neutral buffered formalin for histological assessment of liver fibrosis using light microscopy (10× magnification). Liver tissue homogenates are analyzed for collagen levels using Sircol (Biocolor Ltd, UK). Fixed Liver tissue is stained using hematoxylin and eosin (H&E) and trichrome and liver fibrosis is determined by quantitative, computer-assisted densitometry of collagen in liver tissue sections using light microscopy. Plasma and liver tissue lysates are also analyzed for concentrations of inflammatory, pro-fibrotic and tissue injury biomarkers including transforming growth factor β1, hyaluronic acid, tissue inhibitor of metalloproteinase-1, matrix matelloproteinase-7, connective tissue growth factor and lactate dehydrogenase activity, using commercially available ELISA. The resulting data are plotted using Graphpad prism and statistical differences between groups determined.

In this experiment, Compound 1 significantly reduced liver weight increase and collagen deposition in the liver as compared to the untreated group.

Example 52

Mouse Intravenous LPA-Induced Histamine Release

A mouse intravenous LPA-induced histamine release model is utilized to determine the in vivo potency of $LPA_1$ and $LPA_3$ receptor antagonists. Female CD-1 mice (weighing 25-35 grams) are administered compound (i.p., s.c. or p.o.) in a volume of 10 ml/kg 30 minutes to 24 hours prior to intravenous LPA challenge (300 μg/mouse in 0.1% FAF BSA). Immediately following LPA challenge mice are placed into an enclosed Plexiglas chamber and exposed to an isoflurane for a period of 2 minutes. They are removed, decapitated and trunk blood collected into tubes containing EDTA. Blood is then centrifuged at 10,000×g for 10 minutes at 4° C. Histamine concentrations in the plasma are determined by EIA. Drug concentrations in plasma are determined by mass spectrometry. The dose to achieve 50% inhibition of blood histamine release is calculated by nonlinear regression (Graphpad Prism) and plotted as the $ED_{50}$. The plasma concentration associated with this dose is plotted as the $EC_{50}$.

Example 53

Mouse Dermal Vascular Leak Assay

Female BALB/c mice (Harlan) weighing 20-25 grams were given free access to standard mouse chow and water and were allowed to acclimate for two weeks prior to study initiation. Compound 1 was prepared in water vehicle at a concentration of 3 mg/ml and delivered by oral gavage at a volume of 10 ml/kg to yield a dose of 30 mg/kg. Three hours following dose, mice were placed into a restraining device and given Evan's blue dye intravenously by tail vein injection (0.2 ml of a 0.5% solution). Mice were then anesthetized using 3% isoflurane anaesthesia to allow for intradermal injection of LPA (30 μg in 20 μl 0.1% fatty acid free BSA). Thirty minutes after LPA injection mice were sacrificed by $CO_2$ inhalation and the skin removed from the challenge site and placed into 2 ml formamide for overnight extraction of Evan's blue dye.

Following extraction, a 150 μl aliquot of formamide for each tissue sample was placed into a 96 well plate and read at 610 nm using a photospectometer. The resulting data (OD units) were plotted using GraphPad Prizm. In this experiment compound 1 reduced LPA-induced Evan's blue dye leak into the skin.

Example 54

Mouse Unilateral Ureteral Obstruction Kidney Fibrosis Model

Female C57BL/6 mice (Harlan, 20-25 g) housed 4/cage will be given free access to food and water and allowed to acclimate for at least 7 days prior to test initiation. After the habituation phase, mice undergo unilateral ureteral obstruction (UUO) surgery or sham to left kidney. Briefly, a longitudinal, upper left incision is performed to expose the left kidney. The renal artery is located and 6/0 silk thread is passed between the artery and the ureter. The thread is looped around the ureter and knotted 3 times insuring full ligation of ureter. The kidney is returned to abdomen, the abdominal muscle is sutured and the skin is stapled closed. Mice are returned to their cages and monitored daily for the duration of the experiment. Test compound or vehicle is delivered po, ip or sc daily. The route and frequency of dosing is based on previously determined pharmacokinetic properties. All animals are sacrificed using inhaled isoflurane 4, 8 or 14 days after UUO surgery. Following sacrifice blood is drawn via cardiac puncture, the kidneys are harvested and one half of the kidney is frozen at −80° C. and the other half is fixed in 10% neutral buffered formalin for histological assessment of kidney fibrosis using light microscopy (10× magnification). Kidney tissue homogenates are analyzed for collagen levels using Sircol (Biocolor Ltd, UK). Fixed kidney tissue is also stained using hematoxylin and eosin (H&E) and trichrome and kidney fibrosis is determined by quantitative, computer-assisted densitometry of collagen in liver tissue sections using light microscopy and collagen content in kidney lysate. Plasma and kidney tissue lysates are also analyzed for concentrations of inflammatory, pro-fibrotic and tissue injury biomarkers including transforming growth factor β1, hyaluronic acid, tissue inhibitor of metalloproteinase-1, and plasminogen activator inhibitor-1, using commercially available ELISA. The resulting data are plotted using Graphpad prism and statistical differences between groups determined.

In this experiment, Compound 1 reduced total kidney collogen, collagen Type 1, transforming growth factor β1, hyaluronic acid, tissue inhibitor of metalloproteinase-1 and plasminogen activator inhibitor-1 compared to untreated group Example 55

Clinical Trial in Humans with Idiopathic Pulmonary Fibrosis (IPF) Purpose

The purposes of this study is to assess the efficacy of treatment with a compound of Formula (I) compared with placebo in patients with idiopathic pulmonary fibrosis (IPF) and to assess the safety of treatment with a compound of Formula (I) compared with placebo in patients with IPF.

The primary outcome variable is the absolute change in percent predicted forced vital capacity (FVC) from baseline to Week 72.

Secondary outcome measures include: composite outcomes of important IPF-related events; progression-free survival; categorical assessment of absolute change in percent predicted FVC from baseline to Week 72; change in Shortness-of-Breath from baseline to Week 72; change in percent predicted hemoglobin (Hb)-corrected carbon monoxide diffusing capacity (DLco) of the lungs from baseline to Week 72; change in oxygen saturation during the 6 minute walk test (6MWT) from baseline to Week 72; change in high-resolution computed tomography (HRCT) assessment from baseline to Week 72; change in distance walked in the 6MWT from baseline to Week 72.

Criteria

Patients eligible for this study include those patients that satisfy the following inclusion criteria: diagnosis of IPF; 40 to 80 years of age; FVC≧50% predicted value; DLco≧35% predicted value; either FVC or DLco≦90% predicted value; no improvement in past year; able to walk 150 meters in 6 minutes and maintain saturation ≧83% while on no more than 6 L/min supplemental oxygen.

Patients are excluded from this study if they satisfy any of the following criteria: unable to undergo pulmonary function testing; evidence of significant obstructive lung disease or airway hyper-responsiveness; in the clinical opinion of the investigator, the patient is expected to need and be eligible for a lung transplant within 72 weeks of randomization; active infection; liver disease; cancer or other medical condition likely to result in death within 2 years; diabetes; pregnancy or lactation; substance abuse; personal or family history of long QT syndrome; other IPF treatment; unable to take study medication; withdrawal from other IPF trials. Patients are orally dosed with either placebo or an amount of compound of Formula (I) (1 mg/day-1000 mg/day). The primary outcome variable will be the absolute change in percent predicted FVC from Baseline to Week 72. Patients will receive blinded study treatment from the time of randomization until the last patient randomized has been treated for 72 weeks. A Data Monitoring Committee (DMC) will periodically review safety and efficacy data to ensure patient safety.

After week 72, patients who meet the Progression of Disease (POD) definition, which is a ≧10% absolute decrease in percent predicted FVC or a ≧15% absolute decrease in percent predicted DLco, will be eligible to receive permitted IPF therapies in addition to their blinded study drug. Permitted IPF therapies include corticosteroids, azathioprine, cyclophosphamide and N-acetyl-cysteine.

Example 56

Parenteral Pharmaceutical Composition

To prepare a parenteral pharmaceutical composition suitable for administration by injection (subcutaneous, intravenous, and the like), 100 mg of a water-soluble salt of a compound of Formula (I) is dissolved in sterile water and then mixed with 10 mL of 0.9% sterile saline. The mixture is incorporated into a dosage unit form suitable for administration by injection In another embodiment, the following ingredients are mixed to form an injectable formulation: 1.2 g of a compound of Formulas (I), 2.0 mL of sodium acetate buffer solution (0.4 M), HCl (1 N) or NaOH (1 M) (q.s. to suitable pH), water (distilled, sterile) (q.s. to 20 mL). All of the above ingredients, except water, are combined and stirred and if necessary, with slight heating if necessary. A sufficient quantity of water is then added.

Example 57

Oral Pharmaceutical Composition

To prepare a pharmaceutical composition for oral delivery, 100 mg of a compound of Formula (I) is mixed with 750 mg of starch. The mixture is incorporated into an oral dosage unit for, such as a hard gelatin capsule, which is suitable for oral administration.

Example 58

Sublingual (Hard Lozenge) Pharmaceutical Composition

To prepare a pharmaceutical composition for buccal delivery, such as a hard lozenge, mix 100 mg of a compound of Formula (I) with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 59

Fast-Disintegrating Sublingual Tablet

A fast-disintegrating sublingual tablet is prepared by mixing 48.5% by weigh of a compound of Formula (I), 44.5% by weight of microcrystalline cellulose (KG-802), 5% by weight of low-substituted hydroxypropyl cellulose (50 μm), and 2% by weight of magnesium stearate. Tablets are prepared by direct compression (*AAPS PharmSciTech.* 2006;7(2):E41). The total weight of the compressed tablets is maintained at 150 mg. The formulation is prepared by mixing the amount of compound of Formula (I) with the total quantity of microcrystalline cellulose (MCC) and two-thirds of the quantity of low-substituted hydroxypropyl cellulose (L-HPC) by using a three dimensional manual mixer (Inversina®, Bioengineering AG, Switzerland) for 4.5 minutes. All of the magnesium stearate (MS) and the remaining one-third of the quantity of L-HPC are added 30 seconds before the end of mixing.

Example 60

Inhalation Pharmaceutical Composition

To prepare a pharmaceutical composition for inhalation delivery, 20 mg of a compound of Formula (I) is mixed with 50 mg of anhydrous citric acid and 100 mL of 0.9% sodium chloride solution. The mixture is incorporated into an inhalation delivery unit, such as a nebulizer, which is suitable for inhalation administration.

Example 61

Rectal Gel Pharmaceutical Composition

To prepare a pharmaceutical composition for rectal delivery, 100 mg of a compound of Formula (I) is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 62

Topical Gel Pharmaceutical Composition

To prepare a pharmaceutical topical gel composition, 100 mg of a compound of Formula (I) is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topicl administration.

Example 63

Ophthalmic Solution

To prepare a pharmaceutical opthalmic solution composition, 100 mg of a compound of Formula (I) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Example 64

Nasal Spray Solution

To prepare a pharmaceutical nasal spray solution, 10 g of a compound of Formula (I) is mixed with 30 mL of a 0.05M phosphate buffer solution (pH 4.4). The solution is placed in a nasal administrator designed to deliver 100 µl of spray for each application.

The examples and embodiments described herein are for illustrative purposes only and various modifications or changes suggested to persons skilled in the art are to be included within the spirit and purview of this application and scope of the appended claims.

What is claimed is:

1. A method of treating lung fibrosis, renal fibrosis, liver fibrosis, or melanoma, in a mammal comprising administering to said mammal a therapeutically effective amount of a compound according to the following Formula (I), or a pharmaceutically acceptable salt thereof:

Formula (I)

wherein,
$R^1$ is —$CO_2H$, —$CO_2R^D$, —CN, —C(=O)N($R^9$)$_2$, —C(=O)NHCH$_2$CH$_2$SO$_3$H, —C(=O)NHSO$_2R^{10}$, tetrazolyl, or 5-oxo-2,5-dihydro-[1,2,4]oxadiazol-3-yl;
$R^D$ is H or $C_1$-$C_4$alkyl;
$R^3$ is H, $C_1$-$C_4$alkyl, $C_3$-$C_6$cycloalkyl, or $C_1$-$C_4$fluoroalkyl;
$R^4$ is —NR$^7$C(=O)OCH($R^8$)—CY;
$R^7$ is H or $C_1$-$C_4$alkyl;
$R^8$ is H, $C_1$-$C_4$alkyl, or $C_1$-$C_4$fluoroalkyl;
CY is a substituted or unsubstituted $C_3$-$C_6$cycloalkyl or a substituted or unsubstituted phenyl, wherein if CY is substituted then CY is substituted with 1 or 2 $R^C$;
$R^9$ is H, $C_1$-$C_6$alkyl, $C_1$-$C_6$-fluoroalkyl, $C_3$-$C_6$cycloalkyl, or a substituted or unsubstituted phenyl;
$R^{10}$ is a $C_1$-$C_6$alkyl, $C_1$-$C_6$-fluoroalkyl, $C_3$-$C_6$cycloalkyl, or a substituted or unsubstituted phenyl;
each of $R^A$, $R^B$, and $R^C$ are independently selected from F, Cl, Br, I, —CN, —OH, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;
m is 0, 1, or 2;
n is 1, 2, 3 or 4; and
p is 0, 1, or 2;
in combination with at least one additional agent selected from the group consisting of an immunosuppressant, an anti-inflammatory agent, and an agent used in the treatment of a respiratory condition.

2. The method according to claim 1, wherein said immunosuppressant is a corticosteroid.

3. The method according to claim 1, wherein:
$R^1$ is —$CO_2H$, —$CO_2R^D$, —C(=O)NHSO$_2R^{10}$ or tetrazolyl;
$R^3$ is H or $C_1$-$C_4$alkyl;
$R^7$ is H;
$R^8$ is H, —CH$_3$ or —CF$_3$;
$R^{10}$ is a $C_1$-$C_6$alkyl or a substituted or unsubstituted phenyl;
each $R^A$ is independently selected from F, Cl, Br, I, —OH, —CH$_3$, —CF$_3$, —OCF$_3$, and —OCH$_3$;
each $R^B$ is independently selected from F, Cl, Br, I, —OH, —CH$_3$, —CF$_3$, —OCF$_3$, and —OCH$_3$;
each $R^C$ is independently selected from F, Cl, Br, I, —OH, —CH$_3$, —CF$_3$, —OCF$_3$, and —OCH$_3$;
m is 0 or 1;
n is 1, 2, or 3; and
p is 0 or 1.

4. The method of claim 3 wherein:
$R^1$ is —$CO_2H$ or —$CO_2R^D$; $R^D$ is H, —CH$_3$, or —CH$_2$CH$_3$;
$R^3$ is H, —CH$_3$ or —CH$_2$CH$_3$;
$R^4$ is —NHC(=O)OCH($R^8$)—CY;
$R^8$ is H, or —CH$_3$; and
CY is a substituted or unsubstituted phenyl, wherein if CY is a substituted phenyl then the phenyl is substituted with 1 or 2 $R^C$.

5. The method of claim 4 wherein the compound of Formula (I) has the following structure:

or is a pharmaceutically acceptable salt thereof.

6. The method of claim 5, wherein:
$R^4$ is

CY is a substituted or unsubstituted phenyl, wherein if CY is a substituted phenyl then the phenyl is substituted with 1 or 2 $R^C$; $R^C$ is F, Cl, —OH, —$CH_3$, —$CF_3$, or —$OCH_3$; and n is 1.

7. The method of claim 1 wherein said compound of Formula (I) is:
- 1-{4'-[3-Methyl-4-((R)-1-phenyl-ethoxycarbonylamino)-isoxazol-5-yl]-biphenyl-4-yl}-cyclopropanecarboxylic acid (Compound 1);
- 1-{4'-[4-(1-Cyclohexyl-ethoxycarbonylamino)-3-methyl-isoxazol-5-yl]-biphenyl-4-yl}-cyclopropanecarboxylic acid (Compound 2);
- 1-{4'-[3-Methyl-4-((R)-1-o-tolyl-ethoxycarbonylamino)-isoxazol-5-yl]-biphenyl-4-yl}-cyclopropanecarboxylic acid (Compound 3);
- 1-[4'-(4-Benzyloxycarbonylamino-3-methyl-isoxazol-5-yl)-biphenyl-4-yl]-cyclopropanecarboxylic acid (Compound 4);
- (S)-1-{4'-[4-(1-Cyclopropyl-ethoxycarbonylamino)-3-methyl-isoxazol-5-yl]-biphenyl-4-yl}-cyclopropanecarboxylic acid (Compound 5);
- (R)-1-{4'-[4-(1-Cyclopropyl-ethoxycarbonylamino)-3-methyl-isoxazol-5-yl]-biphenyl-4-yl}-cyclopropanecarboxylic acid (Compound 6);
- 1-[4'-(4-Cyclopropylmethoxycarbonylamino-3-methyl-isoxazol-5-yl)-biphenyl-4-yl]-cyclopropanecarboxylic acid (Compound 7);
- 1-(4'-{4-[(R)-1-(2-Chloro-phenyl)-ethoxycarbonylamino]-3-methyl-isoxazol-5-yl}-biphenyl-4-yl)-cyclopropanecarboxylic acid (Compound 8);
- 1-(4'-{3-Methyl-4-[(R)-1-(2-trifluoromethyl-phenyl)-ethoxycarbonylamino]-isoxazol-5-yl}-biphenyl-4-yl)-cyclopropanecarboxylic acid (Compound 9);
- 1-{4'-[3-Methyl-4-((R)-1-phenyl-ethoxycarbonylamino)-isoxazol-5-yl]-biphenyl-4-yl}-cyclobutanecarboxylic acid (Compound 10);
- 1-{4'-[3-Methyl-4-((R)-1-phenyl-ethoxycarbonylamino)-isoxazol-5-yl]-biphenyl-4-yl}-cyclopentanecarboxylic acid (Compound 11);
- 1-(4'-{4-[1-(2-Methoxy-phenyl)-ethoxycarbonylamino]-3-methyl-isoxazol-5-yl}-biphenyl-4-yl)-cyclopropanecarboxylic acid (Compound 12);
- 1-(4'-{3-Methyl-4-[1-(4-trifluoromethyl-phenyl)-ethoxycarbonylamino]-isoxazol-5-yl}-biphenyl-4-yl)-cyclopropanecarboxylic acid (Compound 13);
- 1-(4'-{3-Methyl-4-[1-(4-trifluoromethyl-phenyl)-ethoxycarbonylamino]-isoxazol-5-yl}-biphenyl-4-yl)-cyclopropanecarboxylic acid (Compound 14);
- 1-(4'-{4-[1-(3-Cyano-phenyl)-ethoxycarbonylamino]-3-methyl-isoxazol-5-yl}-biphenyl-4-yl)-cyclopropanecarboxylic acid (Compound 15);
- 1-{4'-[3-Methyl-4-((R)-1-p-tolyl-ethoxycarbonylamino)-isoxazol-5-yl]-biphenyl-4-yl}-cyclopropanecarboxylic acid (Compound 16);
- 1-{4'-[3-Methyl-4-((R)-1-m-tolyl-ethoxycarbonylamino)-isoxazol-5-yl]-biphenyl-4-yl}-cyclopropanecarboxylic acid (Compound 17);
- 1-(4'-{4-[(R)-1-(4-Cyano-phenyl)-ethoxycarbonylamino]-3-methyl-isoxazol-5-yl}-biphenyl-4-yl)-cyclopropanecarboxylic acid (Compound 18);
- 1-(4'-{4-[(R)-1-(2-Cyano-phenyl)-ethoxycarbonylamino]-3-methyl-isoxazol-5-yl}-biphenyl-4-yl)-cyclopropanecarboxylic acid (Compound 19);
- 1-{4'-[4-((R)-1-Cyclobutyl-ethoxycarbonylamino)-3-methyl-isoxazol-5-yl]-biphenyl-4-yl}-cyclopropanecarboxylic acid (Compound 20);
- 1-(4'-{4-[1-(2-Chloro-cyclohex-1-enyl)-ethoxycarbonylamino]-3-methyl-isoxazol-5-yl}-biphenyl-4-yl)-cyclopropanecarboxylic acid (Compound 21);
- 1-(4'-{3-Methyl-4-[(R)-1-(3-trifluoromethyl-phenyl)-ethoxycarbonylamino]-isoxazol-5-yl}-biphenyl-4-yl)-cyclopropanecarboxylic acid (Compound 22);
- 1-(4'-{4-[(R)-1-(3-Methoxy-phenyl)-ethoxycarbonylamino]-3-methyl-isoxazol-5-yl}-biphenyl-4-yl)-cyclopropanecarboxylic acid (Compound 23);
- 1-(4'-{4-[(R)-1-(4-Methoxy-phenyl)-ethoxycarbonylamino]-3-methyl-isoxazol-5-yl}-biphenyl-4-yl)-cyclopropanecarboxylic acid (Compound 24);
- 1-(4'-{4-[1-(3-Bromo-phenyl)-ethoxycarbonylamino]-3-methyl-isoxazol-5-yl}-biphenyl-4-yl)-cyclopropanecarboxylic acid (Compound 25);
- 1-(4'-{4-[1-(3-Chloro-phenyl)-ethoxycarbonylamino]-3-methyl-isoxazol-5-yl}-biphenyl-4-yl)-cyclopropanecarboxylic acid (Compound 26);
- 1-{4'-[3-Methyl-4-((S)-1-phenyl-ethoxycarbonylamino)-isoxazol-5-yl]-biphenyl-4-yl}-cyclopropanecarboxylic acid (Compound 27);
- 1-(4'-{4-[1-(3-Hydroxy-phenyl)-ethoxycarbonylamino]-3-methyl-isoxazol-5-yl}-biphenyl-4-yl)-cyclopropanecarboxylic acid (Compound 28);
- 1-{4'-[3-Ethyl-4-((R)-1-phenyl-ethoxycarbonylamino)-isoxazol-5-yl]-biphenyl-4-yl}-cyclopropanecarboxylic acid (Compound 29);
- 1-(4'-{3-Ethyl-4-[(R)-1-(3-trifluoromethyl-phenyl)-ethoxycarbonylamino]-isoxazol-5-yl}-biphenyl-4-yl)-cyclopropanecarboxylic acid (Compound 30);
- 1-(3'-Methoxy-4'-{3-methyl-4-[(R)-1-(3-trifluoromethyl-phenyl)-ethoxycarbonylamino]-isoxazol-5-yl}-biphenyl-4-yl)-cyclopropanecarboxylic acid (Compound 31);
- 1-(4'-{4-[(R)-1-(3,5-Dibromo-phenyl)-ethoxycarbonylamino]-3-methyl-isoxazol-5-yl}-biphenyl-4-yl)-cyclopropanecarboxylic acid (Compound 32);
- 1-{4'-[4-((R)-1-Phenyl-ethoxycarbonylamino)-isoxazol-5-yl]-biphenyl-4-yl}-cyclopropanecarboxylic acid (Compound 33);
- 1-{4'-[3-Methyl-4-(1-phenyl-ethoxycarbonylamino)-isoxazol-5-yl]-biphenyl-4-yl}-cyclopropanecarboxylic acid (Compound 34);
- {5-[4'-(1-Methanesulfonylaminocarbonyl-cyclopropyl)-biphenyl-4-yl]-3-methyl-isoxazol-4-yl}-carbamic acid (R)-1-phenyl-ethyl ester (Compound 35);
- {5-[4'-(1-Benzenesulfonylaminocarbonyl-cyclopropyl)-biphenyl-4-yl]-3-methyl-isoxazol-4-yl}-carbamic acid (R)-1-phenyl-ethyl ester (Compound 36);
- {5-[4'-(1-Cyano-cyclopropyl)-biphenyl-4-yl]-3-methyl-isoxazol-4-yl}-carbamic acid (R)-1-phenyl-ethyl ester (Compound 37);
- (3-Methyl-5-{4'-[1-(5-oxo-2,5-dihydro-[1,2,4]oxadiazol-3-yl)-cyclopropyl]-biphenyl-4-yl}-isoxazol-4-yl)-carbamic acid (R)-1-phenyl-ethyl ester (Compound 38);
- (3-Methyl-5-{4'-[1-(1H-tetrazol-5-yl)-cyclopropyl]-biphenyl-4-yl}-isoxazol-4-yl)-carbamic acid (R)-1-phenyl-ethyl ester (Compound 39);
- {5-[4'-(1-Methanesulfonylaminocarbonyl-cyclopropyl)-biphenyl-4-yl]-3-methyl-isoxazol-4-yl}-carbamic acid (R)-1-(3-trifluoromethyl-phenyl)-ethyl ester (Compound 40); or
- {5-[4'-(1-Methanesulfonylaminocarbonyl-cyclopropyl)-3-methoxy-biphenyl-4-yl]-3-methyl-isoxazol-4-yl}-carbamic acid (R)-1-(3-trifluoromethyl-phenyl)-ethyl ester (Compound 41);

or a pharmaceutically acceptable salt of any of the preceding compounds.

8. The method of claim 7 wherein said lung fibrosis is idiopathic pulmonary fibrosis.

9. The method of claim 1 wherein the compound of Formula (I) has the following structure:

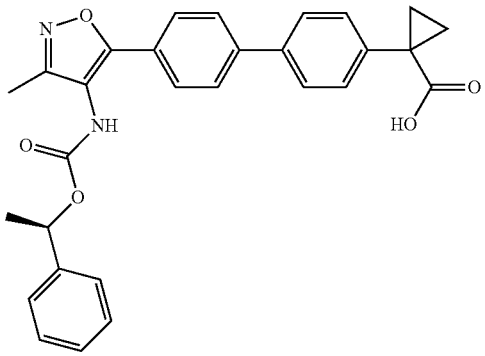

or is a pharmaceutically acceptable salt thereof.

10. A pharmaceutical combination comprising a compound according to claim 1, or a pharmaceutically acceptable salt thereof, together with at least one additional agent selected from the group consisting of an immunosuppressant, an anti-inflammatory agent, or an agent used in the treatment of respiratory conditions.

11. The pharmaceutical combination according to claim 10 wherein the compound of Formula (I) has the structure

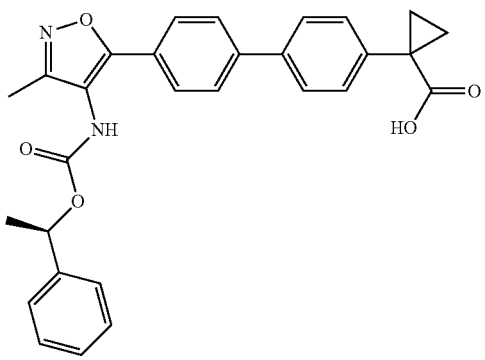

or is a pharmaceutically acceptable salt thereof.

12. A pharmaceutical composition comprising a compound according to claim 1, or a pharmaceutically acceptable salt thereof, together with at least one additional agent selected from the group consisting of an immunosuppressant, an anti-inflammatory agent, or an agent used in the treatment of respiratory conditions in a pharmaceutically acceptable carrier.

13. The pharmaceutical composition according to claim 12 wherein the compound of Formula (I) has the following structure:

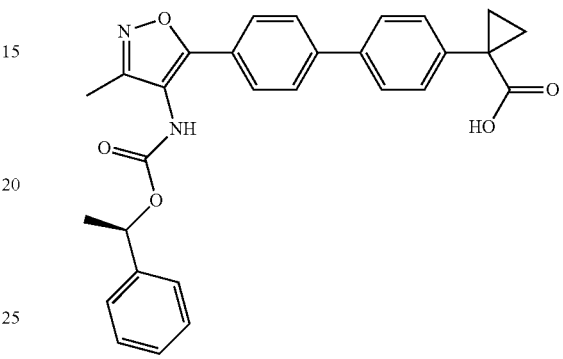

or is a pharmaceutically acceptable salt thereof.

14. The pharmaceutical composition according to claim 13 wherein the pharmaceutically acceptable salt of the compound of Formula (I) is a sodium salt.

15. The pharmaceutical combination according to claim 11 wherein the pharmaceutically acceptable salt of the compound of Formula (I) is a sodium salt.

16. The method according to claim 9 wherein the pharmaceutically acceptable salt of the compound of Formula (I) is a sodium salt.

* * * * *